(12) United States Patent
Daum et al.

(10) Patent No.: US 9,675,592 B2
(45) Date of Patent: Jun. 13, 2017

(54) METHODS AND COMPOSITIONS FOR BACTERIA INFECTIONS

(71) Applicants: THE UNIVERSITY OF CHICAGO, Chicago, IL (US); THE BOARD OF REGENTS OF THE UNIVERSITY OF ILLINOIS, Urbana, IL (US)

(72) Inventors: Robert S. Daum, Chicago, IL (US); Susan Boyle-Vavra, Chicago, IL (US); Michael E. Johnson, Urbana, IL (US)

(73) Assignees: The University of Chicago, Chicago, IL (US); The Board of Regents of the University of Illinois, Urbana, IL (US)

( * ) Notice: Subject to any disclaimer, the term of this patent is extended or adjusted under 35 U.S.C. 154(b) by 0 days.

(21) Appl. No.: 14/776,965

(22) PCT Filed: Mar. 14, 2014

(86) PCT No.: PCT/US2014/029237
§ 371 (c)(1),
(2) Date: Sep. 15, 2015

(87) PCT Pub. No.: WO2014/144710
PCT Pub. Date: Sep. 18, 2014

(65) Prior Publication Data
US 2016/0120852 A1 May 5, 2016

Related U.S. Application Data

(60) Provisional application No. 61/789,716, filed on Mar. 15, 2013.

(51) Int. Cl.
*A61K 31/44* (2006.01)
*A61K 31/519* (2006.01)
(Continued)

(52) U.S. Cl.
CPC .......... *A61K 31/431* (2013.01); *A61K 9/0019* (2013.01); *A61K 31/05* (2013.01);
(Continued)

(58) Field of Classification Search
CPC .. A61K 31/519; A61K 31/427; A61K 31/428; A61K 31/446
(Continued)

(56) References Cited

U.S. PATENT DOCUMENTS

| | | | |
|---|---|---|---|
| 5,776,919 A | 7/1998 | Sukigara et al. | 514/161 |
| 2010/0029597 A1 | 2/2010 | Cottarel et al. | 514/154 |

FOREIGN PATENT DOCUMENTS

| | | |
|---|---|---|
| WO | WO 2012151474 | 11/2012 |
| WO | WO 2014071198 | 5/2014 |

OTHER PUBLICATIONS

Berge, et al., *J Pharmaceutical Sci.* 66(1):1-19, 1977.
(Continued)

*Primary Examiner* — Shengjun Wang
(74) *Attorney, Agent, or Firm* — Norton Rose Fulbright US LLP

(57) ABSTRACT

Compositions and methods are provided for treating or inhibiting a bacterial infection involving at least one antibiotic and a compound that potentiates the antibiotic activity of the antibiotic. In certain embodiments the antibiotic is a beta lactam. In further embodiments, the antibiotic is oxacillin. In additional embodiments, the potentiating compound is an inhibitor of vraSR operon expression. In specific embodiments, the bacterial infection involves an antibiotic-resistant bacteria.

20 Claims, 6 Drawing Sheets

(51) Int. Cl.

| | |
|---|---|
| *A61K 31/53* | (2006.01) |
| *A61K 31/425* | (2006.01) |
| *A61K 31/415* | (2006.01) |
| *A61K 31/05* | (2006.01) |
| *A61K 31/43* | (2006.01) |
| *A61K 31/431* | (2006.01) |
| *A61K 45/06* | (2006.01) |
| *A61K 9/00* | (2006.01) |
| *A61K 31/416* | (2006.01) |
| *A61K 31/4245* | (2006.01) |
| *A61K 31/428* | (2006.01) |
| *A61K 31/4439* | (2006.01) |
| *A61K 31/454* | (2006.01) |
| *A61K 31/4709* | (2006.01) |
| *A61K 31/4725* | (2006.01) |
| *A61K 31/496* | (2006.01) |
| *A61K 31/5377* | (2006.01) |
| *A61K 31/7036* | (2006.01) |

(52) U.S. Cl.
CPC .......... *A61K 31/416* (2013.01); *A61K 31/428* (2013.01); *A61K 31/4245* (2013.01); *A61K 31/4439* (2013.01); *A61K 31/454* (2013.01); *A61K 31/4709* (2013.01); *A61K 31/4725* (2013.01); *A61K 31/496* (2013.01); *A61K 31/519* (2013.01); *A61K 31/5377* (2013.01); *A61K 31/7036* (2013.01); *A61K 45/06* (2013.01)

(58) Field of Classification Search
USPC ......... 514/736, 342, 260.1, 262.1, 367, 371, 514/245, 394, 259.31, 403, 364
See application file for complete search history.

(56) References Cited

OTHER PUBLICATIONS

Boyle-Vavra, et al., *Antimicrob Agents Chemother.* 57(1):83-95, 2013.
Boyle-Vavra, et al., *FEMS Microbiol Lett.* 262(2):163-171, 2006.
Francis, et al., *Infect Immun.* 68(6):3594-3600, 2000.
Jo, et al., *Antimicrob Agents Chemother.* 55:2818-23, 2011.
Livak & Schmittgen, *Methods.* 25(4):402-408, 2001.
Montgomery, et al., *J Infect Dis.* 198(4):561-570, 2008.
Rohner et al. "Synergistic Effect of Quinolones and Oxacillin on Methicillin-Resistant Staphylococcus Species" *Antimicrobial Agents and Chemotherapy*, 33(12): 2037-2041, 1989.
Yin, et al., *Antimicrobial Agents Chemother.* 50(1):336-343, 2006.
International Search Report and Written Opinion issued in PCT/US2014/029237, mailed on Aug. 11, 2014.
Extended European Search Report for EP 14764384.5, mailed Oct. 12, 2016.
Reynolds et al., *Tuberculosis* 92 (2012) 72-83.

SEQUENCE LISTING

<160> NUMBER OF SEQ ID NOS: 12

<210> SEQ ID NO 1
<211> LENGTH: 32
<212> TYPE: DNA
<213> ORGANISM: Artificial Sequence
<220> FEATURE:
<223> OTHER INFORMATION: Synthetic Primer

<400> SEQUENCE: 1
aaagaattct gaaggtatgg tattagctat tg         32

<210> SEQ ID NO 2
<211> LENGTH: 31
<212> TYPE: DNA
<213> ORGANISM: Artificial Sequence
<220> FEATURE:
<223> OTHER INFORMATION: Synthetic Primer

<400> SEQUENCE: 2
aaaggatccg ttgatgtcga tgatatgttt g          31

<210> SEQ ID NO 3
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: 6-FAM
<222> LOCATION: (1)..(1)
<220> FEATURE:
<221> NAME/KEY: ZEN
<222> LOCATION: (9)..(9)
<220> FEATURE:
<221> NAME/KEY: 3'IABkFQ
<222> LOCATION: (26)..(26)

<400> SEQUENCE: 3
ttgccaaagc ccatgagttg aagcca                26

<210> SEQ ID NO 4
<211> LENGTH: 24
<212> TYPE: DNA
<213> ORGANISM: Artificial Sequence
<220> FEATURE:
<223> OTHER INFORMATION: Synthetic Primer

<400> SEQUENCE: 4
tagttggtga aggcgcttct ggta                  24

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer

<400> SEQUENCE: 5
tcgtcgcttc tacaccatcc atgt                  24

<210> SEQ ID NO 6
<211> LENGTH: 26
<212> TYPE: DNA
<213> ORGANISM: Artificial Sequence
<220> FEATURE:
<223> OTHER INFORMATION: Synthetic Primer
<220> FEATURE:

```
<221> NAME/KEY: Cy5
<222> LOCATION: (1)..(1)
<220> FEATURE:
<221> NAME/KEY: 3IAbRQSp
<222> LOCATION: (26)..(26)
<223> OTHER INFORMATION: 3' Iowa Black RQ-Sp

<400> SEQUENCE: 6
aaatgggacg tccagctgtc gaagtt                                              26

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
ccgccaaatt taccaccagc atgt                                                24

<210> SEQ ID NO 8
<211> LENGTH: 24
<212> TYPE: DNA
<213> ORGANISM: Artificial Sequence
<220> FEATURE:
<223> OTHER INFORMATION: Synthetic Primer

<400> SEQUENCE: 8
aacggacgtg gtatcccagt tgat                                                24

<210> SEQ ID NO 9
<211> LENGTH: 29
<212> TYPE: DNA
<213> ORGANISM: Artificial Sequence
<220> FEATURE:
<223> OTHER INFORMATION: Synthetic Primer

<400> SEQUENCE: 9
aaaggatcca aaatcaatca gcaaaatga                                           29

<210> SEQ ID NO 10
<211> LENGTH: 29
<212> TYPE: DNA
<213> ORGANISM: Artificial Sequence
<220> FEATURE:
<223> OTHER INFORMATION: Synthetic Primer

<400> SEQUENCE: 10
aaaaagctta tcgtcatacg aatcctcct                                           29

<210> SEQ ID NO 11
<211> LENGTH: 31
<212> TYPE: DNA
<213> ORGANISM: Artificial Sequence
<220> FEATURE:
<223> OTHER INFORMATION: Synthetic Primer

<400> SEQUENCE: 11
aaaggatcca tgacgattaa agtattgttt g                                        31

<210> SEQ ID NO 12
<211> LENGTH: 25
```

```
<212> TYPE: DNA
<213> ORGANISM: Artificial Sequence
<220> FEATURE:
<223> OTHER INFORMATION: Synthetic Primer

<400> SEQUENCE: 12
aaaaagcttc gatacgaact attga                                25
```

METHODS AND COMPOSITIONS FOR BACTERIA INFECTIONS

CROSS-REFERENCE TO RELATED APPLICATIONS

This application is a national phase application under 35 U.S.C. 371 of International Application No. PCT/US2014/09237, filed on Mar. 14, 2014, which claims the benefit of priority of U.S. Provisional Patent Application No. 61/789,716, filed on Mar. 15, 2013. The entire contents of each of the above-referenced disclosures are specifically incorporated herein by reference without disclaimer.

BACKGROUND OF THE INVENTION

1. Field of the Invention

The present invention relates generally to the field of medicine. More particularly, it concerns the use of chemical compounds that inhibit the vraSR operon and potentiate the action of antibiotics.

2. Description of Related Art

*Staphylococcus aureus* is a well-adapted human parasite that is both a commensal and an important pathogen. It is responsible for a wide variety of infectious diseases that range from minor skin abscesses to severe infections and toxinoses requiring hospitalization. *Staphylococcus aureus* strains resistant to nearly all beta-lactams, so-called methicillin-resistant *Staphylococcus aureus* (MRSA), are a leading cause of healthcare associated and, since the 1990s, community-associated infection. An epidemic of MRSA infections has enhanced the urgency to identify alternative antibacterial agents for successful treatment. Unfortunately, this need comes at a time when the industry-driven pipeline for antibacterial development has slowed.

SUMMARY OF THE INVENTION

Methods and compositions are provided for inhibiting, preventing, or treating a bacterial infection, particularly bacteria that rely on a vraSR operon for signal transduction. This operon is conserved among *Staphylococcus aureus* strains and methods and embodiments concern staphylococcal bacterial infections. In particular, methods and compositions involve an antibiotic and a compound that can be qualified as potentiating the activity of the antibiotic and/or an inhibitor of vraSR operon expression or activity.

In some embodiments, there are methods for inhibiting a *staphylococcus* infection comprising administering to a subject having a *staphylococcus* infection or at risk of a *staphylococcus* infection: (a) an antibiotic, and (b) an antibiotic potentiator, wherein the antibiotic potentiator is a compound of the formula:

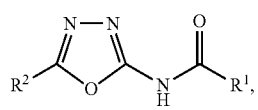

(I)

wherein $R^1$ may be -(4-chlorophenoxy)methyl, 1-(thiophen-2-yl)cyclopentyl, 1,2,3,4-tetrahydronaphthalen-6-yl, 1-isopropyl-1H-pyrazol-5-yl, 2-(thiophen-2-yl)quinolin-4-yl, 2,3-dihydrobenzo[b][1,4]dioxin-6-yl, 2,4-dichlorophenyl, 2,5-dichlorophenyl, 2,5-dichlorothiophen-3-yl, 2,6-difluorophenyl, 2-bromothiophen-5-yl, 2-chlorothiophen-5-yl, 2-naphthyl, 2-phenoxyphenyl, 2-phenylquinolin-4-yl, 3-(2-chlorophenyl)-5-methylisoxazol-4-yl, 3,4,5-trimethoxyphenyl, 3,5-dichlorophenyl, 3,5-dimethoxyphenyl, 3-bromophenyl, 3-chlorobenzo[b]thiophen-2-yl, 3-chlorophenyl, 3-fluorophenyl, 3-methoxyphenyl, 3-n-butoxyphenyl, 3-phenoxyphenyl, 3-tolyl, 3-trifluoromethylphenyl, 4-(2,6-dimethylmorpholinosulfonyl)phenyl, 4-(2-ethylpiperidin-1-ylsulfonyl)phenyl, 4-(2-methylpiperidin-1-ylsulfonyl)phenyl, 4-(2-phenylquinoline), 4-(3,4-dihydroisoquinolin-2(1H)-ylsulfonyl)phenyl, 4-(3,4-(dihydroquinolin-1(2H)-ylsulfonyl)phenyl, 4-(3,5-dimethylpiperidin-1-ylsulfonyl)phenyl, 4-(4,4-dimethyloxazolidin-3-ylsulfonyl)phenyl, 4-(morpholinosulfonyl)phenyl, 4-(N,N-diallylsulfamoyl)phenyl, 4-(N,N-diethylsulfamoyl)phenyl, 4-(N,N-diisobutylsulfamoyl)phenyl, 4-(N,N-dimethylsulfamoyl)phenyl, 4-(N-ethyl-N-benzylsulfamoyl)phenyl, 4-(N-ethyl-N-n-butyl-sulfamoyl)phenyl, 4-(N-ethyl-N-phenylsulfamoyl)phenyl, 4-(N-isopropyl-N-benzylsulfamoyl)phenyl 4-(N-methyl-N-benzylsulfamoyl)phenyl, 4-(N-methyl-N-cyclohexylsulfamoyl)phenyl, 4-(N-methyl-N-n-butylsulfamoyl)phenyl, 4-(N-methyl-N-phenylsulfamoyl)phenyl, 4-(piperidin-1-ylsulfonyl)phenyl, 4-(pyrrolidin-1-ylsulfonyl)phenyl, 4-benzoylphenyl, 4-benzylphenyl, 4-biphenyl, 4-chlorophenyl, 4-diphenyl, 4-ethoxyphenyl, 4-fluorophenyl, 4-phenoxyphenyl, 4-tert-butylphenyl, 7-methoxybenzofuran-2-yl, benzo[d]thiazol-2-yl, benzo[d]thiazol-4-yl, benzo[d]thiazol-6-yl, benzofuran-2-yl, diphenylmethyl, methyl-4-benzoate, phenyl, or thiophen-2-yl, and $R^2$ may be 1,2,3,4-tetrahydronaphthalen-6-yl, 2-(methylthio)phenyl, 2,3-dihydro-1,4-dioxin-2-yl, 2,3-dihydrobenzo[b][1,4]-dioxin-2-yl, 2,3-dihydrobenzo[b][1,4]-dioxin-6-yl, 2,4-dichlorophenyl, 2,4-dimethoxyphenyl, 2,4-dimethylphenyl, 2,5-dichlorophenyl, 2,5-dichlorothiophen-3-yl 2,5-dimethylphenyl, 2-bromothiophen-2-yl, 2-chlorophenyl, 2-chlorothiophen-2-yl, 2-chlorothiophen-5-yl, 2-furanyl, 2-methoxyphenyl, 2-pyridinyl, 3-(methylthio)phenyl, 3,4,5-trimethoxyphenyl, 3,4-dimethoxyphenyl, 3,4-dimethylphenyl, 3,5-dimethoxyphenyl, 3-methoxyphenyl, 3-pyridinyl, 4-chlorophenyl, 4-(methylthio)phenyl, 4-bromophenyl, 4-ethoxyphenyl, 4-fluorophenyl, 4-isopropylbenzyl, 4-methoxybenzyl, 4-methoxyphenyl, 4-pyridinyl, 4-trifluoromethoxyphenyl, 7-ethoxybenzofuran-2-yl, 7-methoxybenzofuran-2-yl, benzofuran-2-yl, benzyl, phenyl, or thiophen-2-yl.

In some embodiments, a composition comprises an antibiotic potentiator having the structure:

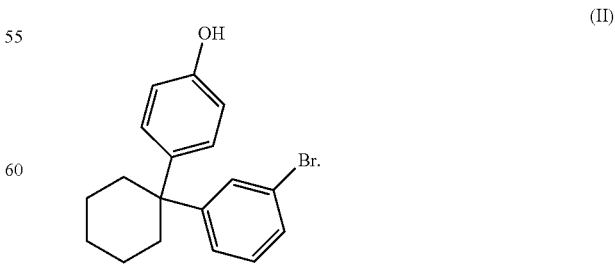

(II)

In further embodiments a composition comprises an antibiotic potentiator having the formula:

(III)

wherein R may be 2-phenoxyphenyl, 2-bromothiophen-5-yl, or 2,5-dichlorophenyl.

Other embodiments concern a composition comprising an antibiotic potentiator having the formula:

(IV)

wherein R may be fluoro, or chloro.

In further embodiments a composition comprises an antibiotic potentiator having the structure:

(V)

In yet further embodiments, a composition comprises an antibiotic potentiator having the structure:

(VI)

Further compositions and methods concern an antibiotic potentiator having the structure:

(VII)

In some embodiments, a composition comprises an antibiotic potentiator having the structure:

(VIII)

In further embodiments a composition comprises an antibiotic potentiator having the structure:

(IX)

In some embodiments there are compositions comprising an antibiotic potentiator having the structure:

(X)

Other compositions concern an antibiotic potentiator having the structure:

(XI)

Further compositions and methods concern an antibiotic potentiator having the formula:

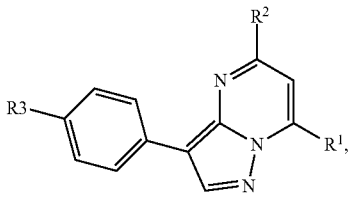

(XII)

wherein R¹ may be N-(4-(phenylamino)-N'-(phenyl)acetamide)amine, N-3-(N',N'-dimethylamine)propylamine, N-(4-N'-phenylacetamide)amine, or hydroxyl, and R² may be tert-butyl, isopropyl, or phenyl, and R³ may be phenyl, or 4-chlorophenyl.

In further embodiments a composition comprises an antibiotic potentiator having the structure:

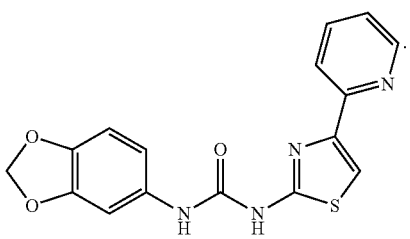

(XIII)

Other compositions concern an antibiotic potentiator having the formula:

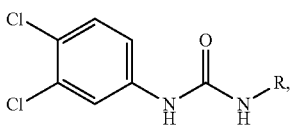

(XIV)

wherein R may be 1H-indazol-6-yl, or 3-(4-methoxyphenoxy)methyloxadiazol-5-yl-methyl.

In some embodiments, a composition comprises an antibiotic potentiator having the formula:

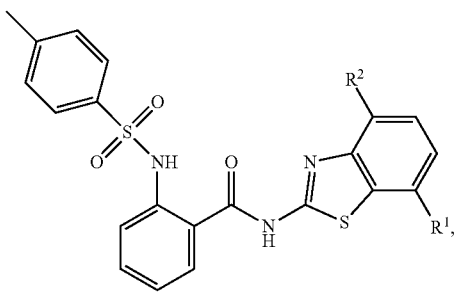

(XV)

wherein, R¹ and R² may each be separately hydrogen, methyl, chloro or methylthio.

In some embodiments, a composition or method concerns an antibiotic potentiator that is depicted herein or as a prodrug or comparable salt thereof.

In additional embodiments, there are methods for inhibiting a *staphylococcus* infection comprising administering to a subject: (a) an antibiotic, and (b) an antibiotic potentiator of that is depicted herein, or a prodrug or salt thereof. In still further embodiments, there are methods for inhibiting a *staphylococcus* infection comprising administering to a subject: (a) an antibiotic, and (b) an antibiotic potentiator that is depicted herein, or a prodrug or salt thereof.

It is specifically contemplated that one or more antibiotic potentiators or a prodrug or salt thereof, may be excluded from methods and compositions discussed herein. In still further embodiments, methods and compositions include an antibiotic as the antibiotic potentiator.

Other methods involve treating a patient with a *staphylococcus* infection comprising administering to the patient an antibiotic and administering to the patient a compound selected from the group consisting of I-XV above, or prodrug or a salt thereof.

Further embodiments concern methods for treating a patient with a *staphylococcus* infection comprising administering to the patient an effective amount of an antibiotic and an effective amount of a compound selected from the group consisting of I-XV above, or prodrug or a salt thereof.

In some embodiments, methods and compositions concern an antibiotic that is a beta-lactam antibiotic. In certain embodiments, the antibiotic is a penicillinase-resistant beta-lactam antibiotic. In further embodiments, the penicillinase-resistant beta-lactam antibiotic is oxacillin. Certain embodiments concern a penicillinase-resistant beta-lactam antibiotic that is methicillin, nafcillin, cloxacillin, dicloxacillin or flucloxacillin. Other antibiotics for use in methods and compositions are discussed below and may include vancomycin, teichoplanin, and/or daptomycin. An antibiotic may be given before, with, or after an antibiotic potentiator is administered to the patient. The antibiotic and the antibiotic potentiator may or may not be formulated similarly. In some embodiments, they are co-formulated or are in the same composition or solution. In one example, one or both of them may be formulated for oral administration. In another example, they may both be formulated for i.v. administration. It is also contemplated that compounds may be administered to a subject by the same or different routes of administration.

Embodiments can be used with a subject that *staphylococcus* can infect, such as mammals, and particularly humans, monkeys, primates, apes, dogs, cats, cows, horses, pigs, goats, mice, or rats. In certain embodiments, the subject is a human patient. In particular methods, the subject has been tested for a *staphylococcus* infection. In other embodiments, the subject is or has been diagnosed with a *staphylococcus* infection. Methods may further involve testing or evaluating a patient for *staphylococcus* infection. In additional embodiments, methods also include diagnosing a patient for *staphylococcus* infection. In some cases, a subject is at risk of acquiring a *staphylococcus* infection. This includes, but is not limited to, patient undergoing an invasive hospital procedure (such as one requiring anesthesia) or surgery, patients having undergone an invasive hospital procedure or surgery, patients placed on an i.v., or patients on a ventilator. In certain embodiments, a subject has one or more symptoms of a staphylococcal infection.

In some methods, the subject has or is at risk for native valve endocarditis or prosthetic valve endocarditis. In other embodiments, the subject has or is at risk for joint infection, meningitis, osteomyelitis, pneumonia, septicemia, sinusitis, or skin or soft tissue infection. In further embodiments, the subject is administered about 2-3 g of oxacillin intravenously every 4 to 6 hours. In other methods, the subject is administered about 1-2 g of oxacillin intravenously or intramuscularly every 4 to 6 hours or about 500 mg to about 1 g of oxacillin orally every 4 to 6 hours. In some methods, before being administered a potentiator, the subject has previously been treated with oxacillin or another antibiotic that induces cell wall stress. In some embodiments, the prior treatment with an antibiotic has been ineffective to treat the infection or the subject or infection has been found to be resistant to the antibiotic. In certain embodiments, the previous treatment was started within 1, 2, 3, 4, 5 weeks and/or 1, 2, 3, 4, 5, or 6 months (or any range derivable therein) of being treated with a potentiator.

In some cases, treating a *Staphylococcus* infection comprises reducing abscess formation or incidence or reducing bacterial load in the subject. In other embodiments, treating a *Staphylococcus* infection comprises reducing symptoms of any infection including but not limited to reducing fever, reducing swelling at the infection site, and/or reducing pain at the infection site.

With some methods and compositions, an infection is from a *staphylococcus* that belongs to the species *Staphylococcus aureus*. In certain embodiments, the *staphylococcus* infection is methicillin resistant *Staphylococcus aureus* (MRSA). In alternative embodiments, the *staphylococcus* infection is methicillin sensitive *Staphylococcus aureus* (MSSA), and the composition is provided to treat the infection while reducing the likelihood of acquisition of methicillin resistance.

Certain methods and compositions may involve a second antibiotic. In some embodiments, methods involve administering the second antibiotic. In particular cases, the second antibiotic is gentamicin or rifampin. Other second antibiotics are discussed below. Methods or compositions may also include a staphylococcal vaccine. Methods include, in particular embodiments, administering a staphylococcal vaccine. This may be administered before, after, or with an antibiotic and/or an antibiotic potentiator.

In some embodiments, the antibiotic is administered at a dose of about 0.1 mg/kg to about 50 mg/kg. In particular embodiments, the subject is a pediatric patient, which means under 18 years of age for a human patient. For a pediatric patient, in some embodiments an antibiotic is administered about 25 mg/kg to about 50 mg/kg intravenously or intramuscularly every 6 to 12 hours or about 12.5 mg/kg orally every 6 hours. In certain embodiments, the antibiotic is oxacillin.

Methods may also involve an antibiotic potentiator administered in a dose of 0.1 mg/kg to about 100 mg/kg.

In some methods administration of a compound to a subject is oral, sublingual, sublabial, gastrointestinal, rectal, epicutaneous (topical), intradermal, subcutaneous, nasal, intravenous, intraarterial, intramuscular, intracardiac, intraosseous, intrathecal, intraperitoneal, intravesical, intravitreal, intracavernous, intravaginal, intrauterine, epidural, intracerebral and/or intracerebroventricular. In specific embodiments, administration is topical, enteral, or parenteral. In some instances, administration is by application onto the skin, inhalation, an enema, eye drops, ear drops, absorption across mucosal membranes, the mouth, a gastric feeding tube, a duodenal feeding tube, a suppository, an injection into a vein, an injection into an artery, an injection into the bone marrow, an injection into muscle tissue, an injection into the brain, an injection into the cerebral ventricular system or an injection under the skin. It is also contemplated that compounds may be administered to a subject by the same or different routes of administration.

In some embodiments the antibiotic and the antibiotic potentiator are in the same composition. In other embodiments the antibiotic and the antibiotic potentiator are administered simultaneously in the same or different compositions. A subject is administered an antibiotic up to 24 hours prior to administration of the antibiotic potentiator in some cases. In others, the antibiotic potentiator is administered up to 24 hours prior to administration of the antibiotic. In some embodiments, the antibiotic and antibiotic potentiator are administered within 24 hours of each other.

Pharmaceutical compositions are also provided. In some embodiments, a pharmaceutical composition includes an antibiotic and a compound selected from the group consisting of I-XV above, or prodrug or a salt thereof. In additional embodiments, a pharmaceutical composition includes a single unit dose of a selected antibiotic and a compound selected from the group consisting of I-XV above.

In some cases, a pharmaceutical composition comprises at least an additional antibacterial agent. The additional antibacterial agent may be a further antibiotic, a staphylococcal vaccine composition or a polypeptide that specifically binds to a second staphylococcal protein. It is contemplated that the pharmaceutical composition may be a pill, capsule, tablet, lozenge, troche, solution, cream, gel, paste, liquid or solid. In embodiments where antibiotic and an antibiotic potentiator are in different compositions, each may be provided in one of these forms.

Additional embodiments concern a system for treating a bacterial infection comprising a pharmaceutically acceptable composition comprising an antibiotic and a pharmaceutically acceptable composition comprising an antibiotic potentiator that is a compound selected from the group consisting of I-XV above. In some system embodiments, the antibiotic is in an aqueous formulation. Further embodiments involve a system in which the antibiotic is in an aqueous formulation that is an intravenous solution or an aqueous formulation that is injectable into the patient or into an intravenous solution. In other embodiments, an antibiotic potentiator is in an aqueous formulation. In certain cases, an antibiotic potentiator is in an aqueous formulation that is an intravenous solution or an aqueous formulation that is injectable into the patient or into an intravenous solution.

Embodiments discussed in the context of compositions may also be applied as methods, and vice versa.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifi-

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Bacterial Growth Inhibition

Figures 1A, 1B, 1C:
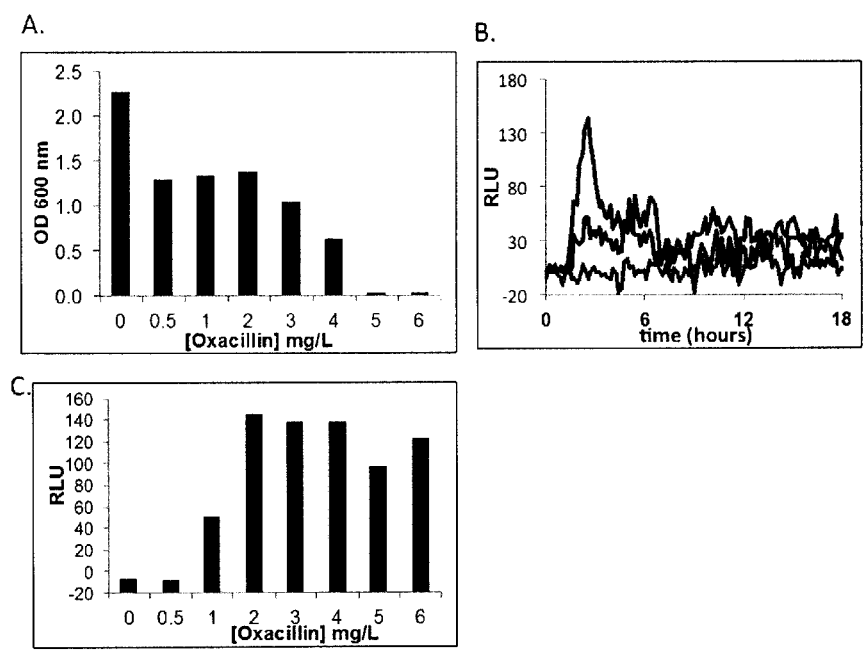
FIG. 1A-C: Optimal conditions for measuring growth and luminescence of the test strain, 923 pPvra-lux. (A) Absorbance at 18 hours as a function of oxacillin concentration. (B) Luminescence (LU) was monitored over 18 hours with oxacillin at 0 μg/mL (blue solid line), 1 μg/mL (green line) and 2 μg/mL (red solid line). (C) Luminescence at two hours post inoculation as a function of oxacillin concentration.

VraS and VraR constitute a two-component signal transduction system that requires a recently renamed third component, VraT (previously called YvqF) that is encoded on the same operon (Boyle-Vavra 2006; Yin 2006; Francis 2000). The vraSR operon, conserved among *Staphylococcus aureus* strains, senses and responds to cell-wall stress elicited by clinically important antibacterials that work by interfering with bacterial cell wall synthesis. This vraSR operon is responsible for activation of a set of genes that presumably coordinately act together to adapt to cell wall stress. Compounds that inhibit expression of the vraSR operon are shown below to enhance the ability of a beta-lactam antibiotic to kill MRSA strains and treat infections caused by them (potentiation).

II. Antibiotics

Embodiments concern methods and compositions for treating bacterial infections, including infections involving antibiotic-resistant bacteria. Substances are provided that can be used in conjunction with antibiotics that are effective or potentially effective for treating or inhibiting a bacterial infection. The antibiotics specifically contemplated for use in embodiments include beta-lactam antibiotics. Some embodiments concern the use of one or more antibiotics in combination with one or more compounds that inhibit the vraSR operon. Further embodiments specifically contemplate the use of compounds that inhibit the vraSR operon together with one or more beta-lactam antibiotics. Yet further embodiments contemplate the use of compounds that inhibit the vraSR operon together with one or more antibiotics known to act via disruption of bacterial cell wall processes.

In some embodiments, *Staphylococcus aureus* is involved in the bacterial infection to be treated. Other embodiments contemplate the use of compounds that inhibit the vraSR operon against the homologous LiaRS system present in *Bacillus subtilis, Streptococcus pneumoniae*, and *Streptococcus mutansi*. Further embodiments contemplate the use of said compounds to target the homologous CesSR system in several *Lactococcus* species. Yet further embodiments contemplate the use of these compounds against other homologous two-component systems of cell-wall-mediated antibiotic resistance.

Certain embodiments contemplate the use of beta-lactam antibiotics. Beta-lactam antibiotics are a broad class of antibiotics, consisting of antibiotic agents that contain a beta-lactam nucleus in their molecular structures. This includes penicillin derivatives (penams), cephalosporins (cephems), monobactams, and carbapenems. Most beta-lactam antibiotics work by inhibiting cell wall biosynthesis in bacteria and are the most widely used group of antibiotics.

It is contemplated that compounds that inhibit the vraSR operon potentiate the action of any beta-lactam antibiotic. This group comprises any of Amoxicillin, Ampicillin, Pivampicillin, Hetacillin, Bacampicillin, Metampicillin, Talampicillin, Epicillin, Carbenicillin Carindacillin, Ticarcillin, Temocillin Azlocillin, Piperacillin, Mezlocillin Mecillinam Pivmecillinam, Sulbenicillin Clometocillin, Benzathine benzylpenicillin, Procaine benzylpenicillin, Azidocillin. Penamecillin, Phenoxymethylpenicillin, Propicillin, Benzathine phenoxymethylpenicillin, Pheneticillin, Cloxacillin, Dicloxacillin, Flucloxacillin, oxacillin, Meticillin, Nafcillin, Faropenem Biapenem, Ertapenem, Doripenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, cephamycin, Cefoxitin, Cefotetan, Cefmetazole, carbacephem, Loracarbef, Cefixime, Ceftriaxone, Ceftazidime, Cefoperazone, Cefcapene, Cefdaloxime, Cefdinir, Cefditoren, Cefetamet, Cefmenoxime, Cefodizime, Cefotaxime, Cefpimizole, Cefpiramide. Cefpodoxime, Cefsulodin, Cefteram, Ceftibuten, Ceftiolene, Ceftizoxime, oxacephem Flomoxef, Latamoxef, Cefepime, Cefozopran, Cefpirome, Cefquinome, Ceftobiprole, Ceftaroline fosamil, Ceftiofur, Cefquinome, Cefovecin, Aztreonam, Tigemonam, Carumonam or Nocardicin A. In embodiments using beta-lactamase sensitive antibiotics such as Amoxicillin, Ampicillin, pivampicillin, hetacillin, bacampicillin, metampicillin, talampicillin, epicillin, carbenicillin carindacillin, ticarcillin, temocillin azlocillin, piperacillin, mezlocillin mecillinam pivmecillinam, sulbenicillin clometocillin, benzathine benzylpenicillin, procaine benzylpenicillin, azidocillin, penamecillin, phenoxymethyl-penicillin, propicillin, benzathine phenoxymethyl-penicillin, or pheneticillin, addition of a beta-lactamase inhibitor is further contemplated.

Further embodiments contemplate the use of other antibiotics that induce the cell wall stress stimulon (CWSS) in *Staphylococcus aureus* and thus involve vraSR such as fosfomycin, D-cycloserine, tunicamycin, bacitracin, bambermycin, vancomycin, moenomycin, teicoplanin, lysostaphin, teichoplanin, and daptomycin. In still further embodiments, the antibiotic is a cationic peptide such as cecropins, andropin, moricin, ceratotoxin, melittin, magainin, dermaseptin, bombinin, brevinin-1, esculentin and buforin II, CAP 18, or LL37.

Experimental data provide support for using compounds that inhibit the vraSR operon as potentiators of vancomycin and related compounds, including those that induce expression of vraSR. The following data from the co-pending application PCT/US2013/068085, which is hereby incorporated by reference in its entirety, demonstrates that the compounds clomiphene, pyrvinium, and gossypol, which were found to inhibit the vraSR operon and to potentiate oxacillin, were also effective potentiators of vancomycin. The ability of clomiphene, pyrvinium, and gossypol to potentiate vancomycin in vitro was tested by performing checkerboard assays with a vancomycin intermediate resistant *Staphylococcus aureus* strain, VISA 2283 (MIC vancomycin 16 mg/L); a hetero VISA isolate, hVISA 2275 (MIC of vancomycin of 4 mg/L), and two vanA containing VRSA strains, VRS1 (MIC of vancomycin 1024 mg/L) and VRS2 (MIC of vancomycin 16 mg/L). In the checkerboard assay, increasing concentrations of vancomycin are arrayed with increasing concentrations of the indicated potentiator. The FICi for each combination was calculated according to the following formula:

$$FIC_i = \frac{[Ox]MIC \text{ in combination}}{MIC \text{ of Van alone}} + \frac{[compound] \text{ in combination}}{MIC \text{ of compound alone}}$$

An $FIC_i$ of $\leq 0.5$ defines a synergistic interaction. An $FIC_i > 0.5$ and $<0.7$ is possibly synergistic. As shown in the analysis of the checkerboard assays (Table 1), gossypol fully potentiated vancomycin (FIC i<0.5) in hVISA, VISA, VRS2 and VRS1. Pyrvinium partially potentiated vancomycin (FIC i>0.5 and <1.0) in hVISA, and fully potentiated in both of the vanA containing VRSA strains but not in the VISA strain. Clomiphene partially potentiated vancomycin in hVISA, VISA, and VRS1 and it fully potentiated in strain VRS2. For gossypol, the degree of vancomycin potentiation was not dependent on the vancomycin MIC of the strain since pyrvinium was a stronger potentiator in VRS1 (which has a vancomycin MIC of 1024 mg/L without compound) than it was for the VISA strain (which has a vancomycin MIC of 8 in the absence of pyrvinium). In the VRSA strain, the MIC of vancomycin decreased by 64 fold whereas in the VISA strain, pyrvinium decreased the vancomycin MIC by 2 to 4 fold.

TABLE 1

Clomiphene (Clo), Vancomycin (Van or V), Pyrvinium (Pyr), Gossypol, (Gos). Van+ indicates vancomycin MIC when used in combination with compound, Clo+, Pyr+ or Gps+ signifies MIC of the compound when used in combination with the indicated Van concentration).

| Strain | MIC (mg/L) | | MIC (in combination)* | | FIC | | FICi | fold decrease Van MIC | Synergy category |
|---|---|---|---|---|---|---|---|---|---|
| Clo | Van | Clo | Van+ | Clo+ | Van FIC | Clo FIC | FICi V + Clo | | |
| hVISA 2275 | 4 | 12 | 2 | 1.5 | 0.5 | 0.13 | 0.63 | 2 | partial |
| hVISA 2275 | 4 | 12 | 1 | 6 | 0.25 | 0.5 | 0.75 | 4 | partial |
| VISA 2283 | 8 | 12 | 4 | 3 | 0.5 | 0.25 | 0.75 | 2 | partial |
| VRS2 | 16 | 12 | 1 | 6 | 0.06 | 0.5 | 0.56 | 16 | partial |
| VRS2 | 16 | 12 | 2 | 3 | 0.13 | 0.25 | 0.38 | 8 | synergistic |
| VRS2 | 16 | 12 | 8 | 1.5 | 0.50 | 0.13 | 0.63 | 2 | partial |
| VRS1 | 1024 | 12 | 512 | 3 | 0.50 | 0.25 | 0.75 | 2 | partial |
| | 1024 | 12 | 256 | 6 | 0.25 | 0.5 | 0.75 | 4 | partial |
| Pyr | Van | Pyr | Van+ | Pyr+ | Van FIC | Pyr FIC | FICi V + Pyr | | |
| hVISA 2275 | 4 | 16 | 2 | 0.56 | 0.50 | 0.04 | 0.54 | 2 | partial |
| VRS2 | 16 | 1.12 | 1 | 0.28 | 0.06 | 0.25 | 0.31 | 16 | synergistic |
| VRS2 | 16 | 1.12 | 2 | 0.14 | 0.13 | 0.13 | 0.25 | 8 | synergistic |
| VRS1 | 1024 | 2.24 | 1 | 1.1 | 0.00 | 0.49 | 0.49 | 1024 | synergistic |
| VRS1 | 1024 | 2.24 | 64 | 0.56 | 0.06 | 0.25 | 0.31 | 16 | synergistic |
| VRS1 | 1024 | 2.24 | 512 | 0.14 | 0.50 | 0.06 | 0.56 | 2 | partial |
| VISA | | | | | | | | | non syn |
| Gos | Van | Gos | Van+ | Gos+ | Van FIC | Gos FIC | FICi V + G | | |
| hVISA 2275 | 4 | 10.4 | 1 | 1.3 | 0.25 | 0.125 | 0.38 | 4 | synergistic |
| VISA 2283 | 8 | 10.4 | 4 | 1.3 | 0.50 | 0.125 | 0.63 | 2 | partial |
| VISA 2283 | 8 | 10.4 | 2 | 5.2 | 0.25 | 0.5 | 0.75 | 4 | partial |

TABLE 1-continued

Clomiphene (Clo), Vancomycin (Van or V), Pyrvinium (Pyr), Gossypol, (Gos). Van+ indicates vancomycin MIC when used in combination with compound, Clo+, Pyr+ or Gps+ signifies MIC of the compound when used in combination with the indicated Van concentration).

| Strain | MIC (mg/L) | | MIC (in combination)* | | FIC | FICi | fold decrease Van MIC | Synergy category |
|---|---|---|---|---|---|---|---|---|
| VRS2 | 16 | 5.2 | 1 | 1.3 | 0.06 | 0.25 | 0.31 | 16 | synergistic |
| VRS1 | 1024 | 20.8 | 16 | 1.3 | 0.02 | 0.0625 | 0.08 | 64 | synergistic |
| VRS1 | 1024 | 20.8 | 1 | 2.6 | 0.001 | 0.125 | 0.13 | 1024 | synergistic |

In additional embodiments compounds listed in Table 5 are envisioned to be used as antibiotics, alone or in combination with the antibiotics or potentiators discussed herein.

Penicillin G is administered in some embodiments to adults in doses ranging from 600,000 to >1,000,000 units. Penicillin G is administered in doses of 20-24 million units daily, in divided doses every 4-6 hours. For children, a dose of penicillin G is about 50,000 units/kg/dose. One unit of penicillin G contains 0.6 μg of pure sodium penicillin G (i.e., 1 mg is 1667 units).

Amoxicillin may be administered to adults in doses ranging from 750 mg to 1.5 grams per day, in 3 divided doses. For children, doses of amoxicillin range from 20 to 40 mg/kg per day in 3 equally divided doses. Amoxicillin is also available in combination with clavulanic acid, a beta-lactamase inhibitor. A 250 mg dose of the combination drug amoxicillin/clavulanate will contain 250 mg of amoxicillin and either 125 or 62.5 mg of clavulanic acid. The combination is preferably administered to adults orally in doses of 750 mg per day divided into 3 equal doses every 8 hours, with a dose of 1.5 grams per day for severe infections, given in 3 equally divided doses. In children, the oral dose is 20 to 40 mg/kg per day in 3 equally divided doses.

In some embodiments ampicillin is administered to adults in doses of 6 to 12 grams per day for severe infections, in 3 to 4 equally divided doses. In children, the dose of ampicillin is 50 to 200 mg/kg per day in 3 to 4 equally divided doses. Larger doses of up to 400 mg/kg per day, for children, or 12 grams per day, for adults, may be administered. Ampicillin is also available in combination with sulbactam, a beta-lactamase inhibitor. Each 1.5 gram dose of ampicillin/sulbactam contains 1 gram of ampicillin and 0.5 grams of sulbactam. The combination is preferably administered to adults in doses of 6 to 12 grams per day divided into 4 equal doses every 6 hours, not to exceed a total of 12 grams per day.

In certain embodiments, azlocillin is typically administered to adults in doses of 8 to 18 grams per day, given in 4 to 6 equally divided doses.

In further embodiments, carbenicillin is administered to adults in doses of 30 to 40 grams per day, given by continuous infusion or in 4 to 6 equally divided doses. Daily doses of up to 600 mg/kg have been used to treat children with life-threatening infections.

Mezlocillin is administered in some embodiments to adults in doses of 100 to 300 mg/kg per day, given in 4 to 6 equally divided doses. The usual dose is 16 to 18 grams per day; for life threatening infections, 350 mg/kg per day may be administered, but in doses not to exceed 24 grams per day given in 6 equally divided doses every 4 hours. For children, the dose of mezlocillin is 150 to 300 mg/kg per day.

Nafcillin is in some embodiments intravenously administered to adults in doses of 3 grams per day, given in 6 equally divided doses every 4 hours, with doubled doses for very severe infections. In conventional administration, it is effective largely against gram-positive organisms. In children, a dose in additional embodiments is 20 to 50 mg/kg per day, in 2 equally divided doses every 12 hours. The oral dose for nafcillin in some embodiments ranges from 1 gram per day to 6 grams per day in 4 to 6 divided doses.

Oxacillin is administered in certain embodiments to adults in doses of 2 to 12 grams per day, in 4 to 6 equally divided doses. In conventional administration, it is effective largely against gram-positive organisms. In children, oxacillin is administered in doses of 100 to 300 mg/kg per day.

Piperacillin is administered to adults in doses ranging from 100 mg/kg, or 6 grams per day, in 2 to 4 equally divided doses, up to a maximum of 24 grams per day, in 4 to 6 equally divided doses. Higher doses have been used without serious adverse effects.

Ticarcillin is administered to adults in doses ranging from 4 grams per day to 18 grams per day administered in 4 to 6 equally divided doses. The usual dose is 200 to 300 mg/kg per day. For children, a typical dose of ticarcillin ranges from 50 mg/kg per day to 300 mg/kg per day, given in 3, 4 or 6 equally divided doses. The combination ticarcillin/clavulanate is administered to adults in doses of 200 to 300 mg/kg per day (based on ticarcillin content), in 4 to 6 equally divided doses. For adults, the usual dose is 3.1 grams (which contains 3 grams of ticarcillin and 100 mg of clavulanic acid) every 4 to 6 hours. The combination is also available in a dose of 3.2 grams, which contains 3 grams of ticarcillin and 200 mg of clavulanic acid.

In additional embodiments, methods and compositions concern cefamandole that is administered to adults in doses ranging from 1.5 grams per day, given in 3 equally divided doses every 8 hours, to 12 grams per day for life-threatening infections, given in 6 equally divided doses every 4 hours. In children, cefamandole is typically administered in doses ranging from 50 to 150 mg/kg per day, in 3 to 6 equally divided doses, not to exceed a total of 12 grams per day.

Cefazolin is administered in some methods to adults in doses of 750 mg per day, given in 3 equally divided doses every 8 hours. In severe, life-threatening infections, it may be administered at doses of 6 grams per day divided into 4 equal doses every 6 hours; in rare instances, up to 12 grams per day have been used. In children, the dose of cefazolin is 20 to 50 mg/kg per day, divided into 3 or 4 equal doses, with 100 mg/kg per day administered for severe infections.

In further embodiments, methods and compositions concern cefonicid that is administered to adults in doses ranging from 500 mg once daily, to 2 grams once daily for life-threatening infections. For intramuscular administration, a 2 gram dose should be divided into two 1-gram injections.

In some methods, cefoperazone is administered to adults in doses ranging from 2 grams per day, given in 2 equally divided doses every 12 hours, to 12 grams per day for severe infections, given in 2, 3 or 4 equally divided doses. Doses up to 16 grams per day have been administered without complications.

In certain embodiments, methods and compositions concern cefotetan that is administered to adults in doses of 1 to 4 grams per day, in 2 equally divided doses every 12 hours. Cefotetan may be administered in higher doses for life-threatening infections, not to exceed a total dose of 6 grams per day.

Cefotaxime is administered in certain embodiments to adults in doses ranging from 1 to 12 grams per day, not to exceed 12 grams per day (2 grams every 4 hours) for life-threatening infections. In children, the parenteral dose of cefotaxime is 50 to 180 mg/kg, divided into 4 to 6 equal doses.

In other embodiments, cefoxitin is administered to adults in doses ranging from 3 to 12 grams per day, given in 3, 4, or 6 equally divided doses. In children, cefoxitin is administered in doses of 80 to 160 mg/kg per day, given in 4 or 6 equally divided doses, not to exceed a total dose of 12 grams per day.

In additional embodiments, methods and compositions concern ceftazidime, which is administered to adults in doses ranging from 500 mg per day, given in 2 to 3 equally divided doses (every 8 or 12 hours), up to a maximum of 6 grams per day. In children, ceftazidime is administered intravenously in doses of 30 to 50 mg/kg, to a maximum of 6 grams per day.

In some cases, ceftizoxime is administered in certain embodiments to adults in doses ranging from 1 gram per day, given in 2 equally divided doses every 12 hours, to 12 grams per day for life-threatening infections, given in 3 equally divided doses every 8 hours. The usual adult dose is 1 to 2 grams every 8 or 12 hours. For children, a parenteral dose is 50 mg/kg every 6 or 8 hours, for a total daily dose of 200 mg/kg in some embodiments.

Ceftriaxone is administered in additional embodiments parentally to adults in doses ranging from 1 to 2 grams per day, given in 2 equally divided doses every 12 hours. It may be given in higher doses, not to exceed a total of 4 grams per day. In children, the dose of ceftriaxone is 50 to 75 mg/kg per day, not to exceed 2 grams per day. Ceftriaxone may be administered in doses of 100 mg/kg per day, not to exceed 4 grams per day.

In further embodiments, cefuroxime is administered to adults in doses ranging from 2.25 to 4.5 grams per day, in 3 equally divided doses every 8 hours. For life-threatening infections, 6 grams per day may be administered in 4 equally divided doses every 6 hours, and for meningitis, 9 grams per day may be administered in 3 equally divided doses every 8 hours. For children, the dose of cefuroxime is 50 to 150 mg/kg per day in 3 to 4 equally divided doses, or 240 mg/kg per day.

Cephalexin is formulated for oral administration, and is sometimes administered orally to adults in doses ranging from 1 to 4 grams per day in 2 to 4 equally divided doses. For children, doses may be 20 to 50 mg/kg per day in divided doses, with doses being doubled for severe infections.

Cephalothin is usually administered to adults in doses of 8 to 12 grams per day.

Fosfomycin is administered either orally or parenterally. In an oral formulation it is given as a single 3-gram dose mixed in 3-4 ounces of water and may be given daily. It may also be administered intravenously or intramuscularly in doses ranging from 2 to 4 grams daily, or up to 16 grams daily in certain cases.

D-cycloserine is administered orally in children and adults in doses ranging from 10 to 15 milligrams per kilogram daily, usually 500-750 milligrams for adults.

Bacitracin is administered topically to adults every 3-4 hours for 5-7 days for treatment of superficial infections. It may also be administered to children and infants via intramuscular injection of 900-1000 international units per kilogram per day, usually in divided doses.

Vancomycin is typically administered to adults via intravascular injection in doses ranging from 30-45 milligrams per kilogram per day. This may be divided over 2-4 administrations daily. It may also be dosed in larger loading doses of 25-30 milligrams per kilogram. It may further be administered orally in doses ranging from 500 milligrams up to 2 grams daily. In children it may be administered intravascularly in doses ranging from 15-45 milligrams per kilogram per day and orally in doses of 40 milligrams per kilogram per day, often with a daily maximum of 2 grams.

Daptomycin is administered to adults intravascularly in doses ranging from 6-8 milligrams per kilogram per day.

The overall composition includes each of the antibiotics in a therapeutically effective amount, along with a second compound that may be referred to as an antibiotic potentiator. The specific amount(s) is dependent on the antibiotic and other compound that is used, the disease or infection to be treated, and the number of times of day that the composition is to be administered.

An antibiotic potentiator refers to a compound or substance that is used in conjunction with an antibiotic to treat or inhibit a bacterial infection, such as a staphylococcal infection. These compounds combine with an antibiotic to increase the inhibitory effect of the antibiotic on the bacteria. Embodiments include an antibiotic potentiator or other compound that increases the ability of the antibiotic to inhibit the growth of bacteria in an in vitro assay, such as an assay disclosed in Example 2 herein, by about, at least about, or at most about the following amounts compared to the antibiotic in the absence of the other compound: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 times, or any range derivable therein.

Embodiments concern a number of compounds that can be used in combination with an antibiotic such as oxacillin. The compounds listed below may be used individually or collectively with one or more antibiotics in methods and compositions provided herein. In other embodiments, the compounds listed below, or a prodrug or salt thereof, may be used individually or collectively with one or more antibiotics in methods and compositions provided herein.

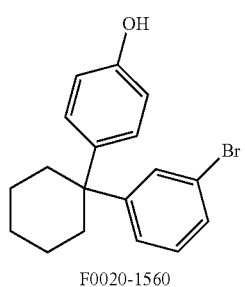

F0020-1560

F0447-0264

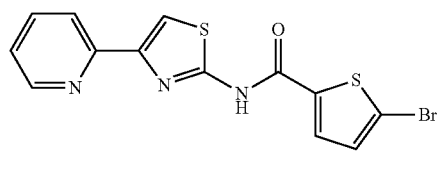

F0447-0273

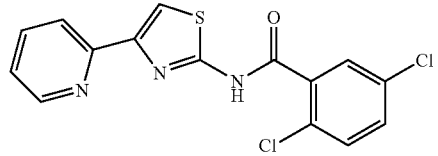

F0447-0277

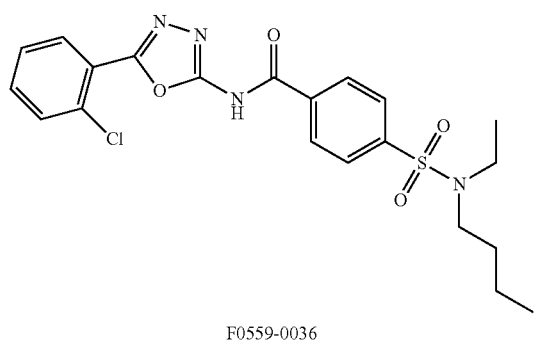

F0559-0036

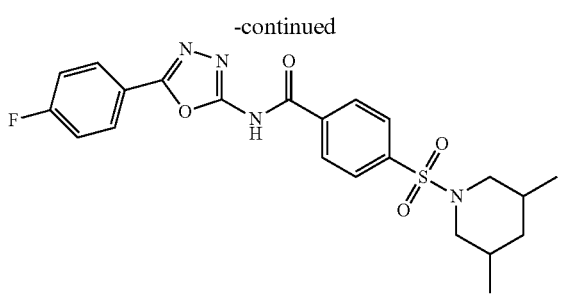

F0559-0106

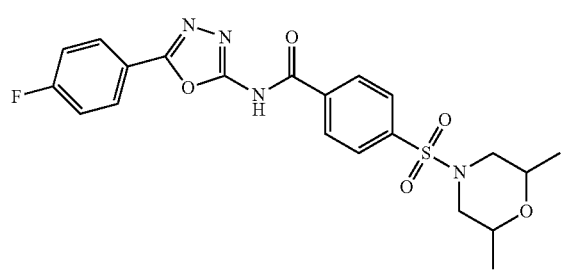

F0559-0107

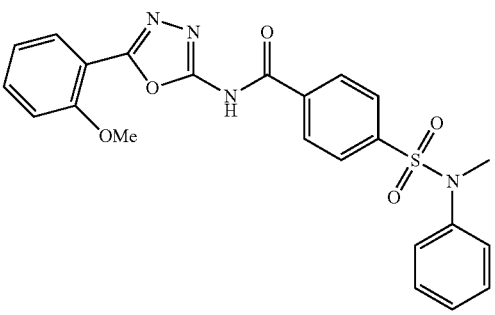

F0559-0127

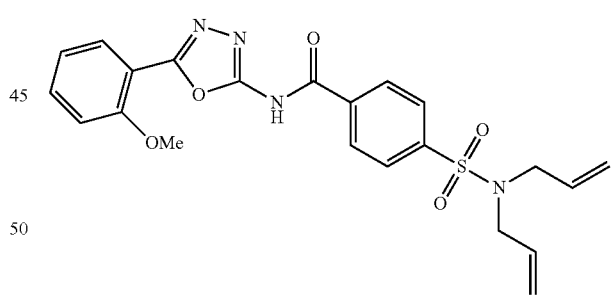

F0559-0129

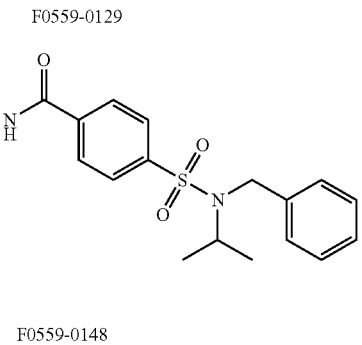

F0559-0148

-continued
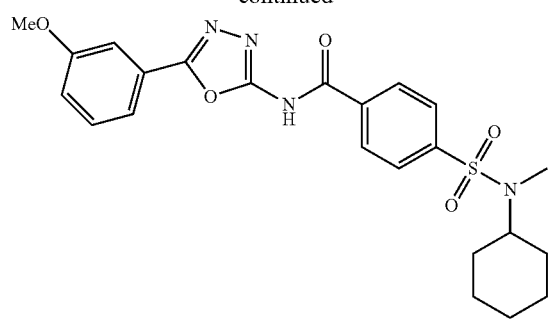
F0559-0158
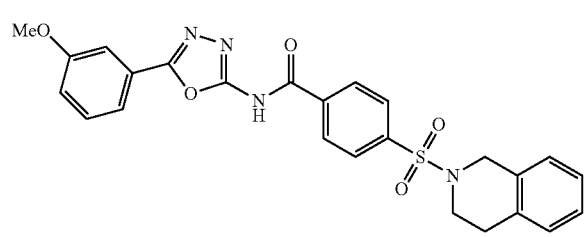
F0559-0171
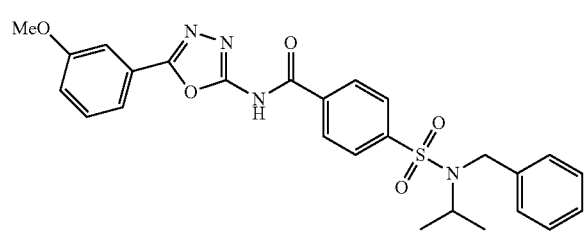
F0559-0178
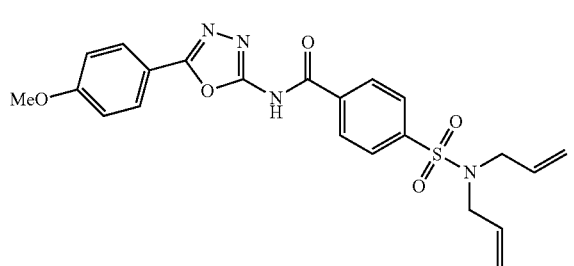
F0559-0189
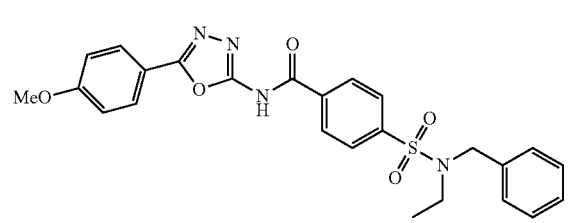
F0559-0206
-continued
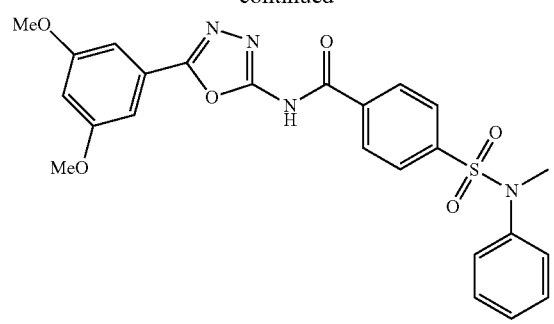
F0559-0246
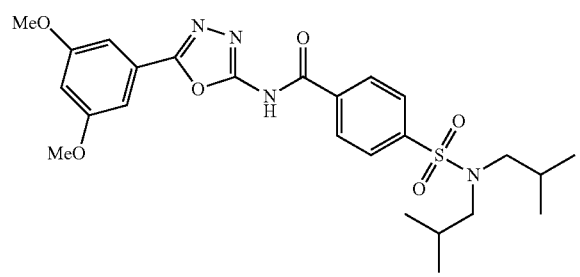
F0559-0264
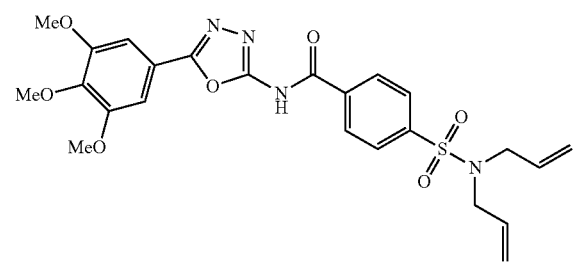
F0559-0279
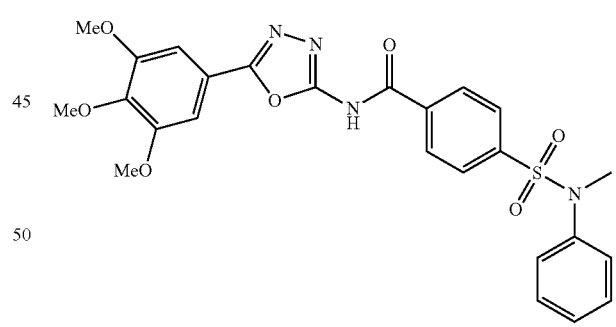
F0559-0307
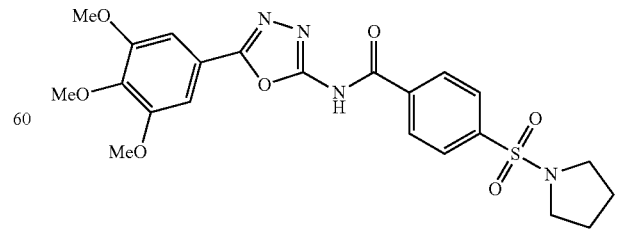
F0559-0311

-continued
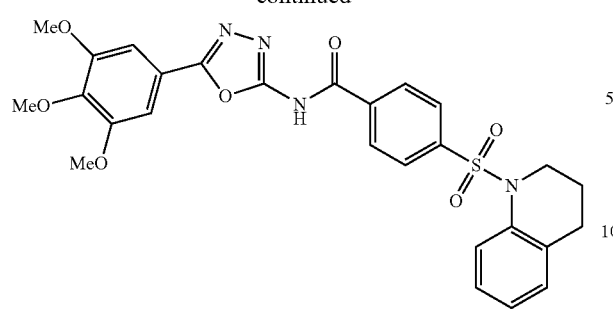
F0559-0320
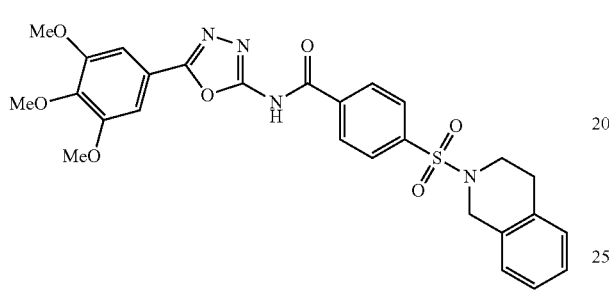
F0559-0321
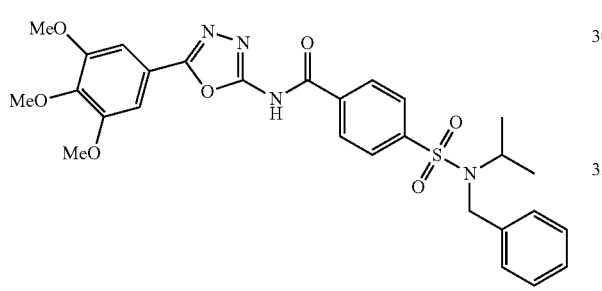
F0559-0328
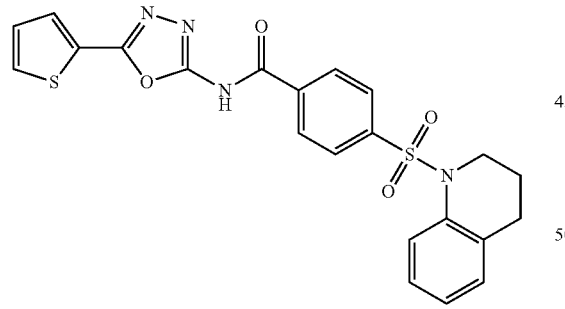
F0559-0350
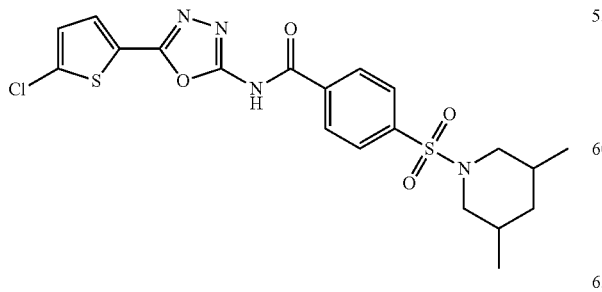
F0559-0376
-continued
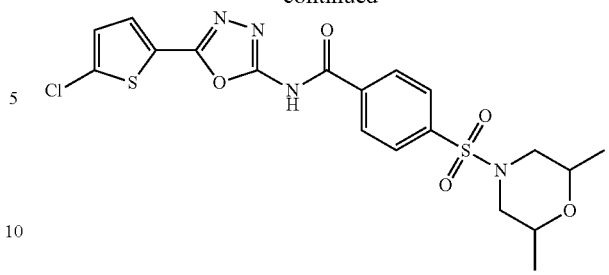
F0559-0377
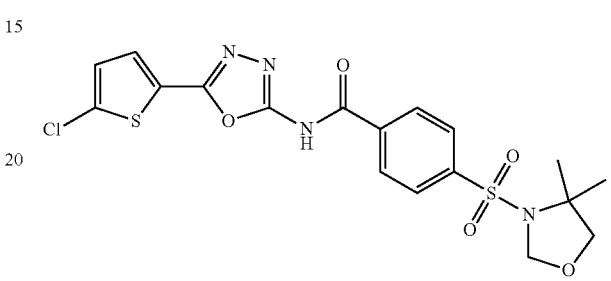
F0559-0390
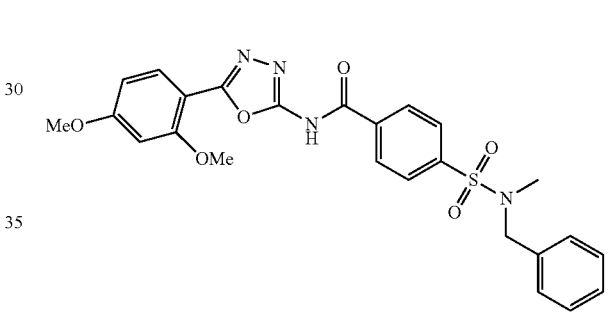
F0559-0398
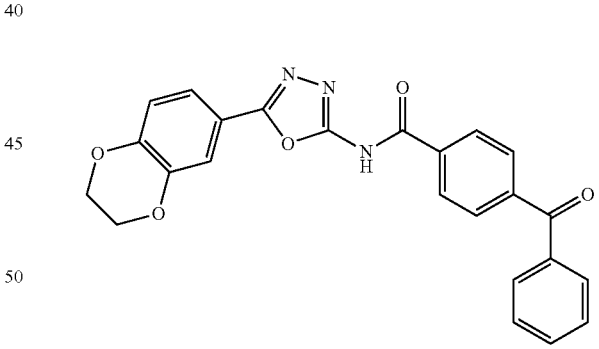
F0608-0019
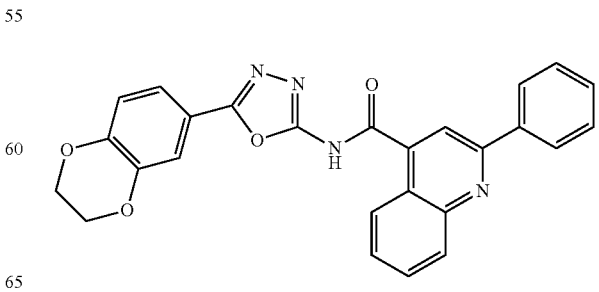
F0608-0046

-continued
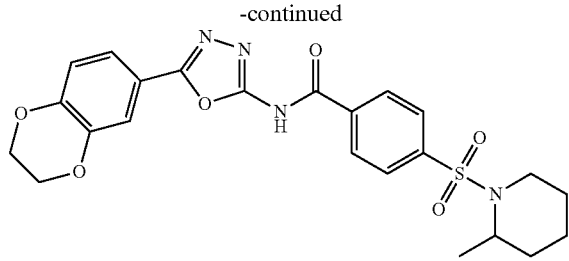
F0608-0071
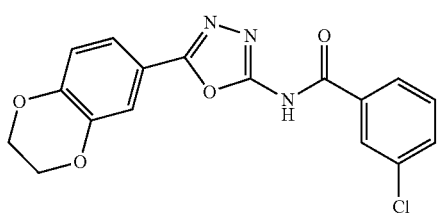
F0608-0123
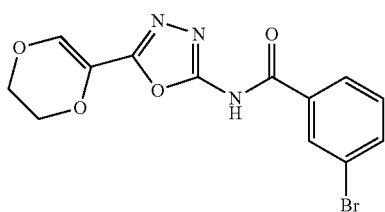
F0608-0146
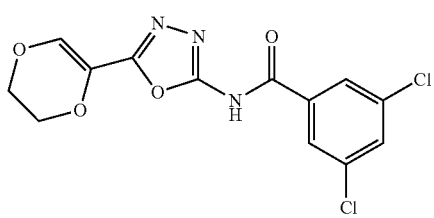
F0608-0258
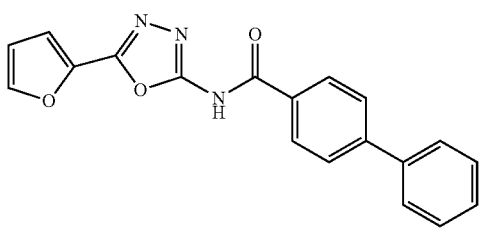
F0608-0410
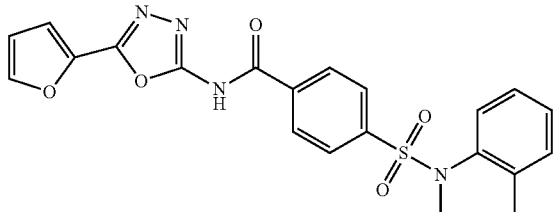
F0608-0447
-continued
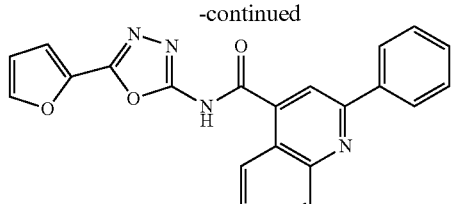
F0608-0448
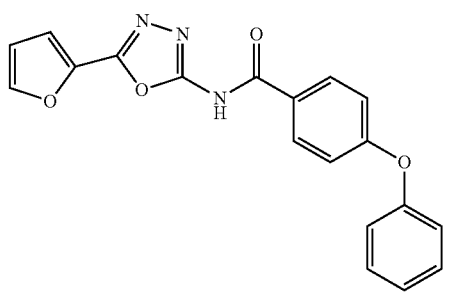
F0608-0491
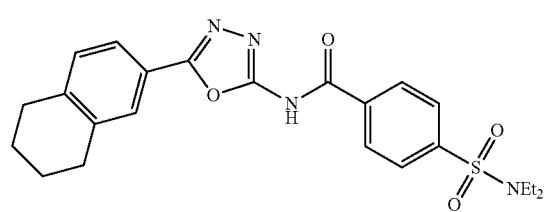
F0608-0543
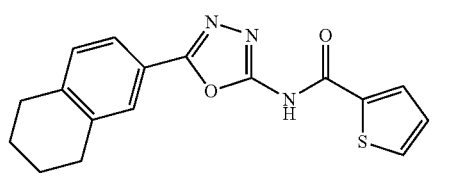
F0608-0554
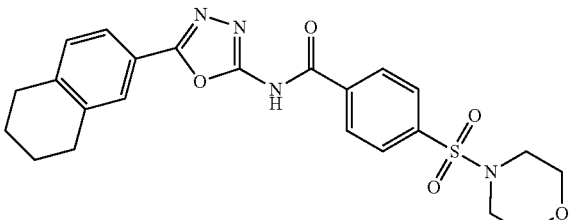
F0608-0560
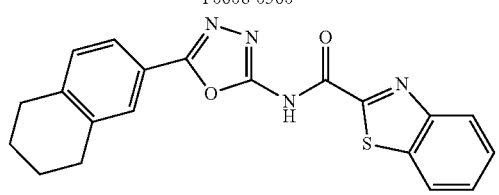
F0608-0570

-continued
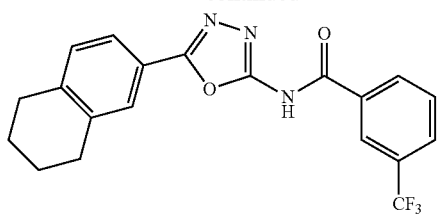
F0608-0575
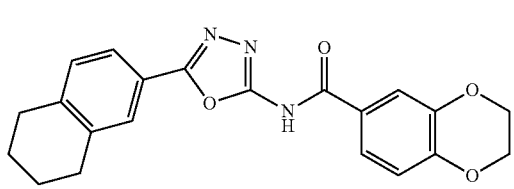
F0608-0601
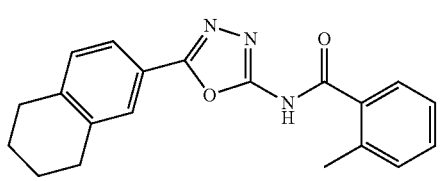
F0608-0614
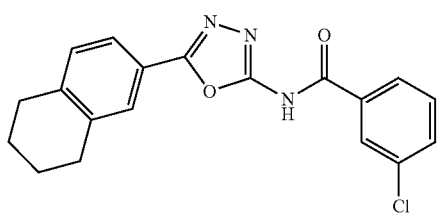
F0608-0659
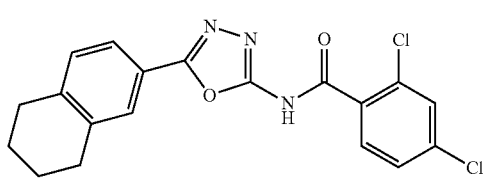
F0608-0661
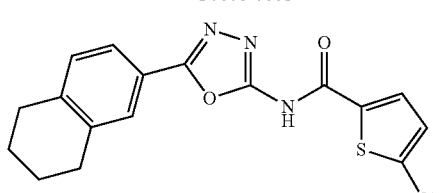
F0608-0662
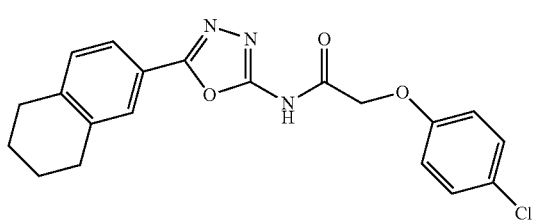
F0608-0664
-continued
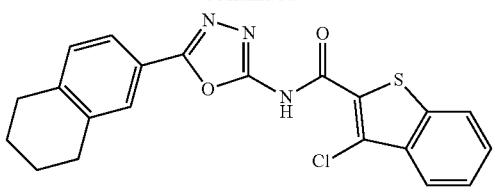
F0608-0665
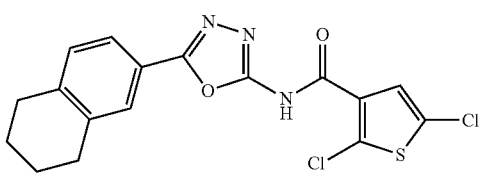
F0608-0668
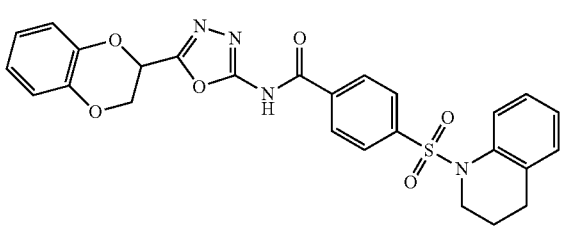
F0608-0715
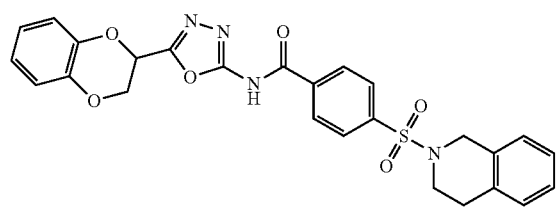
F0608-0728
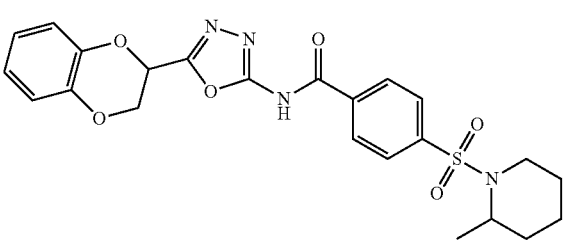
F0608-0741
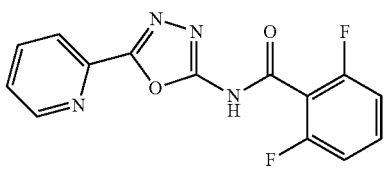
F0608-0895
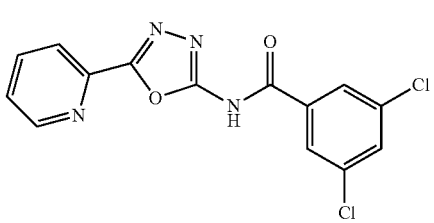
F0608-0928

-continued
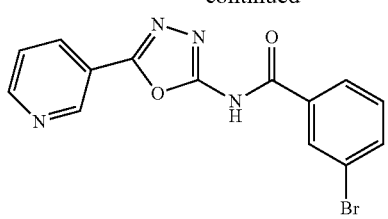
F0608-0950
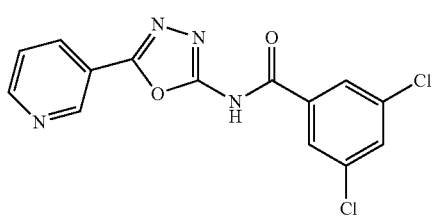
F0608-1062
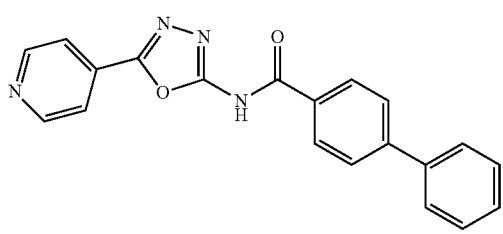
F0608-1080
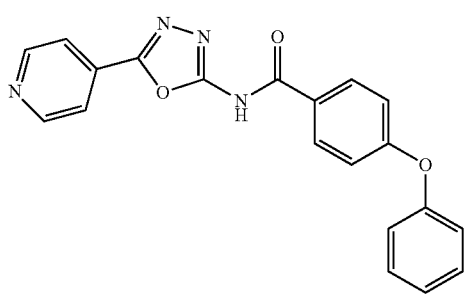
F0608-1161
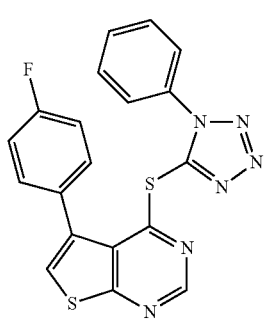
F1142-4245
-continued
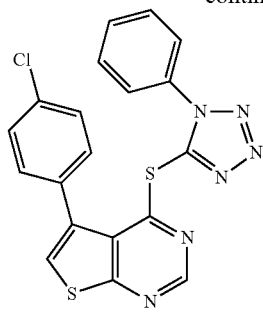
F1142-4597
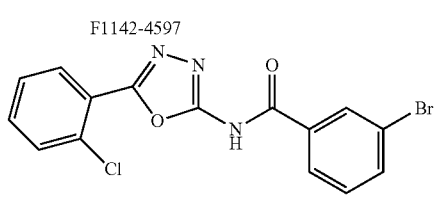
F1374-0014
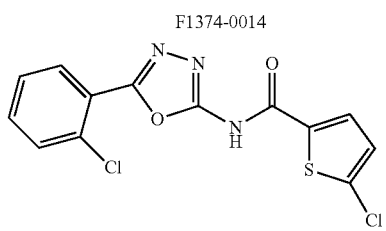
F1374-0036
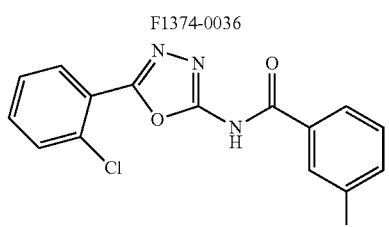
F1374-0037
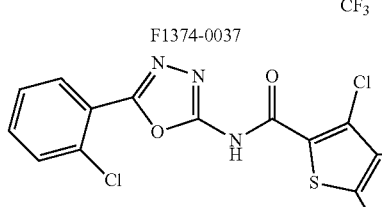
F1374-0043
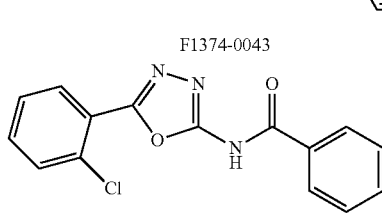
F1374-0055
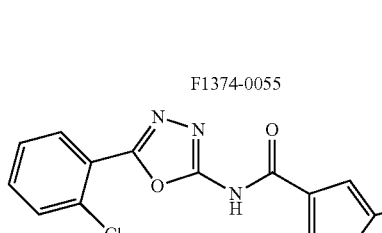
F1374-0058

-continued
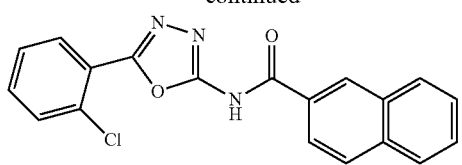
F1374-0082
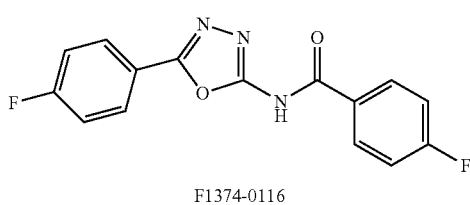
F1374-0116
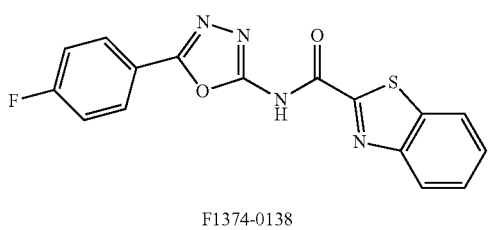
F1374-0138
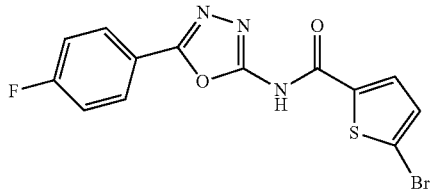
F1374-0140
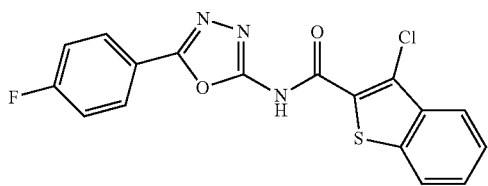
F1374-0148
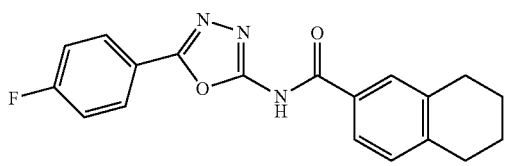
F1374-0172
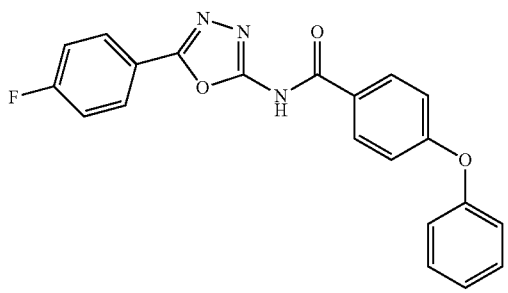
F1374-0188
-continued
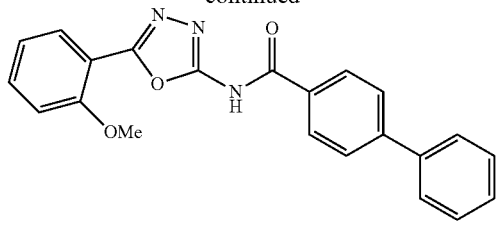
F1374-0220
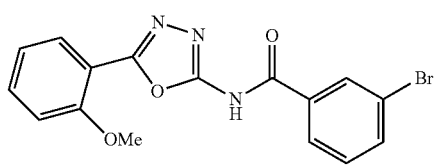
F1374-0224
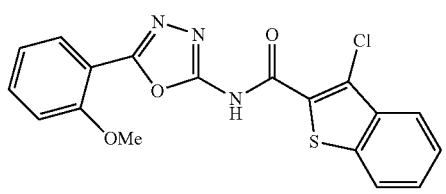
F1374-0253
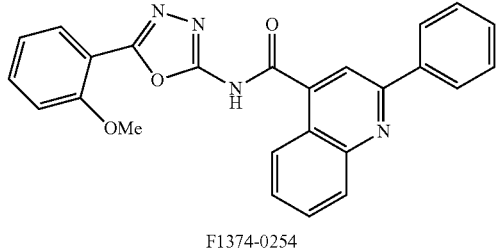
F1374-0254
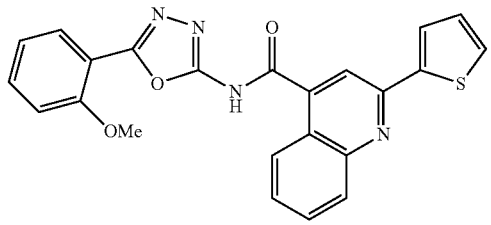
F1374-0255
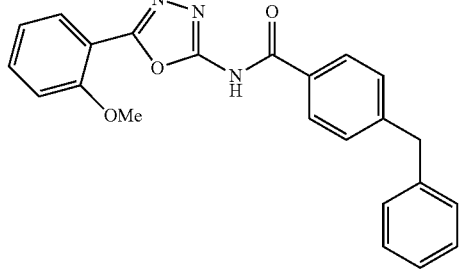
F1374-0276

-continued
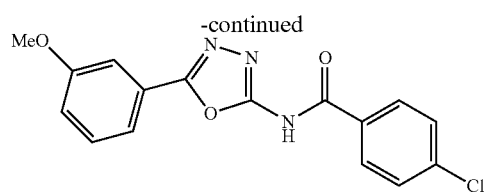
F1374-0320
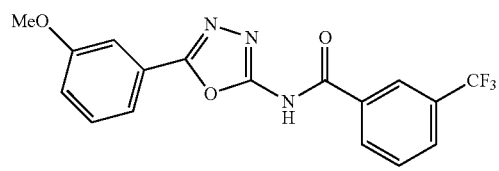
F1374-0352
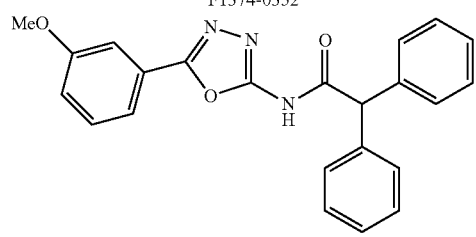
F1374-0379
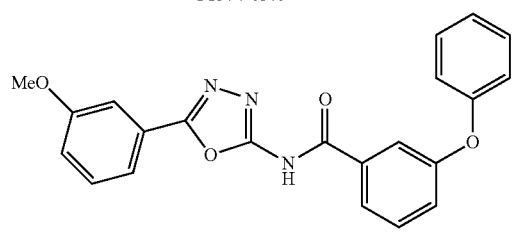
F1374-0396
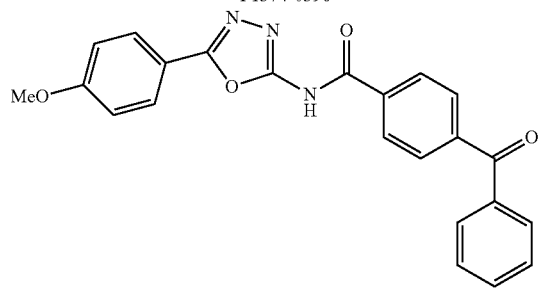
F1374-0443
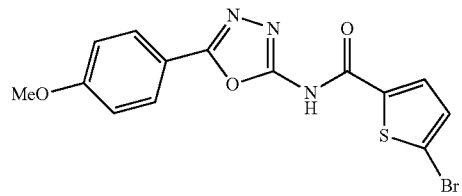
F1374-0455
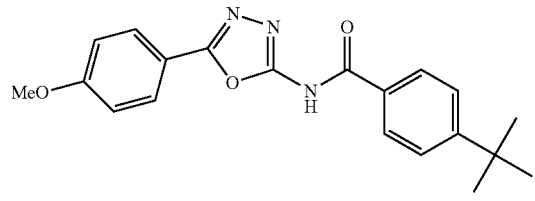
F1374-0495
-continued
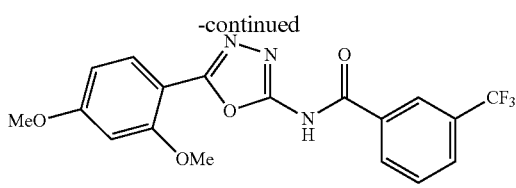
F1374-0562
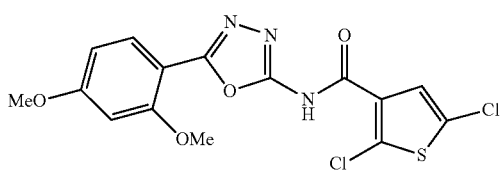
F1374-0583
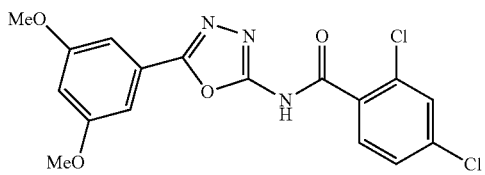
F1374-0651
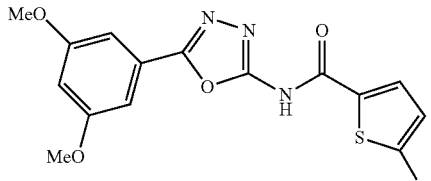
F1374-0666
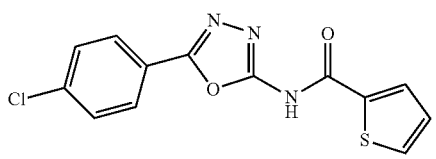
F1374-0757
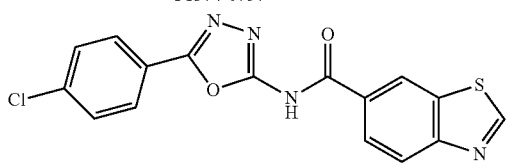
F1374-0836
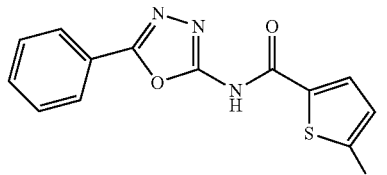
F1374-0875
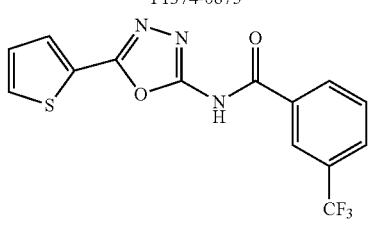
F1374-0982

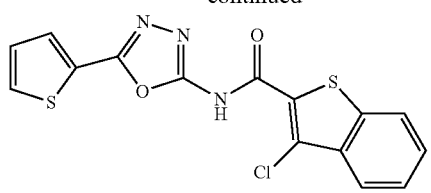
F1374-0988
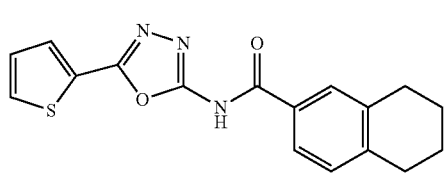
F1374-1012
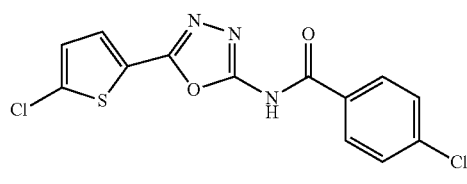
F1374-1055
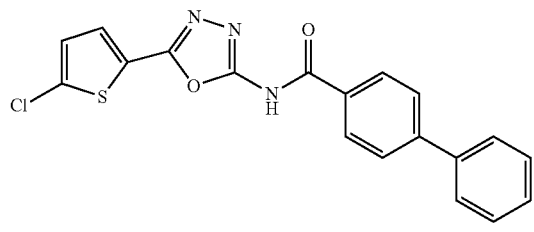
F1374-1060
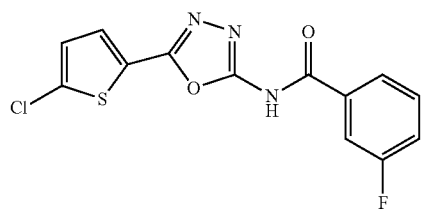
F1374-1062
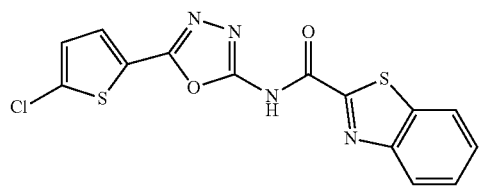
F1374-1083
F1374-1094
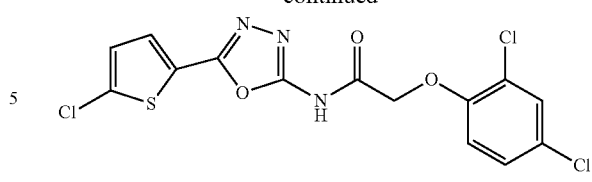
F1374-1102
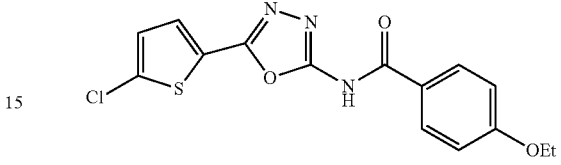
F1374-1129
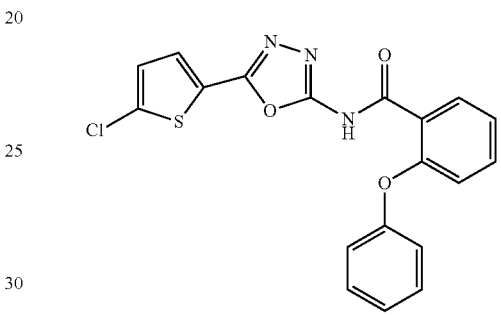
F1374-1149
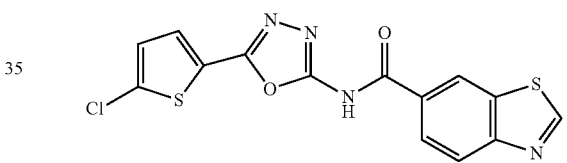
F1374-1151
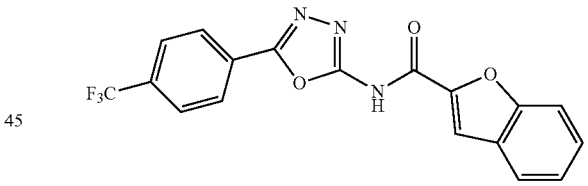
F1374-2134
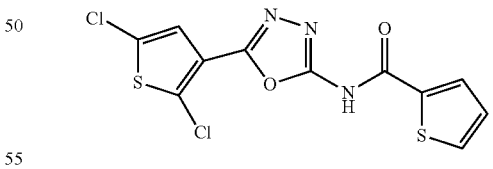
F1374-2664
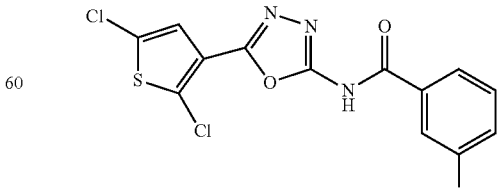
F1374-2671

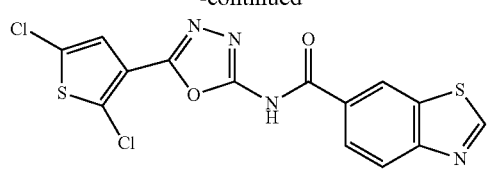
F1374-2676
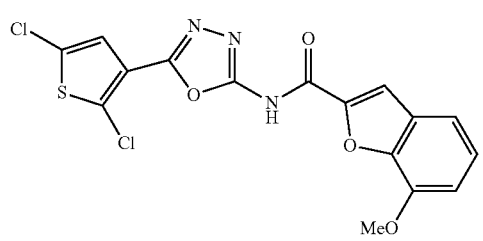
F1374-2680
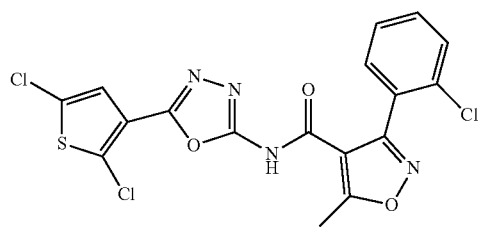
F1374-2706
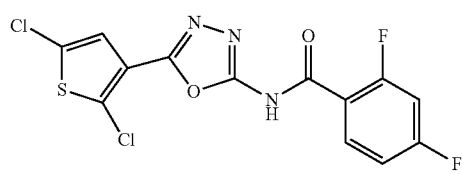
F1374-2707
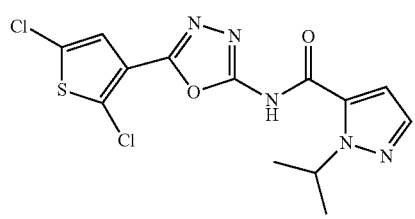
F1374-2902
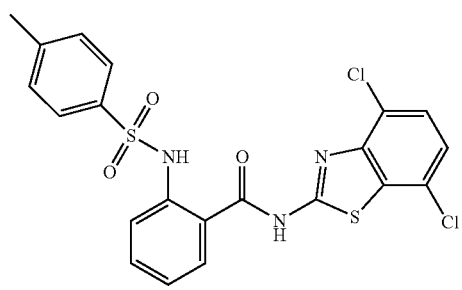
F1813-0710
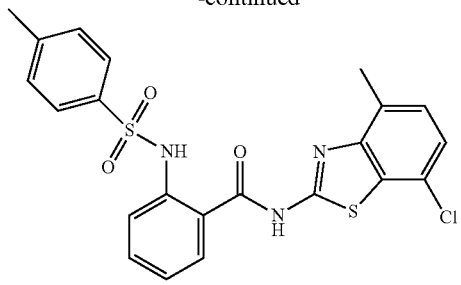
F1813-0711
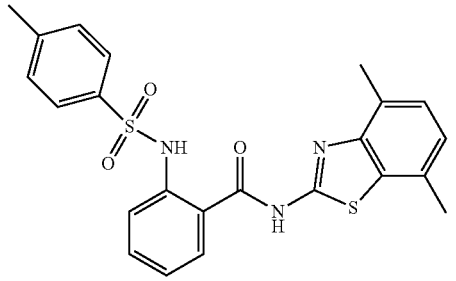
F1813-0712
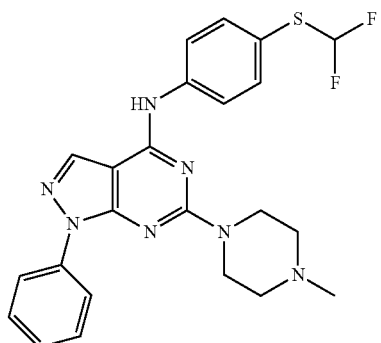
F2090-0579
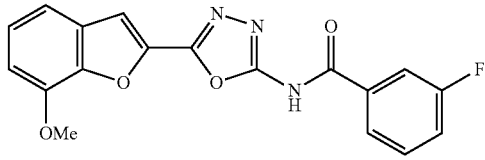
F2273-0013
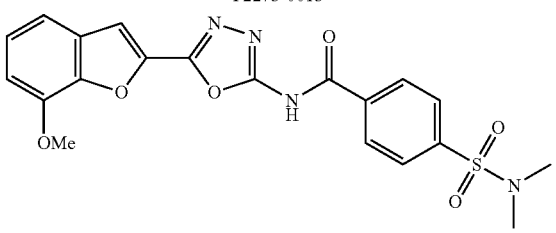
F2273-0029
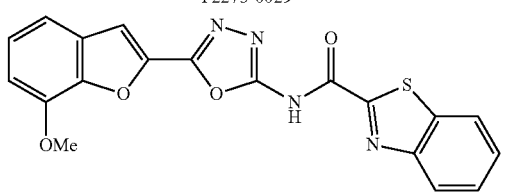
F2273-0037

-continued
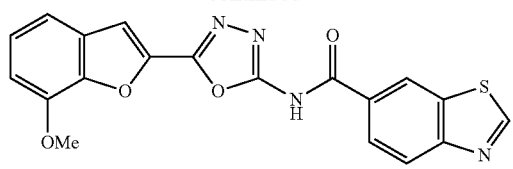
F2273-0114
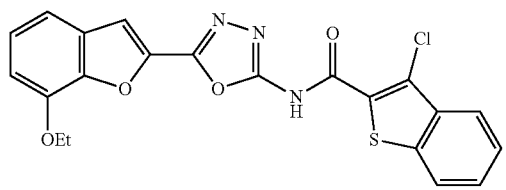
F2273-0238
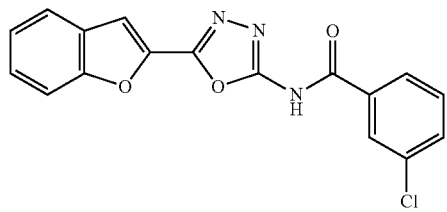
F2273-0385
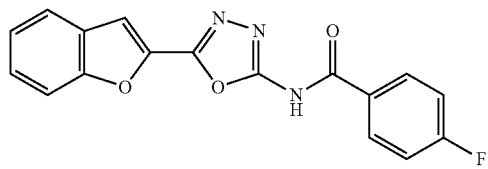
F2273-0390
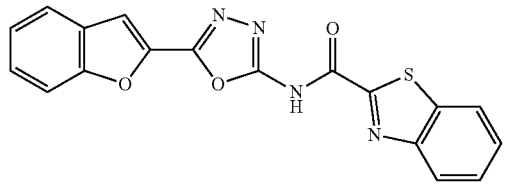
F2273-0415
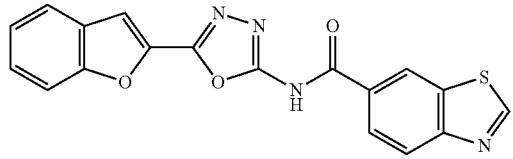
F2273-0492
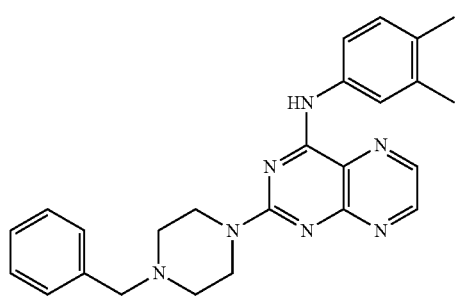
F2359-0308
-continued
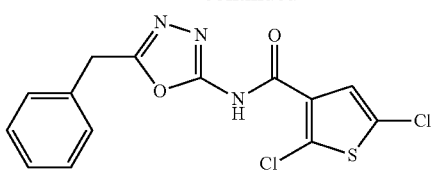
F2368-0063
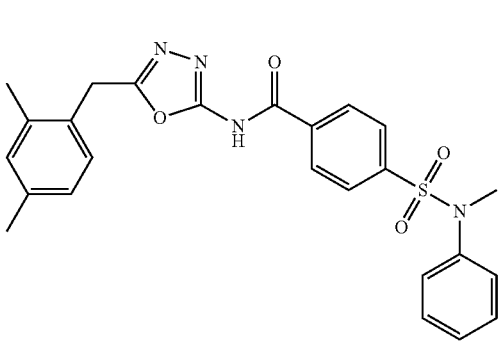
F2368-0431
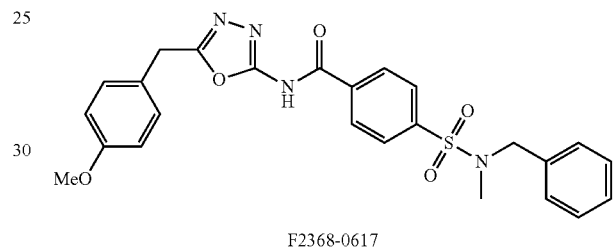
F2368-0617
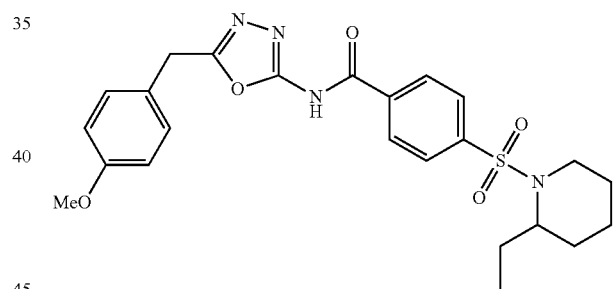
F2368-0619
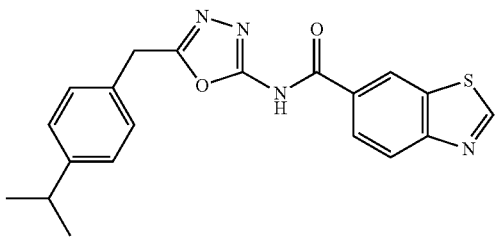
F2368-1143
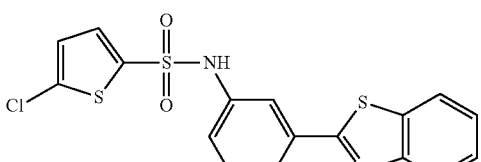
F2399-0063

-continued
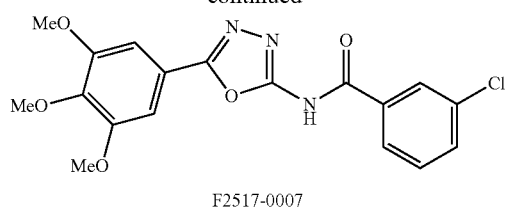
F2517-0007
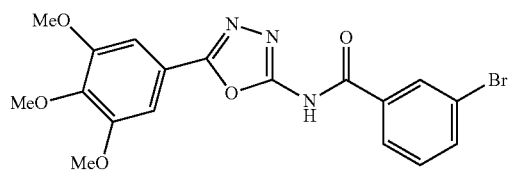
F2517-0014
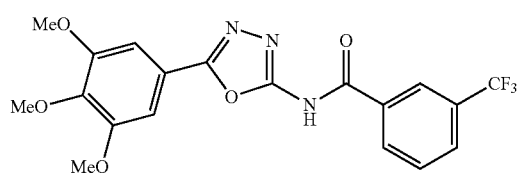
F2517-0037
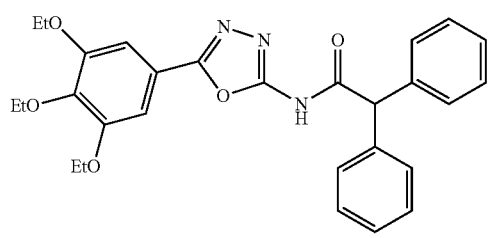
F2517-0165
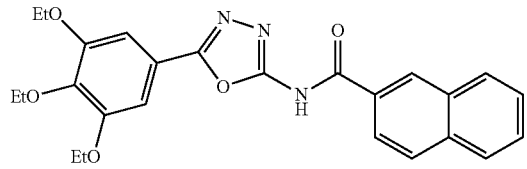
F2517-0182
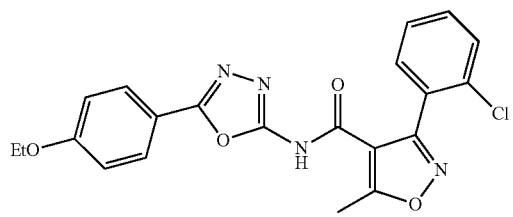
F2517-0329
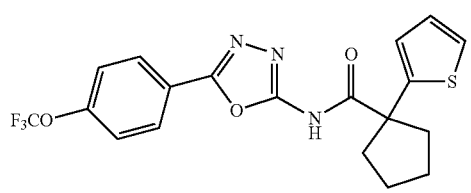
F2517-0863
-continued
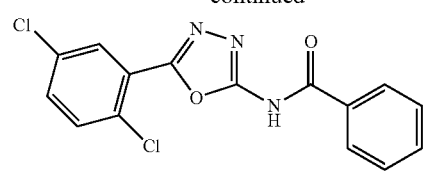
F2518-0002
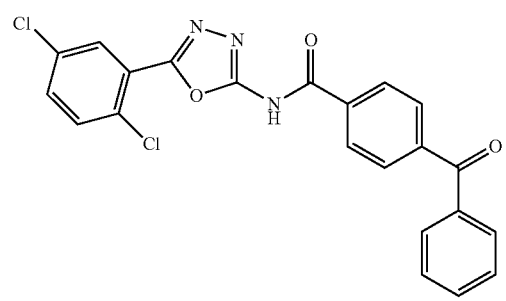
F2518-0024
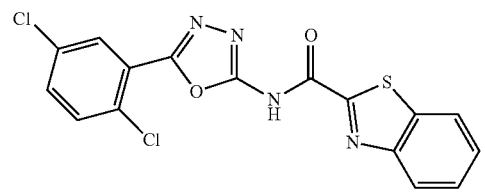
F2518-0039
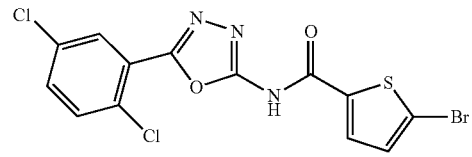
F2518-0041
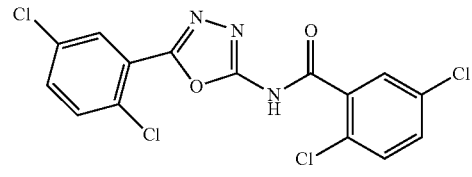
F2518-0049
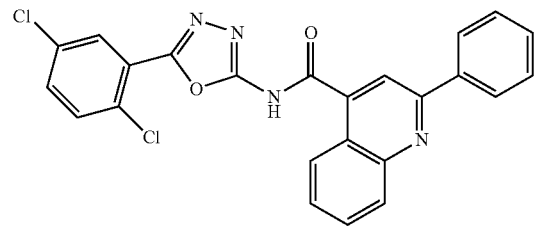
F2518-0055
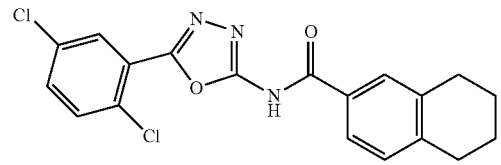
F2518-0085

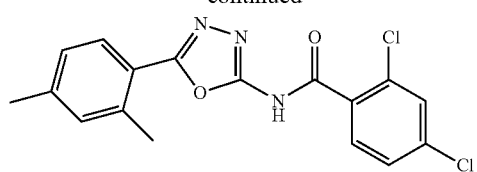
F2518-0166
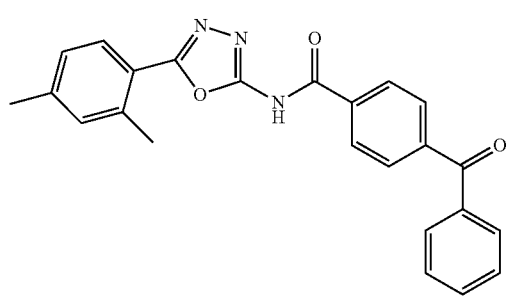
F2518-0168
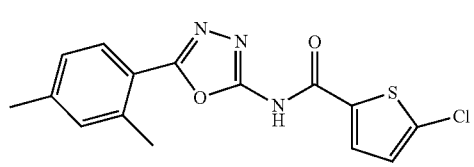
F2518-0186
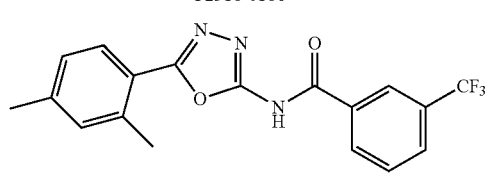
F2518-0189
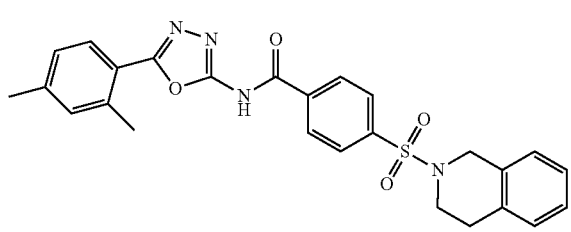
F2518-0213
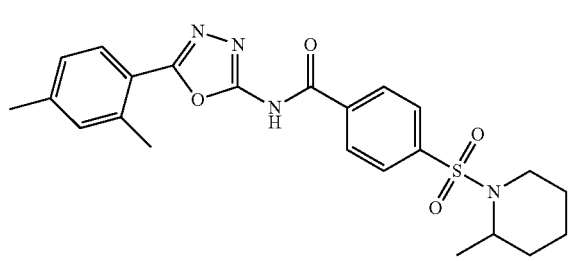
F2518-0228
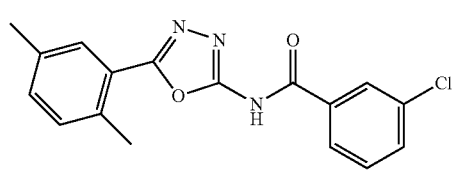
F2518-0295
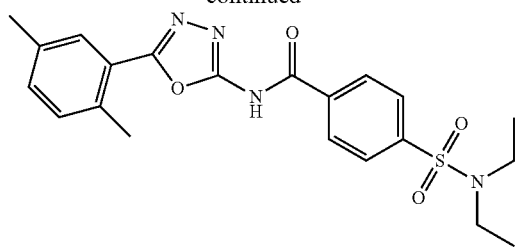
F2518-0298
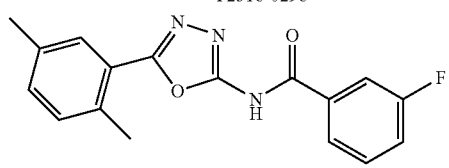
F2518-0301
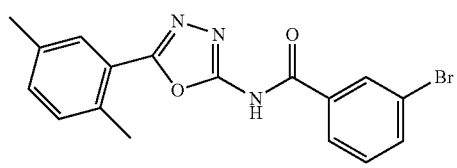
F2518-0303
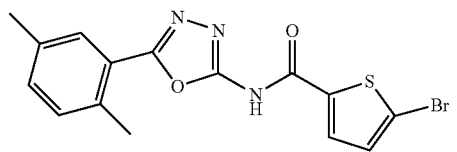
F2518-0329
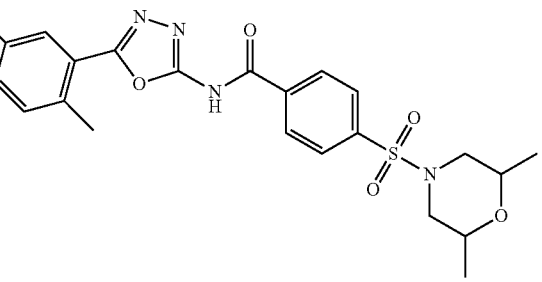
F2518-0334
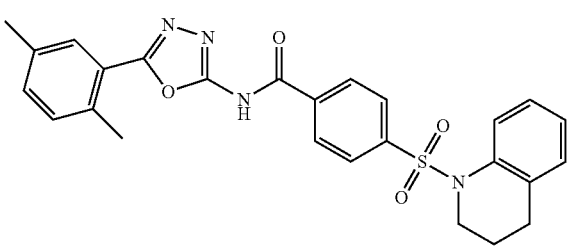
F2518-0342
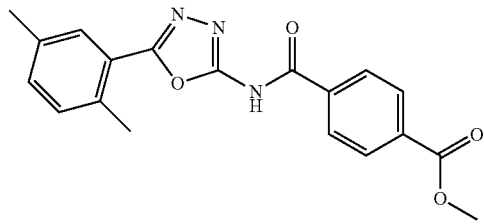
F2518-0355

-continued
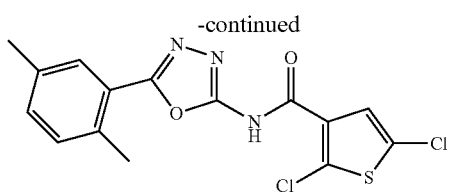
F2518-0360
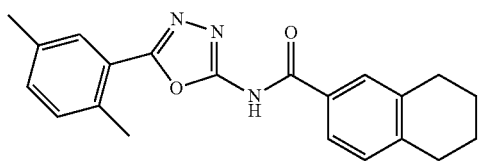
F2518-0373
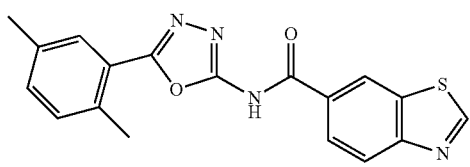
F2518-0414
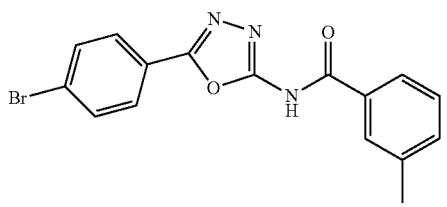
F2518-0436
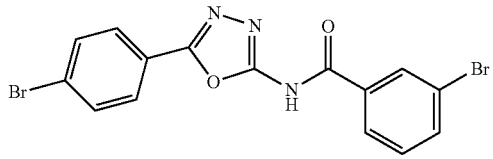
F2518-0447
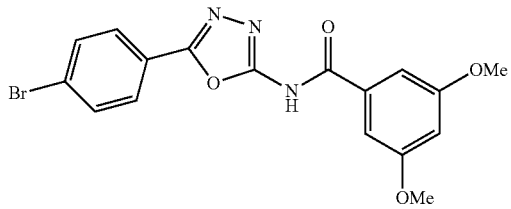
F2518-0451
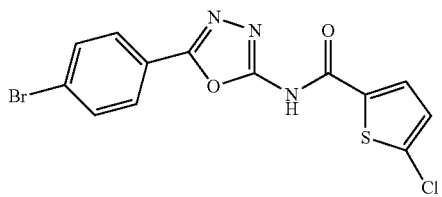
F2518-0474
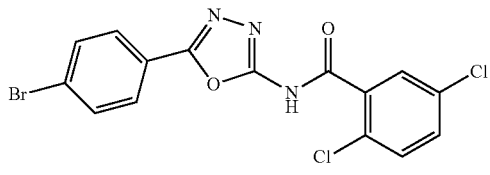
F2518-0481
-continued
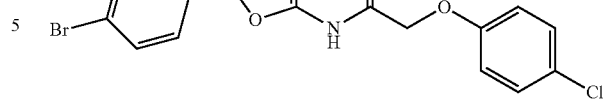
F2518-0483
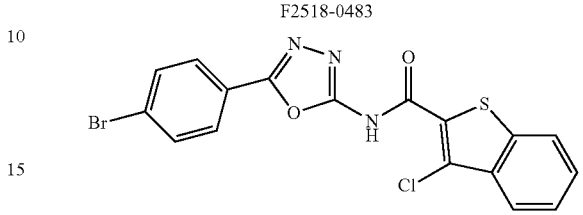
F2518-0484
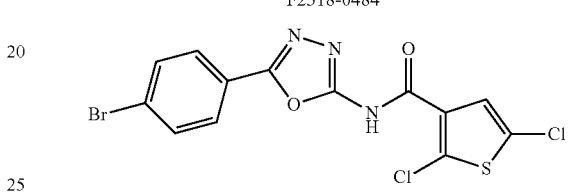
F2518-0504
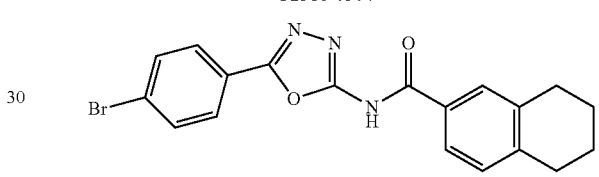
F2518-0517
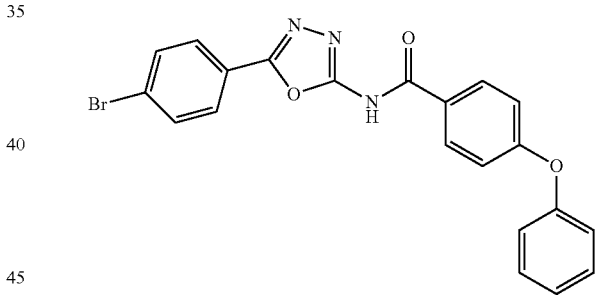
F2518-0534
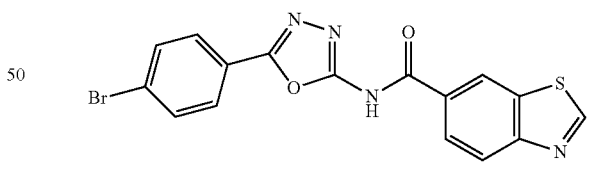
F2518-0558
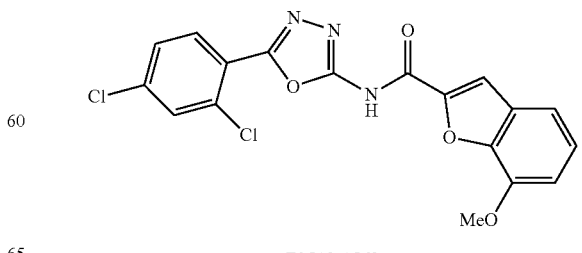
F2518-1563

-continued
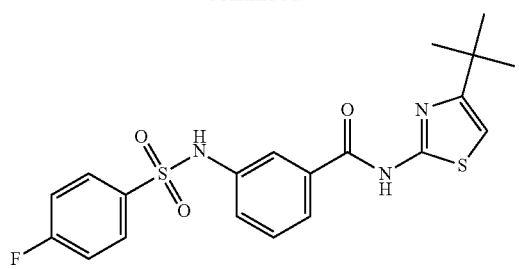
F2619-0556
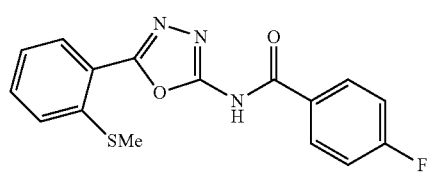
F2645-0012
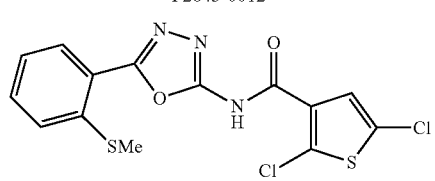
F2645-0067
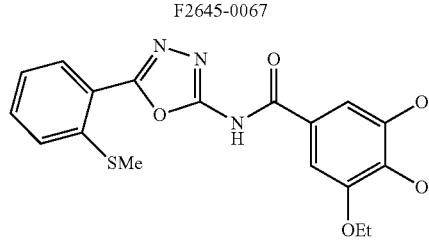
F2645-0099
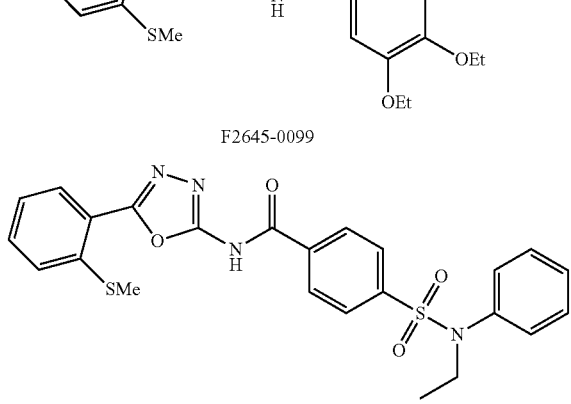
F2645-0115
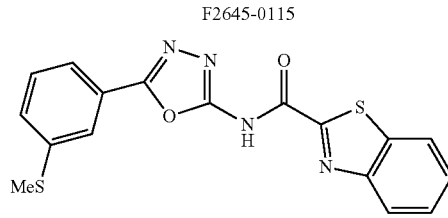
F2645-0188
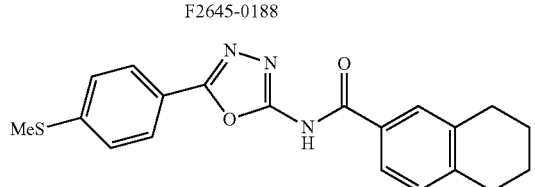
F2645-0379
-continued
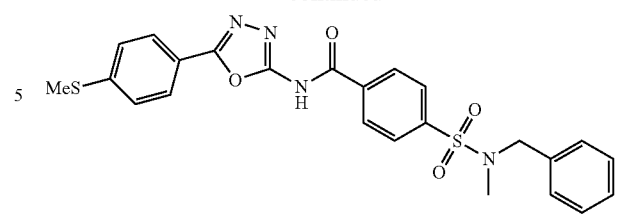
F2645-0405
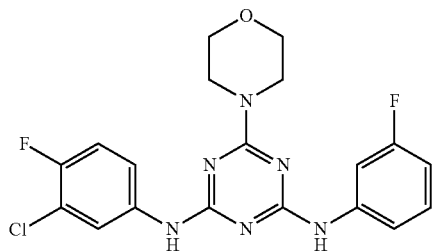
F2703-0396
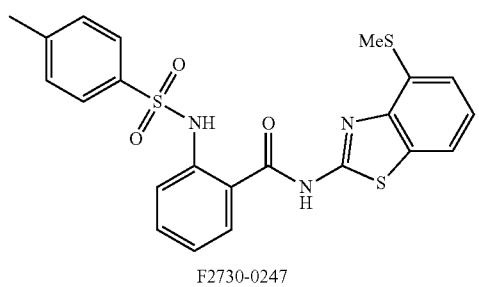
F2730-0247
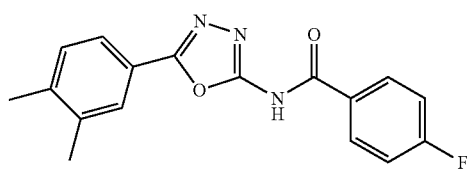
F2767-0012
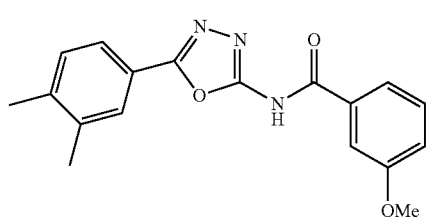
F2767-0017
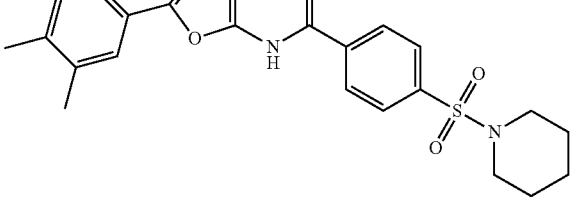
F2767-0026

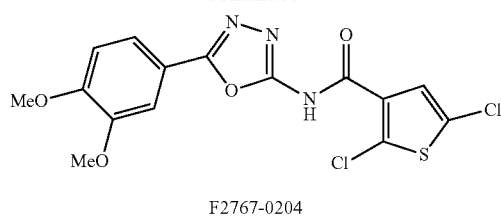
F2767-0204
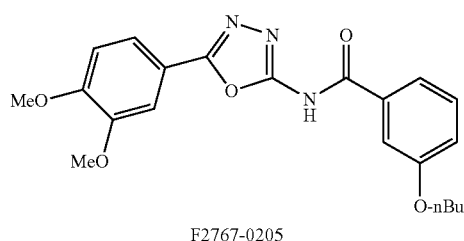
F2767-0205
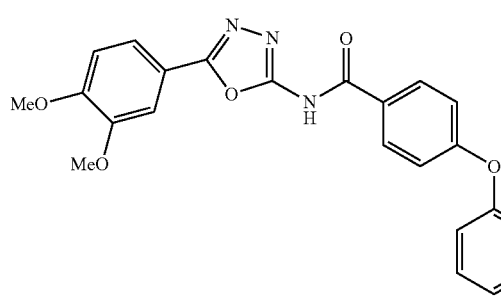
F2767-0223
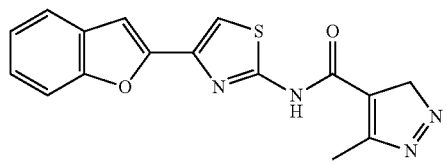
F2962-0176
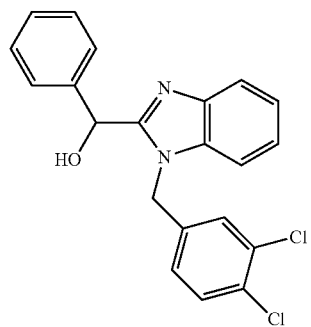
F3068-0037
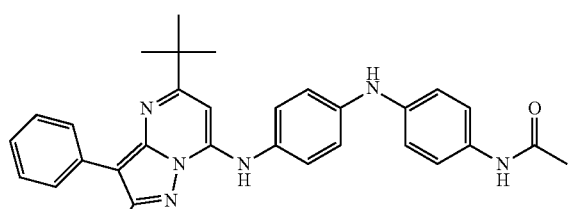
F3348-0030
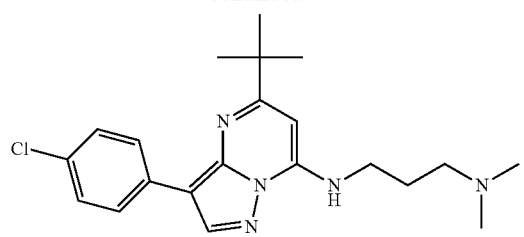
F3348-0373
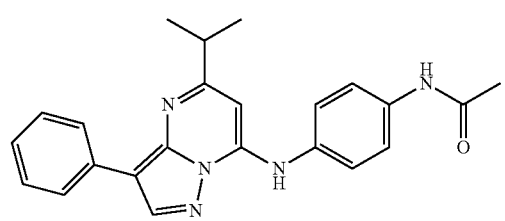
F3348-0533
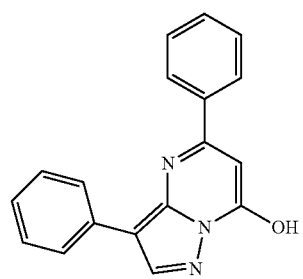
F3348-0667
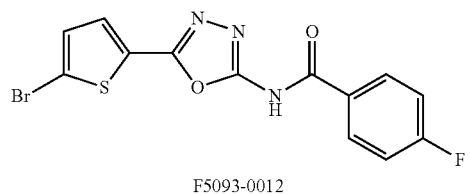
F5093-0012
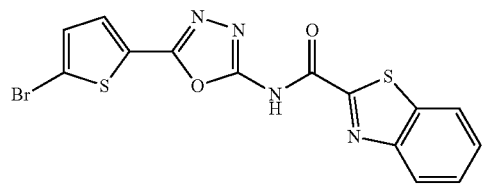
F5093-0037
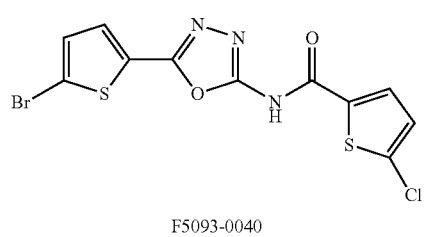
F5093-0040

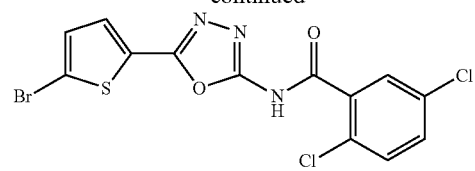

F5093-0046

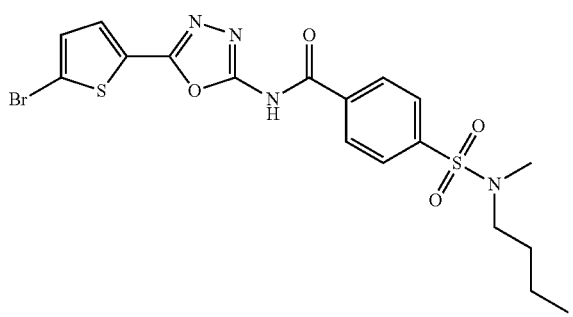

F5093-0101

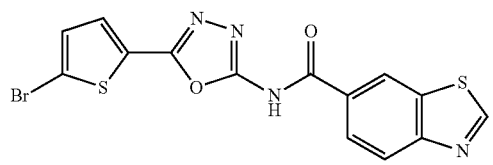

F5093-0111

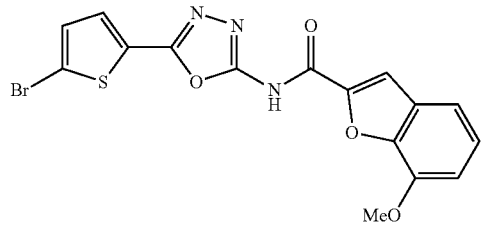

F5093-0196

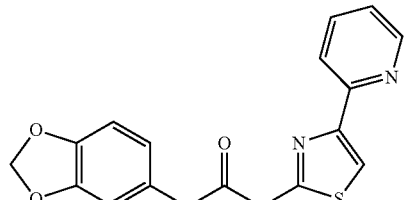

F5772-8284

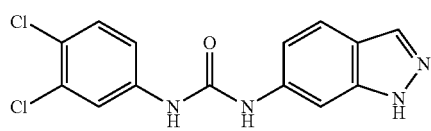

F5882-3050

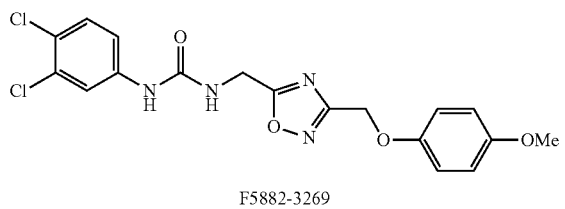

F5882-3269

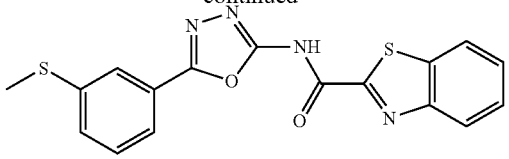

F2645-0188

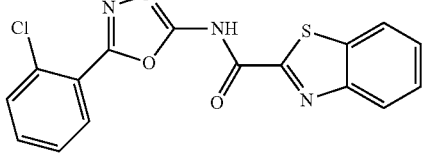

F1374-0033

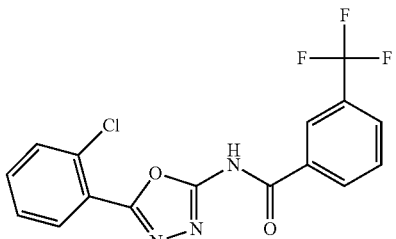

F1374-0037

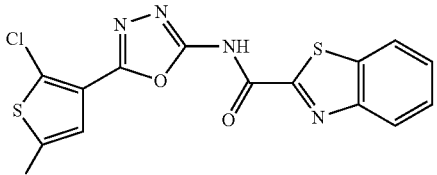

F1374-2739

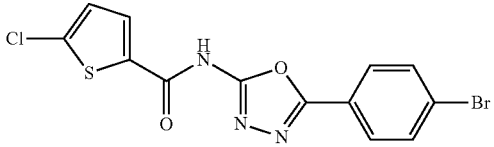

F2518-0474

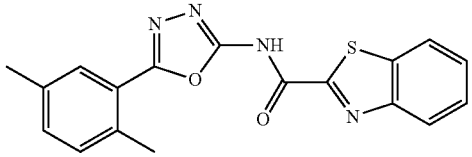

F2518-0327

III. Dosages, Formulations, and Modes of Administration

A variety of methods and compositions are contemplated for inhibiting, preventing, or treating a bacterial infection using one or more antibiotics in combination with an antibiotic potentiator, such as one that inhibits or interferes with expression of the vraSR operon. In particular embodiments, the potentiator is a small molecule compound. Compositions that can be used to inhibit or treat a bacterial infection such as a staphylococcal infection may include one or more of the following substances: a first antibiotic, an antibiotic potentiator, a second antibiotic, a bacterial vaccine, an adjuvant, or a combination thereof. It is contemplated that a solution or composition may have additional components as well, which themselves may or may not be active ingredients. In some embodiments, a composition contains about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or mg/ml or µg/ml of a substance identified above, or a combination of substances or components, or any range derivable therein.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/kg or micrograms/kg/minute or mg/kg/min or micrograms/kg/hour or mg/kg/hour, or any range derivable therein, of a compound, such as a first antibiotic, an antibiotic potentiator, a second antibiotic, a bacterial vaccine, an adjuvant, or a combination thereof. Additionally, a subject may be administered a solution or composition that is described in the previous paragraph.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced. Moreover, a dose of one compound such as the antibiotic may be delivered prior to, concurrently with, and/or after an antibiotic potentiator. In certain embodiments where the first antibiotic, an antibiotic potentiator, a second antibiotic, a bacterial vaccine, and/or an adjuvant are administered with respect to at least one dose separately and/or at different times to a subject the intervening time between is or is about 10, 20, 30, 40, 50, minutes (or any range derivable therein) and/or 1, 2, 3, 4, 5, 6, 7, 8, 9, 10, 11, 12 hours (or any range derivable therein) or 1, 2, 3, 4, or 5 days (or any range derivable therein). In certain embodiments, an antibiotic is given with or before the antibiotic potentiator, such as about or up to about or at most about 1, 2, 3, 4, 5, 6, 7, 8, 9, 10, 15, 20, 25, 30, 35, 40, 45, 50, 55, 60, 70, 80, 90, 100, 110, 120, 130, 140, 150, 160, 170, or 180 minutes (or any range derivable therein) before the antibiotic potentiator.

An antibiotic may be administered for example, by any one of the following routes of administration: parenteral, intravenously, topically, intraocular, intranasal, rectal, vaginal, subcutaneous, intramuscular, arterial, sublingual, transmucosal, transdermal, or oral administration.

The antibiotic compositions may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In an embodiment, the antibiotic product is formulated in a manner such that it is suitable for oral administration.

For example, in formulating the antibiotic product for topical administration, such as by application to the skin, the at least two different dosage forms, each of which contains an antibiotic, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the embodiments to provide an antibiotic product in the form of a patch, which includes antibiotic dosage forms having different release profiles, as hereinabove described.

In addition, the antibiotic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antibiotic with different release profiles may be formulated for rectal or vaginal administration, as known in the art. This may take the form of a cream or emulsion, or other dissolvable dosage form similar to those used for topical administration.

As a further embodiment, the antibiotic product may be formulated for use in inhalation therapy by coating the particles and micronizing the particles for inhalation.

In some embodiments, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is an immediate release tablet, and may also include two or more additional tablets, each of which provides for a delayed release of the antibiotic.

The formulation of an antibiotic product including at least three dosage forms with different release profiles for different routes of administration is deemed to be within the skill of the art from the teachings herein. As known in the art, with respect to delayed release, the time of release can be controlled by the concentration of antibiotics in the coating and/or the thickness of the coating.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons. It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above. These materials may be present in the rate of 0.05-15% (W/W).

In certain embodiments there is a delayed release component. The components in this composition are the same immediate release unit, but with additional polymers integrated into the composition, or as coatings over the pellet or granule.

Materials that can be used to obtain a delay in release suitable for this component of the embodiment can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5-25% (W/W) of this component.

As an enteric release composition the components are the same as the immediate release component, but with additional polymers integrated into the composition, or as coatings over the pellet or granule.

The kind of materials useful for this purpose can be, but are not limited to, cellulose acetate phthalate, Eudragit L, and other phthalate salts of cellulose derivatives. These materials can be present in concentrations from 4-20% (W/W).

Pharmaceutical Compositions and Kits

Suitable preparations, e.g., substantially pure preparations of the agents described herein may be combined with pharmaceutically acceptable carriers, diluents, solvents, excipients, etc., to produce an appropriate pharmaceutical composition. The embodiment therefore provides a variety of pharmaceutically acceptable compositions for administration to a subject comprising (i) an antibiotic potentiating agent; and (ii) a pharmaceutically acceptable carrier or excipient. The embodiment further provides a pharmaceutically acceptable composition comprising (i) an antibiotic potentiating agent; (ii) an antibiotic whose activity is potentiated by the compound; and (iii) a pharmaceutically acceptable carrier or excipient. The embodiment further provides a pharmaceutically acceptable unit dosage form containing a predetermined amount of an antibiotic and a predetermined amount of an antibiotic potentiating agent, wherein the predetermined amounts are selected so that the antibiotic potentiating agent potentiates the antibiotic when the unit dosage form is administered to a subject.

Further provided are pharmaceutically acceptable compositions comprising a pharmaceutically acceptable derivative (e.g., a prodrug) of any of the potentiating agents of the embodiments, by which is meant any non-toxic salt, ester, salt of an ester or other derivative of a potentiating agent, upon administration to a recipient, is capable of providing, either directly or indirectly, the potentiating agent. A wide variety of appropriate pharmaceutically acceptable salts are well known in the art. For example, S. M. Berge et al., describe pharmaceutically acceptable salts in detail in J. Pharmaceutical Sciences, 66:1, 1977, incorporated herein by reference. Pharmaceutically acceptable salts of the compounds of this embodiment include those derived from suitable inorganic and organic acids and bases.

The term "pharmaceutically acceptable carrier, excipient, or vehicle" refers to a non-toxic carrier, excipient, or vehicle that does not destroy the pharmacological activity of the agent with which it is formulated. Pharmaceutically acceptable carriers, excipients, or vehicles that may be used in the compositions of this embodiment include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

Pharmaceutically acceptable salts of the agents of this embodiment include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the embodiment and their pharmaceutically acceptable acid addition salts.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2 ethanedisulfonic acid, 2 hydroxyethanesulfonic acid, 2 naphthalenesulfonic acid, 3 phenylpropionic acid, 4,4' methylenebis(3 hydroxy 2 ene-1 carboxylic acid), 4 methylbicyclo[2.2.2]oct 2 ene-1 carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o (4 hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., Verlag Helvetica Chimica Acta, 2002).

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis hydroxynaphthoate, gentisates, isethionates, di p toluoyltartrates, methane-sulfonates, ethanesulfonates, benzenesulfonates, p toluenesulfonates, cyclohexyl-sulfamates, quinates, esters of amino acids, and the like. Similarly, a compound comprising an amine group may be administered as an amide that is converted by hydrolysis in vivo to the amine compound.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In all cases, the composition should be sterile, if possible, and should be fluid to the extent that easy syringability exists.

Pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol or sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present embodiment also contemplates delivery of compositions using a nasal spray.

For topical applications, the pharmaceutically acceptable compositions may be formulated in a suitable ointment containing the active component suspended or dissolved in one or more carriers. Carriers for topical administration of the compounds of this embodiment include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For local delivery to the eye, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments. It will be appreciated that a range of different dosage combinations (i.e., doses of the antibiotic and antibiotic potentiating agent) can be used.

Exemplary doses include milligram or microgram amounts of the inventive compounds per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) For local administration (e.g., intranasal), doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

The presented embodiments also include pharmaceutical packs or kits comprising one or more containers (e.g., vials, ampoules, test tubes, flasks, or bottles) containing one or more ingredients of the inventive pharmaceutical compositions, for example, allowing for the simultaneous or sequential administration of the antibiotic potentiating agent and antibiotic agent(s) it potentiates. Optionally associated with such container(s) can be a notice in the form prescribed by a governmental agency regulating the manufacture, use or sale of pharmaceutical products, which notice reflects approval by the agency of manufacture, use or sale for human administration. Different ingredients may be supplied in solid (e.g., lyophilized) or liquid form. Each ingredient will generally be suitable as aliquoted in its respective container or provided in a concentrated form. Kits may also include media for the reconstitution of lyophilized ingredients. The individual containers of the kit are preferably maintained in close confinement for commercial sale.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Examples of pharmaceutically acceptable salts derived from appropriate bases include alkali metal, alkaline earth metal, ammonium and N+(C1-4 alkyl)4 salts.

Representative pharmaceutically acceptable alkali or alkaline earth metal salts include sodium, lithium, potassium, calcium, magnesium, and the like.

Further pharmaceutically acceptable salts include, when appropriate, nontoxic ammonium, quaternary ammonium, and amine cations, for example formed using counterions such as halide, hydroxide, carboxylate, sulfate, phosphate, nitrate, lower alkyl sulfonate and aryl sulfonate.

Physiologically acceptable carrier or excipient: As used herein, the term "physiologically acceptable carrier or excipient" refers to a carrier medium or excipient which does not interfere with the effectiveness of the biological activity of the active ingredients and which is not excessively toxic to the host at the concentrations at which it is administered. The term includes solvents, dispersion media, coatings, antibacterial and antifungal agents, isotonic agents, absorption delaying agents, and the like. The use of such media and agents for the formulation of pharmaceutically active substances is well-known in the art (see, for example, "Remington's Pharmaceutical Sciences", E. W. Martin, 18th Ed., 1990, Mack Publishing Co.: Easton, Pa., which is incorporated herein by reference in its entirety).

IV. Examples

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Test Strain Construction—

The test strain (923) is a USA300 MRSA clinical isolate for which the dependence of Mc resistance on vraSR has been well characterized (1, 2). To produce a reporter for vra operon transcription, the vra promoter ($P_{vra}$) was PCR amplified from strain 923 using primers $P_{vra}$-F (5'-aaa gaattctgaaggtatggtattagctattg-3'(SEQ ID NO:1)) and ($P_{vra}$-R) (5'-aaaggatccgttgatgtcgatgatatgtttg-3'(SEQ ID NO: 2)) containing EcoRI and BamHI restriction sites (underlined) and inserted into pXen-1 (Caliper Life Sciences) in the compatible restriction sites present upstream of the luxAB-CDE operon (lux) from *Photorhabdus luminescens*. This gene cluster (lux) produces all the components required for luminescence obviating the need for exogenous substrate (3). The ligation was transformed into *E coli* strain TOP10 (Invitrogen) and colonies were selected on ampicillin (100 µg/ml). The resulting plasmid was isolated and called pPvra::lux. With this construct, the $P_{vra}$ drives expression of the lux gene cluster. $pP_{vra}$::lux was transformed into the restriction negative intermediate *Staphylococcus aureus* host strain, RN4220 (Kreiswirth) and was then isolated from RN4220 and transformed into MRSA strain 923 (923 $pP_{vra}$-lux). The vra promoter and lux genes were confirmed as wild-type by Sanger sequence analysis. Strains containing $pP_{vra}$-lux were cultured in the presence of chloramphenicol (Cm) to maintain the plasmid.

Validation of Test Strain 923 $pP_{vra}$::lux—

The optimal concentration of oxacillin for vra induction and luminescence was chosen by preliminary testing of a range of oxacillin concentrations (FIG. 1). Briefly, a saturated overnight culture of the test strain (923 $pP_{vra}$-lux) in TSB (containing 10 µg/ml chloramphenicol for plasmid selection) was diluted 1:100 into fresh TSB containing 0 to 6 µg/mL of oxacillin. A 100 µL cell plus oxacillin suspension was applied to each well of a white plastic clear-bottomed 96-well plate (Costar) and the plate was incubated at 37° C. Absorbance at 600 nm and luminescence were monitored every 5 minutes for 24 hours using a microplate reader (Fluostar Optima, BMG).

Small-Molecule Screening—

The Life Chemicals Library was used for the small molecule library. The Life Chemicals Library used in the screen contains approximately 25,000 drugs with history of use in humans, with the greatest possible degree of "drug-likeliness". It was supplied in 384 well format in 10 mM concentration in DMSO and was re-plated to a 96 well daughter plates to a 1 mM concentration. This antimicrobial-focused chemical library consisting of 25,000 compounds with drug-like properties was built specifically by the inventors for high-throughput screening against antimicrobial drug targets. To this end, 18,750 compounds were selected from the antibacterial and antimicrobial Life Chemicals (LC) libraries. The parent LC libraries consist of 40,000 antibacterial (Life Chemicals Activity targeted: antibacterials library) and 27,000 antiviral (Life Chemicals Activity targeted: antiviral library) compounds focused by 2D fingerprint methodology to have high similarity to known antibacterial and antiviral compounds taken from current literature. The remaining 6,250 compounds of the screened 25,000 compounds were selected from the general LC screening collection (Life Chemicals General: diversity library). The LC libraries have been pre-filtered to be 'Rule of 5' compliant (one exception tolerated). Additionally, a series of custom pre-filters, based in part on published data, were applied to each of the LC libraries prior to compound selection to remove compounds from consideration with known reactive functionalities and/or known toxicities. Molecular weight filters specified a range of 150-650 Daltons. The higher MW cut-off of 650 was used to reflect the known trend of increased weight and hydrophilicity amongst known antimicrobials. Finally, the most diverse compounds from each starting library that met the filtering criteria were selected based upon 2D fingerprints.

A saturated overnight culture of the test strain (923 pPvra-lux) in TSB (containing 10 µg/ml chloramphenicol for plasmid selection) was diluted 1:100 into fresh TSB. A 99 µL cell suspension and 1 µL test compound (final concentration 10 µM dissolved in DMSO) was applied to a 96-well plate and incubated at 37° C. The OD at 530 nm and luminescence were recorded at intervals of 0, 1, 2, 3, 4, and 24 hours. All compounds were tested in the presence and absence of oxacillin (2 µg/mL). For each 96-well plate assayed, 80 compounds were tested. The remaining 16 wells contained either cells in TSB alone (7 replicates), cells with oxacillin (2 µg/mL, 7 replicates), or blank TSB (2 replicates). Due to instrument limitations, only half of the library was screened each day (7 plates, 560 compounds). The full library was screened twice. Compounds identified in the primary screen that satisfied the criteria described in Example 2 were subjected to secondary screening.

In the secondary screen each microtiter plate contained either cells in TSB alone (16 replicates), cells with oxacillin (2 µg/mL, 31 replicates), or cells with test compound and oxacillin (2 µg/mL, 49 wells). Each compound was assayed in four separate biological replicates.

Confirmation of vraR Inhibition Via qRT-PCR—

A saturated overnight culture of strain 923 was diluted 1:100 into fresh TSB and grown at 37° C. with shaking. After one hour, test compound (10 µM) and oxacillin (2 µg/mL) were added and the culture was incubated for an additional hour. Bacteria were lysed via lysostaphin incubation (Ambi, 200 µg/mL) for 10 minutes at 25° C. RNA was purified with the Qiagen RNeasy kit, including treatment with DNase and cDNA generated using the high-capacity cDNA Archive Kit (Applied Biosystems). qRT-PCR was performed using molecular beacons and primers obtained from IDT. Specifically, a multiplex reaction consisting of a vraR probe (PrimeTime Probe /5' 6-FAM/TTG CCA AAG/ZEN/CCC ATG AGT TGA AGC CA/3'IAB-kFQ/) (SEQ ID NO: 3) with primers vraR-R (5'-TAG TTG GTG AAG GCG CTT CTG GTA-3') (SEQ ID NO: 4) and vraR-F (5'-TCG TCG CTT CTA CAC CAT CCA TGT-3') (SEQ ID NO: 5) to detect vra operon transcription combined with a gyrB endogenous control probe (/5Cy5/AAA TGG GAC GTC CAG CTG TCG AAG TT/3IAbRQSp/) (SEQ ID NO: 6) with primers (gyrBR 5'-CCG CCA AAT TTA CCA CCA GCA TGT-3') (SEQ ID NO: 7) and (gyrBF 5'-AAC GGA CGT GGT ATC CCA GTT GAT-3') (SEQ ID NO: 8).

Relative Quantification was performed using the ΔΔCT method facilitated by using the ABI Prism 7300 Sequence Detection Software (version 1.2.3) (4) (Applied Biosystems). Strain 923 grown in the absence of oxacillin was used as the comparator condition unless the oxacillin induced condition is indicated (5).

Example 2—Assay Strategy

Assay Development for Screening of Inhibitors of Growth and vraSR Expression—

By coupling the vraSR promoter to the luxABCDE operon, we were able to simultaneously monitor cell growth as a function of optical density (OD) and PvraSR expression as a function of luminescence (lux) (measured in relative light units (LU)). Prior to screening the Life Chemicals compound library for inhibitors of growth and/or luminescence, the optimal concentration of oxacillin and time points for collection of $OD_{600}$ and LUs, and criteria for classifying a compound. To this end, cells were cultured in 96 well microtiter plates, and growth and luminescence monitored in a plate reader.

When using CLSI guidelines, strain 923 has a 24-h oxacillin MIC of 16-32 µg/mL (Boyle-Vavra et al). However, when cultured in the 96-well format, the MIC of oxacillin of strain 923 was 8 µg/mL, and in 923 containing pPvra-lux, the MIC of oxacillin further dropped to 5 g/mL (FIG. 1A). Based on the MIC of oxacillin obtained in the 96-well format, we measured the OD600 and LU of cultures of strain 923 Pvra-lux supplemented with oxacillin in concentrations spanning 0 to 6 mg/L (FIG. 1). We found that vraSR expression reached its maximum 2 hours after induction (FIG. 1B), and 2 µg/mL oxacillin was the minimum concentration sufficient for maximal vraSR expression (FIG. 1C). Therefore, the library was screened using 2 µg/ml oxacillin, luminescence was the recorded at 2 hours, and $OD_{600}$ recorded at 24 hrs.

Figures 2A, 2B:
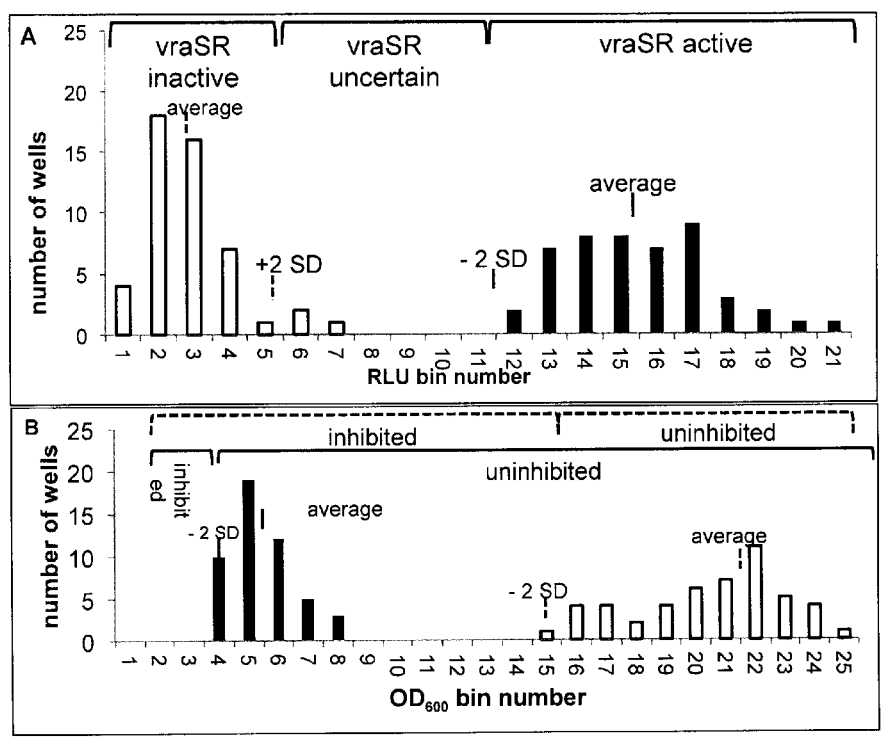
FIG. 2A-B: Distribution of OD and LU. Criteria for classification of growth and luminescence inhibition are based on reference data of strain 923 pPvra-lux grown in the presence or absence of oxacillin (2 μg/mL) (+/−Ox). (A) luminescence (B) absorbance. solid bars=oxacillin added (+Ox), empty bars=no oxacillin (−Ox).

To define the LU and $OD_{600}$ cutoff values for defining inhibition of luminescence and growth, respectively, data was obtained from 49 wells seeded with cell culture supplemented with 2 µg/ml oxacillin and 49 control wells seeded with cultures lacking oxacillin. The values were partitioned into bins for ease of visualization. The data were normally distributed for both LU (FIG. 2A) and OD600 values (FIG. 2B). Cutoff values were set at 2 SDs above or below the mean.

Values were classified as either vraSR-inactive, (RLUs less than two SDs above the mean of the no-oxacillin controls (FIG. 2A, white bars), vraSR-active (any value less than two SDs below the mean LU of the oxacillin-induced wells (FIG. 2A, black filled bars), or vraSR-uncertain (any value which falls between the other two categories).

For judging cell growth, cultures were classified as either "uninhibited" or "inhibited". "Uninhibited" was defined as any value less than 2 SDs below the mean of the no-oxacillin cultures (white bars), while "inhibited" wells had any value <2 SDs below the mean of the no oxacillin cultures (black bars, bins 4-8)(FIG. 2B).

Primary Screen—

The Life Chemicals Library was screened twice for its effects on growth and vraSR induction of the test strain, both in the presence and absence of oxacillin.

Relative Growth is defined by the following values and calculations:

Baseline correction: Absorbance @24 h-Absorbance @0 h

Positive control: test strain with 2 mg/L Oxacillin

Negative control: test strain with 20 mg/L Oxacillin

Relative growth=(Abs test strain-Abs negative)/(Abs positive-Abs negative)

Relative growth<0.50=dead cells=hit (confirmed by visual inspection) (Table 2)

Relative quantity vraSR is defined by the following values and calculations:

Baseline correction: LU @max-LU @0 h

Positive control: test strain with 2 mg/L Oxacillin

Relative luminescence=(Lux test strain-Lux negative)/(Lux positive-Lux negative)

Relative luminescence<0.50=vraSR repressed=hit (Table 2)

TABLE 2

| Compound family | Compound number | RG avg | RL avg |
| --- | --- | --- | --- |
| F0015 | 758 | −0.06 | 0.33 |
| F0020 | 1560 | 0.02 | −0.01 |
| F0191 | 4604 | −0.07 | −0.06 |
| F0230 | 74 | −0.07 | −0.10 |
| F0266 | 383 | 0.45 | 0.07 |
| F0301 | 350 | 0.24 | 0.15 |
| F0382 | 172 | 0.35 | 0.37 |
| F0401 | 39 | 0.30 | −0.05 |
| F0415 | 43 | −0.05 | −0.07 |
| F0447 | 264 | −0.03 | −0.05 |
| F0447 | 273 | −0.08 | −0.09 |
| F0447 | 277 | −0.06 | −0.11 |
| F0559 | 36 | −0.08 | −0.16 |
| F0559 | 106 | −0.07 | −0.07 |
| F0559 | 107 | −0.05 | −0.06 |
| F0559 | 127 | −0.05 | −0.11 |
| F0559 | 129 | −0.08 | −0.07 |
| F0559 | 148 | 0.02 | −0.04 |
| F0559 | 158 | 0.03 | −0.07 |
| F0559 | 171 | −0.06 | −0.11 |
| F0559 | 178 | −0.06 | −0.07 |
| F0559 | 189 | −0.05 | −0.08 |
| F0559 | 206 | 0.19 | −0.11 |
| F0559 | 246 | −0.03 | −0.08 |
| F0559 | 264 | −0.04 | −0.10 |
| F0559 | 279 | 0.40 | −0.09 |
| F0559 | 307 | −0.04 | −0.08 |
| F0559 | 311 | −0.06 | 0.02 |
| F0559 | 320 | 0.24 | −0.08 |
| F0559 | 321 | −0.03 | −0.09 |
| F0559 | 328 | 0.15 | 0.01 |
| F0559 | 350 | 0.43 | 0.11 |
| F0559 | 376 | −0.08 | −0.02 |
| F0559 | 377 | −0.08 | −0.09 |
| F0559 | 390 | −0.06 | −0.11 |
| F0559 | 398 | −0.07 | −0.11 |
| F0593 | 58 | 0.03 | −0.04 |
| F0600 | 1305 | 0.36 | 0.22 |
| F0608 | 19 | −0.02 | −0.12 |
| F0608 | 46 | −0.06 | −0.10 |
| F0608 | 71 | −0.03 | 0.01 |
| F0608 | 123 | −0.02 | −0.04 |
| F0608 | 146 | −0.05 | −0.12 |
| F0608 | 258 | −0.05 | −0.06 |
| F0608 | 410 | −0.07 | −0.07 |
| F0608 | 447 | −0.05 | −0.02 |
| F0608 | 448 | 0.19 | −0.04 |
| F0608 | 491 | −0.06 | −0.11 |
| F0608 | 543 | −0.02 | −0.08 |
| F0608 | 554 | −0.04 | −0.08 |
| F0608 | 560 | −0.07 | −0.07 |
| F0608 | 570 | −0.05 | −0.07 |
| F0608 | 575 | −0.02 | −0.09 |
| F0608 | 601 | −0.05 | −0.12 |
| F0608 | 614 | 0.08 | −0.05 |
| F0608 | 659 | −0.05 | −0.08 |
| F0608 | 661 | 0.11 | −0.04 |
| F0608 | 662 | −0.07 | −0.10 |
| F0608 | 664 | −0.04 | −0.01 |
| F0608 | 665 | 0.19 | −0.01 |
| F0608 | 668 | 0.02 | −0.06 |
| F0608 | 715 | −0.01 | −0.05 |
| F0608 | 728 | −0.02 | −0.01 |
| F0608 | 741 | −0.02 | −0.04 |
| F0608 | 895 | 0.03 | −0.06 |
| F0608 | 928 | −0.01 | 0.07 |
| F0608 | 950 | −0.01 | −0.14 |
| F0608 | 1062 | −0.04 | −0.10 |
| F0608 | 1080 | 0.03 | −0.04 |
| F0608 | 1161 | 0.00 | −0.07 |
| F0700 | 18 | −0.03 | −0.03 |
| F0737 | 364 | −0.03 | −0.03 |
| F0743 | 24 | −0.03 | −0.09 |
| F1009 | 383 | 0.28 | −0.04 |
| F1009 | 423 | −0.01 | −0.04 |
| F1013 | 42 | 0.05 | −0.04 |
| F1059 | 41 | −0.01 | 0.40 |
| F1094 | 42 | 0.02 | 0.45 |
| F1094 | 57 | 0.04 | 0.46 |
| F1118 | 378 | 0.01 | 0.42 |
| F1142 | 4245 | 0.03 | 0.36 |
| F1142 | 4597 | 0.03 | 0.37 |
| F1374 | 14 | 0.24 | 0.38 |
| F1374 | 36 | 0.04 | 0.35 |
| F1374 | 37 | 0.02 | 0.35 |
| F1374 | 43 | 0.04 | 0.35 |
| F1374 | 55 | 0.28 | 0.47 |
| F1374 | 58 | 0.03 | 0.33 |
| F1374 | 82 | 0.08 | 0.35 |
| F1374 | 112 | 0.02 | 0.38 |
| F1374 | 116 | 0.00 | 0.34 |
| F1374 | 138 | 0.00 | 0.40 |
| F1374 | 140 | 0.02 | 0.35 |
| F1374 | 141 | 0.04 | 0.40 |
| F1374 | 142 | 0.03 | 0.35 |
| F1374 | 148 | 0.04 | 0.36 |
| F1374 | 172 | 0.04 | 0.39 |
| F1374 | 188 | 0.02 | 0.33 |
| F1374 | 220 | 0.01 | 0.35 |
| F1374 | 224 | −0.01 | 0.34 |
| F1374 | 253 | 0.04 | 0.32 |
| F1374 | 254 | 0.06 | 0.36 |
| F1374 | 255 | 0.00 | 0.36 |
| F1374 | 276 | 0.01 | 0.39 |
| F1374 | 320 | 0.04 | 0.32 |
| F1374 | 352 | 0.03 | 0.41 |
| F1374 | 379 | 0.47 | 0.34 |
| F1374 | 396 | 0.04 | 0.34 |
| F1374 | 443 | 0.05 | 0.39 |
| F1374 | 455 | 0.03 | 0.33 |
| F1374 | 495 | 0.04 | 0.37 |
| F1374 | 562 | 0.02 | 0.38 |
| F1374 | 583 | 0.00 | 0.36 |
| F1374 | 651 | 0.04 | 0.38 |
| F1374 | 666 | 0.05 | 0.34 |
| F1374 | 742 | 0.04 | 0.40 |
| F1374 | 749 | 0.04 | 0.34 |
| F1374 | 757 | 0.02 | 0.29 |
| F1374 | 772 | 0.03 | 0.30 |
| F1374 | 836 | −0.01 | 0.31 |
| F1374 | 875 | 0.04 | 0.30 |
| F1374 | 982 | 0.13 | 0.35 |
| F1374 | 988 | 0.03 | 0.37 |
| F1374 | 1012 | 0.16 | 0.49 |
| F1374 | 1055 | 0.02 | 0.50 |
| F1374 | 1060 | 0.17 | 0.46 |
| F1374 | 1062 | 0.01 | 0.46 |
| F1374 | 1083 | 0.02 | 0.49 |
| F1374 | 1094 | 0.03 | 0.52 |
| F1374 | 1102 | 0.13 | 0.49 |
| F1374 | 1129 | 0.00 | 0.47 |
| F1374 | 1149 | −0.01 | 0.28 |
| F1374 | 1151 | −0.02 | 0.35 |

TABLE 2-continued

| Compound family | Compound number | RG avg | RL avg |
|---|---|---|---|
| F1374 | 2134 | 0.20 | 0.38 |
| F1374 | 2664 | 0.00 | 0.32 |
| F1374 | 2671 | 0.03 | 0.35 |
| F1374 | 2676 | 0.01 | 0.34 |
| F1374 | 2680 | 0.00 | 0.42 |
| F1374 | 2706 | 0.02 | 0.25 |
| F1374 | 2707 | 0.00 | 0.32 |
| F1374 | 2902 | 0.00 | 0.33 |
| F1605 | 796 | 0.16 | −0.07 |
| F1813 | 710 | −0.03 | 0.01 |
| F1813 | 711 | −0.02 | −0.02 |
| F1813 | 712 | −0.01 | 0.00 |
| F1821 | 817 | −0.01 | −0.07 |
| F1886 | 589 | 0.18 | 0.43 |
| F1886 | 1079 | 0.12 | 0.48 |
| F2090 | 579 | 0.00 | 0.04 |
| F2273 | 13 | −0.03 | −0.06 |
| F2273 | 29 | 0.16 | 0.29 |
| F2273 | 37 | 0.09 | 0.09 |
| F2273 | 114 | 0.26 | 0.26 |
| F2273 | 238 | 0.26 | 0.19 |
| F2273 | 385 | 0.28 | 0.16 |
| F2273 | 390 | 0.27 | 0.20 |
| F2273 | 415 | 0.27 | 0.22 |
| F2273 | 492 | 0.25 | 0.24 |
| F2289 | 31 | 0.26 | 0.30 |
| F2308 | 38 | −0.02 | −0.13 |
| F2359 | 308 | 0.22 | 0.07 |
| F2368 | 63 | −0.01 | −0.02 |
| F2368 | 431 | −0.02 | −0.06 |
| F2368 | 617 | −0.04 | −0.07 |
| F2368 | 619 | −0.03 | 0.01 |
| F2368 | 1143 | −0.01 | −0.09 |
| F2399 | 63 | 0.28 | 0.12 |
| F2438 | 2 | −0.02 | −0.18 |
| F2473 | 67 | −0.02 | −0.04 |
| F2473 | 211 | −0.01 | −0.06 |
| F2473 | 748 | 0.01 | −0.03 |
| F2483 | 58 | 0.14 | 0.04 |
| F2517 | 7 | −0.03 | −0.11 |
| F2517 | 14 | −0.03 | −0.07 |
| F2517 | 37 | −0.02 | −0.06 |
| F2517 | 165 | 0.31 | −0.07 |
| F2517 | 182 | 0.46 | −0.04 |
| F2517 | 329 | −0.02 | −0.11 |
| F2517 | 863 | 0.02 | −0.06 |
| F2518 | 2 | −0.02 | 0.01 |
| F2518 | 24 | −0.01 | 0.06 |
| F2518 | 39 | −0.01 | −0.07 |
| F2518 | 41 | 0.00 | −0.03 |
| F2518 | 49 | −0.03 | −0.05 |
| F2518 | 55 | 0.00 | −0.02 |
| F2518 | 85 | 0.00 | −0.05 |
| F2518 | 166 | −0.02 | −0.10 |
| F2518 | 168 | −0.03 | −0.07 |
| F2518 | 183 | 0.00 | −0.04 |
| F2518 | 186 | 0.01 | −0.09 |
| F2518 | 189 | 0.01 | −0.02 |
| F2518 | 213 | 0.01 | −0.01 |
| F2518 | 228 | 0.00 | −0.14 |
| F2518 | 295 | 0.01 | −0.09 |
| F2518 | 298 | −0.02 | 0.06 |
| F2518 | 301 | −0.01 | −0.10 |
| F2518 | 303 | 0.00 | −0.02 |
| F2518 | 329 | 0.00 | −0.11 |
| F2518 | 334 | 0.00 | −0.04 |
| F2518 | 342 | 0.00 | −0.02 |
| F2518 | 355 | −0.01 | −0.04 |
| F2518 | 360 | 0.04 | 0.13 |
| F2518 | 373 | 0.05 | −0.05 |
| F2518 | 414 | 0.01 | −0.02 |
| F2518 | 436 | 0.00 | −0.06 |
| F2518 | 445 | −0.01 | 0.05 |
| F2518 | 447 | 0.02 | 0.00 |
| F2518 | 451 | −0.01 | −0.10 |
| F2518 | 474 | 0.01 | −0.01 |
| F2518 | 477 | 0.01 | 0.03 |
| F2518 | 481 | 0.00 | −0.05 |
| F2518 | 483 | −0.02 | −0.04 |
| F2518 | 484 | 0.02 | 0.02 |
| F2518 | 504 | 0.01 | 0.00 |
| F2518 | 517 | 0.01 | −0.08 |
| F2518 | 534 | 0.01 | 0.04 |
| F2518 | 558 | −0.02 | −0.08 |
| F2518 | 1563 | 0.00 | −0.16 |
| F2537 | 144 | 0.28 | 0.16 |
| F2619 | 556 | 0.25 | 0.52 |
| F2645 | 12 | 0.41 | 0.51 |
| F2645 | 67 | 0.02 | 0.37 |
| F2645 | 99 | 0.09 | 0.43 |
| F2645 | 115 | 0.13 | 0.45 |
| F2645 | 188 | 0.03 | 0.37 |
| F2645 | 379 | 0.04 | 0.37 |
| F2645 | 405 | 0.29 | 0.57 |
| F2647 | 309 | 0.16 | 0.35 |
| F2653 | 136 | 0.29 | 0.57 |
| F2703 | 396 | 0.06 | 0.19 |
| F2708 | 138 | 0.02 | −0.07 |
| F2730 | 247 | 0.31 | 0.16 |
| F2767 | 12 | 0.02 | 0.01 |
| F2767 | 17 | 0.00 | −0.15 |
| F2767 | 26 | 0.03 | −0.05 |
| F2767 | 204 | −0.02 | −0.09 |
| F2767 | 205 | −0.01 | −0.08 |
| F2767 | 223 | 0.02 | −0.14 |
| F2768 | 400 | 0.01 | −0.05 |
| F2768 | 463 | −0.02 | −0.03 |
| F2768 | 504 | −0.01 | −0.02 |
| F2813 | 883 | −0.03 | −0.01 |
| F2832 | 112 | −0.01 | −0.06 |
| F2962 | 176 | 0.06 | −0.08 |
| F3068 | 37 | −0.02 | 0.05 |
| F3225 | 3356 | 0.39 | 0.01 |
| F3305 | 354 | 0.00 | 0.03 |
| F3348 | 30 | 0.05 | 0.12 |
| F3348 | 373 | 0.05 | 0.41 |
| F3348 | 533 | 0.02 | 0.01 |
| F3348 | 667 | −0.02 | −0.03 |
| F3394 | 78 | 0.26 | 0.26 |
| F5074 | 91 | 0.01 | −0.04 |
| F5074 | 712 | −0.02 | −0.03 |
| F5079 | 42 | −0.03 | −0.04 |
| F5079 | 73 | 0.23 | 0.09 |
| F5079 | 242 | −0.01 | −0.07 |
| F5093 | 12 | 0.01 | −0.01 |
| F5093 | 37 | 0.02 | −0.03 |
| F5093 | 40 | 0.03 | −0.02 |
| F5093 | 46 | −0.01 | −0.07 |
| F5093 | 101 | −0.02 | −0.04 |
| F5093 | 111 | −0.02 | −0.02 |
| F5093 | 196 | −0.01 | −0.01 |
| F5123 | 84 | 0.02 | −0.08 |
| F5237 | 56 | 0.02 | −0.05 |
| F5562 | 130 | 0.02 | −0.08 |
| F5669 | 378 | −0.02 | −0.06 |
| F5772 | 8284 | 0.37 | −0.01 |
| F5773 | 561 | 0.01 | −0.05 |
| F5833 | 1551 | 0.01 | −0.03 |
| F5854 | 2599 | 0.01 | −0.06 |
| F5882 | 3050 | 0.39 | 0.25 |
| F5882 | 3269 | −0.01 | −0.02 |
| F5946 | 241 | 0.06 | −0.05 |
| F5948 | 234 | 0.08 | 0.05 |
| F6153 | 183 | 0.00 | −0.01 |
| F9995 | 20 | 0.28 | 0.09 |
| F9995 | 306 | 0.00 | −0.02 |
| F9995 | 825 | −0.03 | −0.07 |

TABLE 3

Count of Compound family

| Row Labels | Total |
|---|---|
| F0015 | 1 |
| F0020 | 1 |
| F0191 | 1 |
| F0230 | 1 |
| F0266 | 1 |
| F0301 | 1 |
| F0382 | 1 |
| F0401 | 1 |
| F0415 | 1 |
| F0447 | 3 |
| F0559 | 24 |
| F0593 | 1 |
| F0600 | 1 |
| F0608 | 32 |
| F0700 | 1 |
| F0737 | 1 |
| F0743 | 1 |
| F1009 | 2 |
| F1013 | 1 |
| F1059 | 1 |
| F1094 | 2 |
| F1118 | 1 |
| F1142 | 2 |
| F1374 | 59 |
| F1605 | 1 |
| F1813 | 3 |
| F1821 | 1 |
| F1886 | 2 |
| F2090 | 1 |
| F2273 | 9 |
| F2289 | 1 |
| F2308 | 1 |
| F2359 | 1 |
| F2368 | 5 |
| F2399 | 1 |
| F2438 | 1 |
| F2473 | 3 |
| F2483 | 1 |
| F2517 | 7 |
| F2518 | 39 |
| F2537 | 1 |
| F2619 | 1 |
| F2645 | 7 |
| F2647 | 1 |
| F2653 | 1 |
| F2703 | 1 |
| F2708 | 1 |
| F2730 | 1 |
| F2767 | 6 |
| F2768 | 3 |
| F2813 | 1 |
| F2832 | 1 |
| F2962 | 1 |
| F3068 | 1 |
| F3225 | 1 |
| F3305 | 1 |
| F3348 | 4 |
| F3394 | 1 |
| F5074 | 2 |
| F5079 | 3 |
| F5093 | 7 |
| F5123 | 1 |
| F5237 | 1 |
| F5562 | 1 |
| F5669 | 1 |
| F5772 | 1 |
| F5773 | 1 |
| F5833 | 1 |
| F5854 | 1 |
| F5882 | 2 |
| F5946 | 1 |
| F5948 | 1 |
| F6153 | 1 |
| F9995 | 3 |
| Grand Total | 280 |

Lead hits were additionally filtered using the following filtering strategy. A REOS filter (rapid elimination of swill) was applied. This is similar to the "rule of 5" filter, with property filters for MW, hydrogen bonds, charge, etc. It also applies additional functional group filters. The result of applying this filter was elimination of 30 compounds. A PAINS (Pan Assay Interference) filter was applied. This filter detects hits that come up in lots of high-throughput assays and eliminated 6 compounds. A filter to eliminate possible false positives based on chemotype (e.g. Oxadiazoles are known to interfere with firefly luciferase) was applied. This filter eliminated approximately 220 compounds. The result of filter application was a "Top 40" library (Table 4).

TABLE 4

UIC Top 40 library

| full ID | Sample # for Plate reader | maximum non-GI conc (µg/mL) | RG Ox avg | RL Ox avg | syn | rep | vraSR repressing synergist |
|---|---|---|---|---|---|---|---|
| F3068-0037 | 15 | 400 | −0.01 | 0.11 | x | x | 1. confirmed |
| F2399-0063 | 8 | 400 | −0.01 | 0.04 | x | x | 1. confirmed |
| F2619-0556 | 11 | 400 | 0.01 | 0.28 | x | x | 1. confirmed |
| F3348-0030 | 17 | 400 | 0.01 | 0.05 | x | x | 1. confirmed |
| F2359-0308 | 34 | 400 | 0.01 | 0.01 | x | x | 1. confirmed |
| F2703-0396 | 12 | 400 | 0.01 | 0.34 | x | x | 1. confirmed |
| F3348-0533 | 18 | 400 | 0.02 | 0.10 | x | x | 1. confirmed |
| F5882-3050 | 27 | 400 | 0.02 | 0.07 | x | x | 1. confirmed |
| F2645-0188 | 36 | 40 | 0.03 | 0.05 | x | x | 1. confirmed |
| F2962-0176 | 38 | 400 | 0.04 | 0.01 | x | x | 1. confirmed |
| F1142-4597 | 30 | 40 | 0.08 | −0.01 | x | x | 1. confirmed |
| F2730-0247 | 13 | 400 | 0.23 | 0.15 | x | x | 1. confirmed |
| F1142-4245 | 5 | 400 | 0.25 | 0.04 | x | x | 1. confirmed |
| F2090-0579 | 7 | 400 | 0.30 | 0.11 | x | x | 1. confirmed |
| F5772-8284 | 40 | 400 | 0.37 | 0.52 | x | ? | 2. possible |
| F0447-0273 | 28 | 40 | 0.39 | 0.08 | x | x | 1. confirmed |
| F3348-0667 | 19 | 40 | 0.51 | 0.72 | x | ? | 2. possible |
| F1374-0082 | 6 | 40 | 0.67 | 0.08 | ? | x | 2. possible |
| F0020-1560 | 2 | 40 | 0.68 | 0.17 | ? | x | 2. possible |
| F1813-0710 | 31 | 400 | 0.69 | 0.20 | ? | x | 2. possible |
| F1813-0712 | 33 | 400 | 0.71 | 0.20 | ? | x | 2. possible |
| F1813-0711 | 32 | 400 | 0.85 | 0.43 | ? | x | 2. possible |
| F0015-0758 | 1 | 400 | 0.92 | 0.25 |  | x | 3. no effect |
| F2517-0863 | 10 | 4 | 0.92 | 1.18 |  |  | 3. no effect |
| F0600-1305 | 29 | 400 | 0.94 | 0.15 |  | x | 3. no effect |
| F2438-0002 | 9 | 40 | 0.95 | 0.62 |  | ? | 3. no effect |
| F0608-0146 | 3 | 40 | 0.96 | 1.11 |  |  | 3. no effect |
| F3348-0373 | 39 | 40 | 0.99 | 0.80 |  | ? | 3. no effect |
| F5833-1551 | 25 | 40 | 0.99 | 0.56 |  | ? | 3. no effect |
| F1118-0378 | 4 | 40 | 1.00 | 0.65 |  | ? | 3. no effect |
| F5669-0378 | 24 | 40 | 1.00 | 0.71 |  | ? | 3. no effect |
| F5854-2599 | 26 | 40 | 1.01 | 0.54 |  | ? | 3. no effect |
| F3305-0354 | 16 | 40 | 1.01 | 0.61 |  | ? | 3. no effect |
| F2813-0883 | 14 | 40 | 1.03 | 1.28 |  |  | 3. no effect |
| F5562-0130 | 23 | 40 | 1.03 | 0.57 |  | ? | 3. no effect |
| F2708-0138 | 37 | 40 | 1.04 | 0.69 |  | ? | 3. no effect |
| F5123-0084 | 21 | 40 | 1.08 | 0.67 |  | ? | 3. no effect |
| F5237-0056 | 22 | 40 | 1.10 | 0.72 |  | ? | 3. no effect |
| F2518-0213 | 35 | 4 | 1.14 | 0.33 |  | x | 3. no effect |
| F3394-0078 | 20 | 40 | 1.24 | 0.41 |  | x | 3. no effect |

Synergy Confirmation of "Top 40".

To determine if the compounds found in the oxacillin (Ox) synergy screen also inhibited growth on their own, compounds were tested alone at the "Screen" concentration, and at 1:10 and 1:100 dilutions to find the maximum concentration where it did NOT inhibit growth (i.e., Subinhibitory) (Table 5). Inhibition of luminescence by lead compounds was also tested to determine if it was artifactual due to interference with lux rather than expression of Pvra, which would have given a false positive in the screen. To this end the ability of the compound to inhibit light production from a transcriptional fusion between lux and the promoter from the constitutively expressed pyruvate dehydrogenase gene (Ppdh-lux) in *S. aureus* (RN4220) was tested. 22 compounds synergized with Ox and genuinely inhibited Pvra luminescence including 2 of the 5 oxadiazoles tested (Table 6). Using RT-PCR 12 compounds were confirmed that repress vraTSR expression (Table 6, marked by x). (- indicates a lack of repression by RT-PCR).

TABLE 5

Top 40 leads after secondary screen

| PR Sample # from full library | Full ID # | concentration (µg/mL) |
|---|---|---|
| 2 | F0020-1560 | 40 |
| 3 | F0608-0146 | 40 |
| 4 | F1118-0378 | 40 |
| 6 | F1374-0062 | 40 |
| 9 | F2438-0002 | 40 |
| 10 | F2517-0663 | 40 |
| 14 | F2613-0883 | 40 |
| 16 | F3305-0354 | 40 |
| 19 | F3348-0667 | 40 |
| 20 | F3394-0078 | 40 |
| 21 | F5123-0084 | 40 |
| 22 | F5237-0056 | 40 |
| 23 | F5562-0130 | 40 |
| 24 | F5669-0378 | 40 |
| 25 | F5833-1551 | 40 |
| 26 | F5854-2599 | 40 |
| 28 | F0447-0273 | 40 |
| 30 | F1142-4597 | 40 |
| 35 | F2518-0213 | 40 |
| 36 | F2645-0188 | 40 |
| 37 | F2706-0138 | 40 |
| 39 | F3348-0373 | 40 |
| 2 | F0020-1560 | 4 |
| 3 | F0608-0146 | 4 |
| 4 | F1118-0378 | 4 |
| 6 | F1374-0062 | 4 |
| 9 | F2438-0002 | 4 |
| 10 | F2517-0663 | 4 |
| 14 | F2613-0883 | 4 |
| 16 | F3305-0354 | 4 |
| 19 | F3348-0667 | 4 |
| 20 | F3394-0078 | 4 |
| 21 | F5123-0084 | 4 |
| 22 | F5237-0056 | 4 |
| 23 | F5562-0130 | 4 |
| 24 | F5669-0378 | 4 |
| 25 | F5833-1551 | 4 |
| 26 | F5854-2599 | 4 |
| 28 | F0447-0273 | 4 |
| 30 | F1142-4597 | 4 |
| 35 | F2518-0213 | 4 |
| 36 | F2645-0188 | 4 |
| 37 | F2708-0138 | 4 |
| 39 | F3348-0373 | 4 |

TABLE 6

| full ID | conc Inh (µg/mL) | RT hit rep 1 |
|---|---|---|
| F1374-0082 | 40 | x |
| F2399-0063 | 400 | x |
| F2619-0556 | 400 | x |
| F2703-0396 | 400 | x |
| F2730-0247 | 400 | x |
| F3348-0667 | 40 | x |
| F5882-3050 | 400 | x |
| F1813-0710 | 400 | x |
| F1813-0711 | 400 | x |
| F1813-0712 | 400 | x |
| F2645-0188 | 40 | x |
| F2962-0176 | 400 | x |
| F0020-1560 | 40 | — |
| F1142-4245 | 400 | — |
| F2090-0579 | 400 | — |
| F3068-0037 | 400 | — |
| F3348-0030 | 400 | — |
| F3348-0533 | 400 | — |
| F0447-0273 | 40 | — |
| F1142-4597 | 40 | — |
| F2359-0308 | 400 | — |
| F5772-8284 | 400 | — |

TABLE 7

MICs (minimal inhibitory concentrations) vs multiple strains of MRSA

| | | | Ox MIC alone | Ox MIC (mg/L) in presence of compound | | | | | |
|---|---|---|---|---|---|---|---|---|---|
| Isolate ID | SCCmec | ST | | F2645-0188 (0.25 mg/L) | F0020-1560 (1 mg/L) | F2703-0396 (2 mg/L) | F5882-3050 (2 mg/L) | F1813-0712 (4 mg/L) | F2619-0556 (4 mg/L) |
| 923 | IV | 8 | 16 | 2 | 1 | <0.25 | <0.25 | 4 | <0.25 |
| 1176 | II | 231 | 32 | <0.5 | <0.5 | <0.5 | <0.5 | 16 | <0.5 |
| 2169 | IV | 72 | 16 | 0.5 | 1 | <0.25 | <0.25 | 8 | <0.25 |
| 11095 | II | 105 | 256 | 32 | <2 | <2 | <2 | 256 | 128 |
| 13113 | II | 5 | 16 | <0.13 | <0.13 | <0.13 | <0.13 | 16 | <0.13 |
| 13354 | IV | 5 | 8 | <0.13 | <0.13 | <0.13 | <0.13 | 8 | <0.13 |
| 14315 | IV | 1 | 32 | <0.5 | <0.5 | <0.5 | <0.5 | 16 | <0.5 |
| 8004-01 | III | 239 | 256 | 64 | <4 | 64 | 32 | 512 | <4 |
| 8010-01 | IV | 8 | 16 | 0.5 | 1 | <0.25 | <0.25 | 16 | <0.25 |

TABLE 7-continued

MICs (minimal inhibitory concentrations) vs multiple strains of MRSA

| | | | Ox | Ox MIC (mg/L) in presence of compound | | | | | |
|---|---|---|---|---|---|---|---|---|---|
| Isolate ID | SCCmec | ST | MIC alone | F2645-0188 (0.25 mg/L) | F0020-1560 (1 mg/L) | F2703-0396 (2 mg/L) | F5882-3050 (2 mg/L) | F1813-0712 (4 mg/L) | F2619-0556 (4 mg/L) |
| 8227-01 | IV | 87 | 2 | 0.5 | 0.25 | <0.06 | <0.06 | 0.5 | <0.06 |
| Q2461 | VT | 59 | 8 | 0.25 | 4 | <0.13 | 0.5 | 16 | 1 |

ST, indicates the genetic background of the MRSA strain.
SCCmec (staphylococcal cassette chromosome mec; coding for resistance to the antibiotic methicillin), designates the SCCmec type.
OX MIC alone is the Ox MIC of 923 in the absence of inhibitor.

Synergy Testing—

Checkerboard MIC testing. The interactions of F2645-0188, F0020-1560, F2703-0396, F5882-3050, F1813-0712 and F2619-0556 were assessed for synergy by checkerboard MIC testing using each test compound (0.25 to 16 μg/mL) and oxacillin (2 to 32 μg/mL) in 2-fold serial dilutions according to the method in CLSI M07-A8. oxacillin and compounds were prepared to 4 times their final concentration in TSB containing 2% NaCl. 250 μL of each concentration of oxacillin and each concentration of compound were applied to a 48-well plate to create a 6×8 checkerboard. A concentration series of oxacillin alone and compound alone were included so that the MIC of oxacillin and test compound alone could be determined. All wells were inoculated with 500 μL of a 1×10$^6$ cfu/mL suspension of strain 923 in TSB containing 2% NaCl. Plates were incubated overnight at 37° C. and MICs were visually determined at 24 h (Table 8).

Example 3—Binding to VraS and/or VraR

Compound F2645-0188 Binds to the Cytoplasmic Domain of VraS ("VraS-C")

Figure 3:
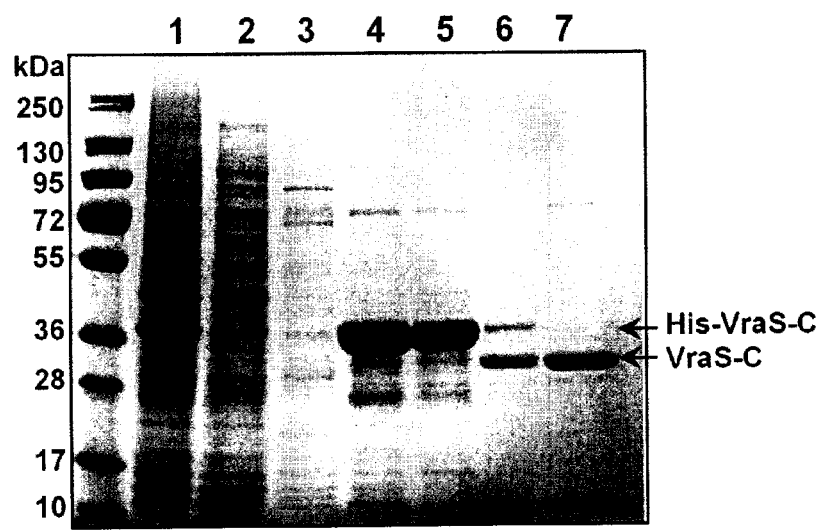
FIG. 3: VraS Cytoplasmic domain (VraS-C) expression and purification gel documentation and analysis. VraS-C was expressed and purified as described in Example 3. The gel is loaded as follows: Lane 1: Supernatant; Lane 2: flow-through from the first HisTrap column; Lane 3: wash with 68 mM imidazole; Lane: 4 elution fraction with 200 mM imidazole; Lane 5 elution fraction with 350 mM imidazole Lane 6: after digestion with 3C HRV protease: and Lane 7: final His-tag cleaved VraS-C.

The cytoplasmic domain of VraS (VraS-C) used in SPR was obtained by PCR from USA300 strain 923 using primers: 5'-AAAGGATCCAAAATCAATCAG-CAAAATGA-3' (SEQ ID NO: 9) and 5'-AAAAAGCT-TATCGTCATACGAATCCTCCT-3 (SEQ ID NO: 10). This clone was expressed in E. coli strain BL21 (Star, pLysS) (Invitrogen) (Ebook 333). VraR was cloned at BamHI and HindIII sites in pet28a (Novagen) with its own stop codon. This is a kanamycin selection vector. vraR was PCR amplified from strain 275 using primers: 5'-AAAGGATCC ATGACGATAAAGTATGTTTG-3' (SEQ ID NO: 11) and 5'-AAAAAGCTT CGATACGAACTATTGA-3' (SEQ ID NO: 12). This clone was expressed in E. coli strain BL21 (DE3, pLysS) (Invitrogen) (Ebook 331). The expression and purification is depicted in FIG. 3.

Figure 4:
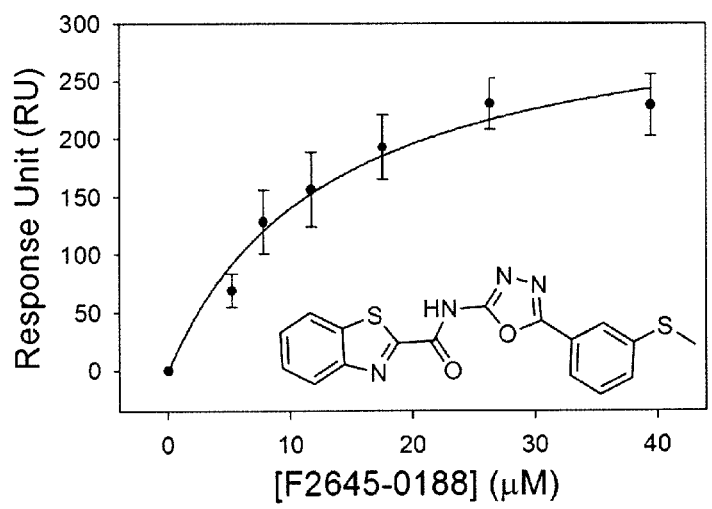
FIG. 4: SPR (Surface Plasmon Resonance) binding assay results for F2645-0188. Depicted is the fitting curve of compound F2645-0188 with a single rectangular hyperbolic equation using Sigmaplot 11.0. The determined $K_D$ was 13.2±3.2 μM. All data were normalized for immobilization levels of VraS-C protein.

His-tagged VraS, VraR, and an unrelated protein (PurC from Bacillus anthracis) were prepared in assay buffer containing 10 mM phosphate, pH 7.4, 2.7 mM KCl, 137 mM NaCl, 0.5% Tween-20, and 1 mM TCEP. Each protein was immobilized on vertical channels of a HTE sensor chip (Bio-Rad) using ProteOn™ XPR36 instrument (Bio-Rad). Of six vertical flow channels, VraS was immobilized on channels 1 and 2, and VraR was immobilized on channels 3 and 4. An unrelated protein, PurC, was immobilized on the 5$^{th}$ channel as a control, and blank immobilization was done on last channel as another control. All compounds to be analyzed were initially prepared as 10 mM stock solutions in 100% DMSO. Compound solutions with a series of increasing concentrations (0-100 μM at 1.5-fold dilution) were applied to six parallel channels at a 30 L/min flow rate at room temperature. Sensorgrams were analyzed using the ProteOn Manager™ software, and response unit difference (ΔRU) values at each concentration were measured during the equilibration phase. Data were double referenced with both blank and interspot RU values. The ProteOn Manager™ software was used to fit the data to a single rectangular hyperbolic curve to determine dissociation equilibrium constant ($K_D$) values. The hyperbolic function, $y=y_{max} \cdot x/(K_D+x)$, was used to plot response units and corresponding concentration, where y is the response, $y_{max}$ is the maximum response and x is the compound concentration. The fitting curve of compound F2645-0188 is depicted in FIG. 4.

Figure 5:
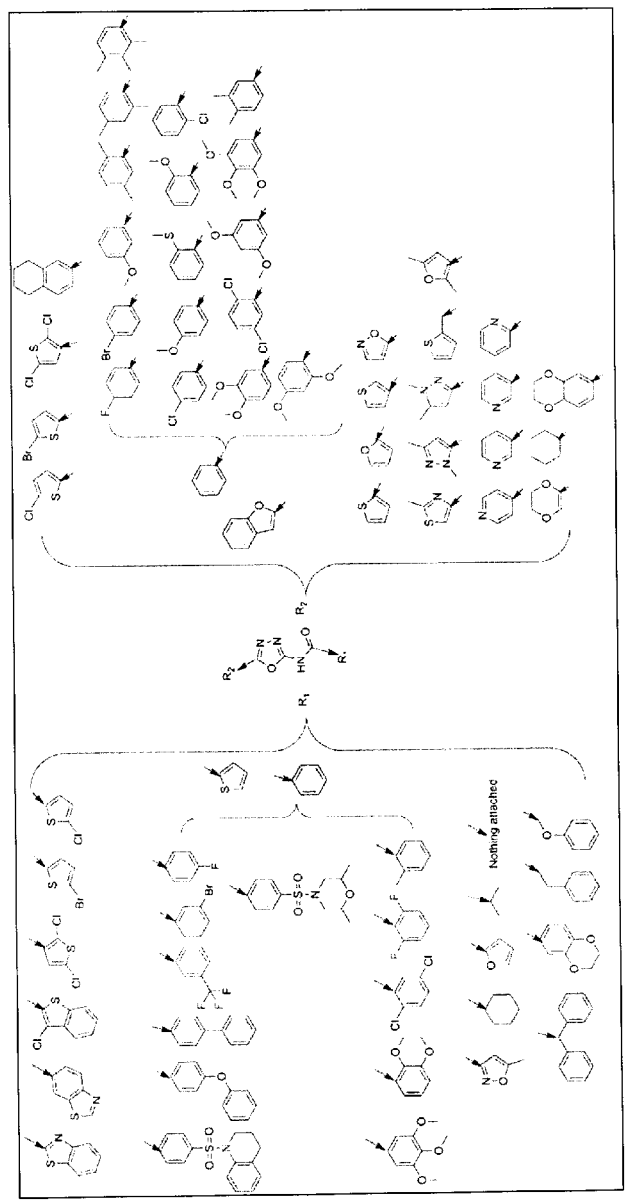
FIG. 5: Structure-activity relationship (SAR) analysis of primary and secondary assay data for activity of oxadiazole-carboxaminde analogs. Based on the SAR analysis, substituents were identified that may act to increase activity, decrease activity, or may be neutral to activity. Those that may increase activity are shown in section A (top). Those that may decrease activity are shown in section C (bottom). Those that may produce no apparent increase or decrease in activity are shown in section B (middle) producing no apparent increase or decrease in activity
Figure 6:
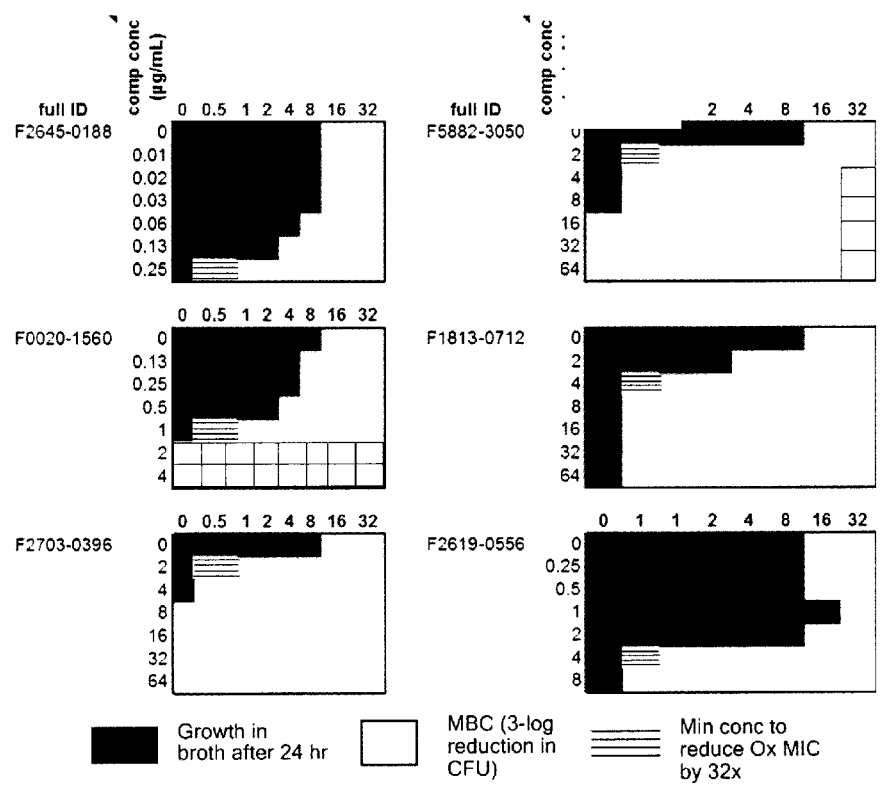
FIG. 6: Checkerboard MICs (boxes with horizontal lines) and MBCs (minimal bactericidal concentrations; boxes with black borders) of OX and inhibitors. Black-bordered boxes mark the concentration of inhibitor that decreased the Oxacillin MIC to 0.5 to 1 (=susceptible).

As shown in Table 9, compound F2645-0188 bound untagged VraS-C protein with a $K_D$ of 13.2±3.2 μM and His-tagged VraS-C with a $K_D$ of 56.1±16.3 μM. This indicates that F2645-0188 may potentiate oxacillin by directly binding to VraS protein and inhibiting its function. F2645-0188 has a central core structure consisting of the oxadiazole-carboxamide, that was used to analyze the primary and secondary screening data to evaluate the types of $R_1$ and $R_2$ substituents that affected synergistic activity. The results of that analysis are shown in FIG. 5, with substituents shown in section A (top) acting to increase activity of the resulting compound, substituents shown in section C (bottom) generally acting to decrease activity of the resulting compound, and substituents shown in section B (middle) producing no apparent increase or decrease in activity. The full Life Chemicals library was then searched for analogs with substituents that appeared likely to enhance synergistic activity. Twenty analogs were selected, as shown in Table 9, and were tested for their ability to bind VraS-C or VraR.

As shown in Table 9, compounds F1374-0033, F1374-0037, F1374-2739, and F2518-0474 bound to VraS-C, and compounds F1374-2739 and F2518-0327 bound to VraR. Like compound F2645-0188, the 1,3,4-oxadiazoles that bind VraS, VraR, or both may also potentiate oxacillin and other antibiotics that interfere with cell wall synthesis, including but not limited to vancomycin, daptomycin, and teichoplanin. Table 9 also shows that pyrvinium, a compound shown to potentiate oxacillin and vancomycin in co-pending application PCT/US2013/068085, also binds to VraS.

TABLE 9

Binding of 1,3,4-oxadiazoles, clomiphene, pyrvinium, and gossypol to VraS or VraR.

| Structure | ID | MW | $K_D$ (μM) (RUmax) VraS | VraR | PurC (control) |
|---|---|---|---|---|---|
| 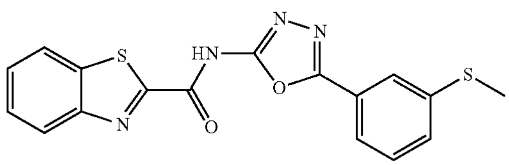 [SMILES: CSc1cccc(-c2nnc(NC(=O)c3nc4ccccc4s3)o2)c1] | F2645-0188 | 368.4 | Previous run with untagged VraS 13.2 ± 3.2 (325 ± 33) | NT (Not tested) | NT |
| | | | New run with His-tagged VraS 56.1 ± 16.3 (74.1 ± 10.7) | NB (No Binding) | NB |
| 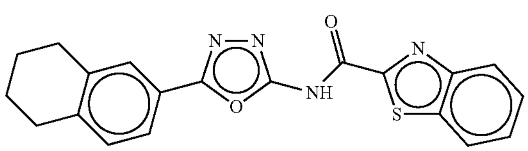 | F0608-0570 | 376.4 | NB | NB | NB |
| 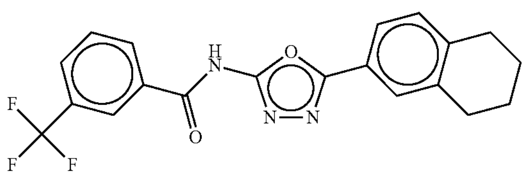 | F0608-0575 | 387.4 | NB | NB | NB |
| 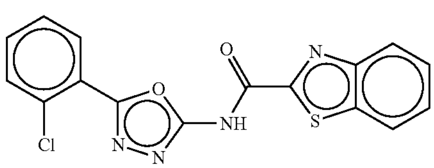 | F1374-0033 | 356.8 | 19.6 ± 4.4 (64.3 ± 5.4) | NB | NB |
| 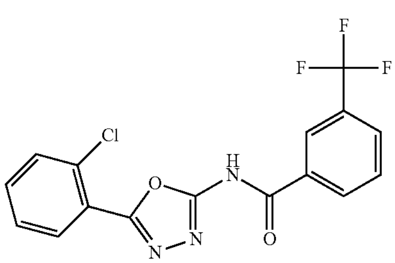 [SMILES: O=C(Nc1nnc(-c2ccccc2Cl)o1)c1cccc(C(F)(F)F)c1] | F1374-0037 | 323.7 | 25.8 ± 4.8 (45.1 ± 3.2) | NB | NB |
| 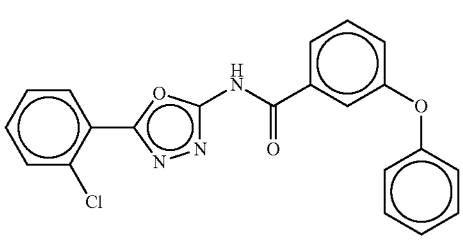 | F1374-0081 | 391.8 | NB | NB | NB |

TABLE 9-continued
Binding of 1,3,4-oxadiazoles, clomiphene, pyrvinium, and gossypol to VraS or VraR.
| Structure | ID | MW | $K_D$ (μM) (RUmax) VraS | VraR | PurC (control) |
|---|---|---|---|---|---|
| 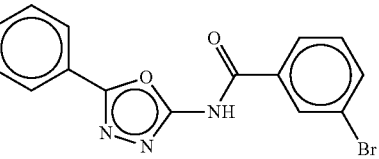 | F1374-0119 | 362.2 | NB | NB | NB |
| 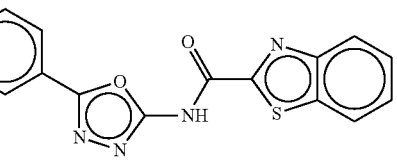 | F1374-0138 | 340.3 | NB | NB | NB |
| 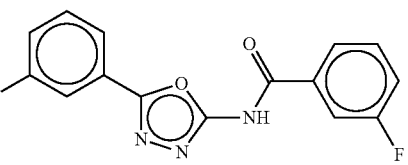 | F1374-0327 | 313.3 | NB | NB | NB |
| 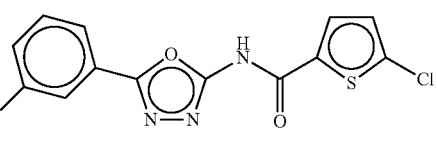 | F1374-0351 | 335.8 | NB | NB | NB |
| 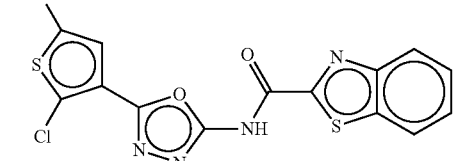 | F1374-2739 | 397.3 | 69.6 ± 11.6 (69.1 ± 6.2) | 54.4 ± 12.2 (80.3 ± 8.8) | NB |
| 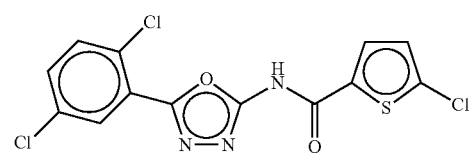 | F2518-0042 | 374.6 | NB | NB | NB |
| 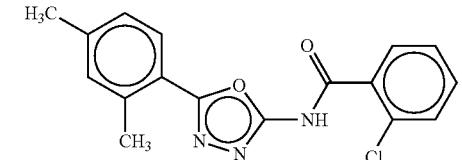 | F2518-0150 | 327.8 | NB | NB | NB |
| 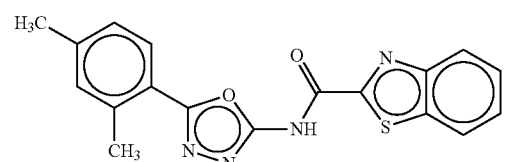 | F2518-0183 | 350.4 | NB | NB | NB |

TABLE 9-continued

Binding of 1,3,4-oxadiazoles, clomiphene, pyrvinium, and gossypol to VraS or VraR.

| Structure | ID | MW | $K_D$ (μM) (RUmax) VraS | VraR | PurC (control) |
|---|---|---|---|---|---|
| 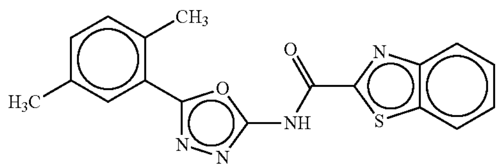 | F2518-0327 | 350.4 | NB | 15.4 ± 6.4 (46.5 ± 2.9) | NB |
| 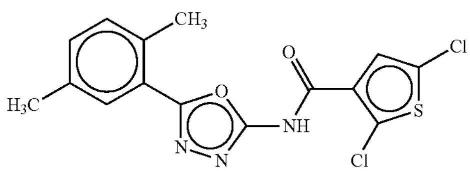 | F2518-0360 | 368.2 | NB | NB | NB |
| 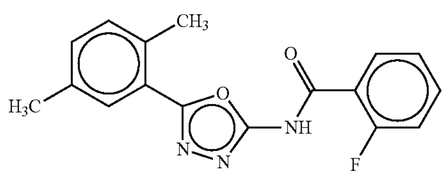 | F2518-0382 | 311.3 | NB | NB | NB |
| 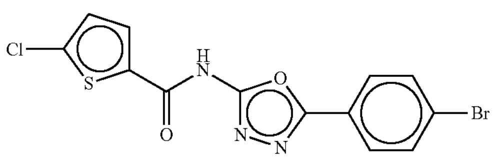 | F2518-0474 | 384.6 | 79.5 ± 34.6 (52.9 ± 12.8) | 22.2 ± 5.4 (27.5 ± 2.4, too small) | NB |
| 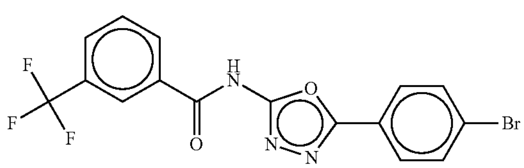 | F2518-0477 | 412.2 | NB | NB | NB |
| 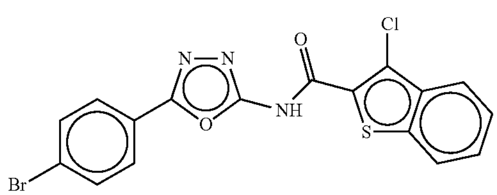 | F2518-0484 | 434.7 | NB | NB | NB |
| 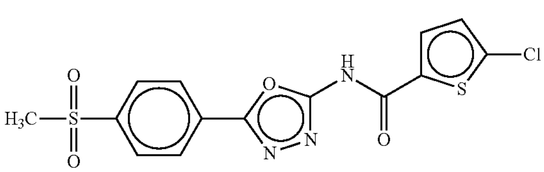 | F2645-0790 | 383.8 | NB | NB | NB |

TABLE 9-continued

Binding of 1,3,4-oxadiazoles, clomiphene, pyrvinium, and gossypol to VraS or VraR.

| Structure | ID | MW | $K_D$ (μM) (RUmax) VraS | VraR | PurC (control) |
|---|---|---|---|---|---|
| 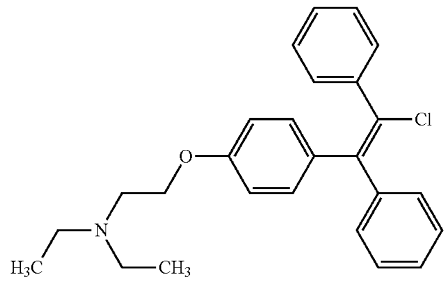 [SMILES: CCN(CC)CCOc1ccc(/C(=C(/Cl)c2ccccc2)c2ccccc2)cc1] | Clomiphene | 406.0 | NB | NB | NB |
| 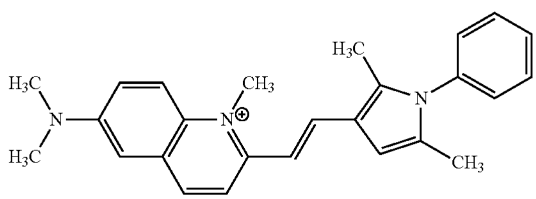 [SMILES: Cc1cc(/C=C/c2ccc3cc(N(C)C)ccc3[n+]2C)c(C)n1-c1ccccc1] | Pyrvinium | 382.5 | 21.3 ± 3.6 (46.5 ± 2.9) | NB | NB |
| 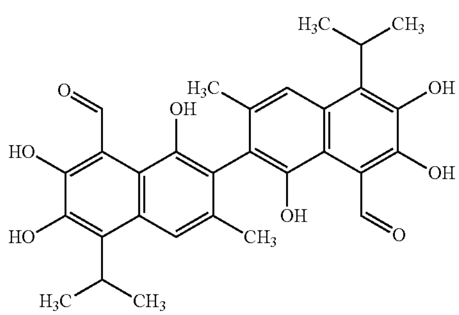 [SMILES: Cc1cc2c(C(C)C)c(O)c(O)c(C=O)c2c(O)c1-c1c(C)cc2c(C(C)C)c(O)c(O)c(C=O)c2c1O] | Gossypol | 518.6 | NB | NB | NB |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Berge, et al., *J Pharmaceutical Sci.* 66:1, 1977.
Boyle-Vavra, et al., *Antimicrob Agents Chemother.* 57(1): 83-95, 2013.
Boyle-Vavra, et al., *FEMS Microbiol Lett.* 262(2): 163-171, 2006.
Francis, et al., *Infect Inmmun.* 68(6):3594-3600, 2000.
Jo, et al., *Antimicrob Agents Chemother.* 55:2818-23, 2011.
Livak & Schmittgen, *Methods.* 25(4):402-408, 2001.
Martin, "Remington's Pharmaceutical Sciences", 18th Ed., Mack Publishing Co.: Pa., 1990.
Montgomery, et al., *J Infect Dis.* 198(4):561-570, 2008.
Yin, et al., *Antimicrobial Agents Chemother.* 50(1):336-343, 2006.

The invention claimed is:

1. A method for inhibiting a *staphylococcus* infection comprising administering to a subject having a *staphylococcus* infection or at risk of a *staphylococcus* infection:
   (a) an antibiotic, and;
   (b) an antibiotic potentiator, wherein the antibiotic potentiator is a compound of the formula:

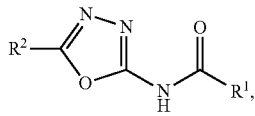

wherein $R^1$ may be -(4-chlorophenoxy)methyl, 1-(thiophen-2-yl)cyclopentyl, 1,2,3,4-tetrahydronaphthalen-6-yl, 1-isopropyl-1H-pyrazol-5-yl, 2-(thiophen-2-yl)quinolin-4-yl, 2,3-dihyrdobenzo[b][1,4]dioxin-6-yl, 2,4-dichlorophenyl, 2,5-dichlorophenyl, 2,5-dichlorothiophen-3-yl, 2,6-difluorophenyl, 2-bromothiophen-5-yl, 2-chlorothiophen-5-yl, 2-naphthyl, 2-phenoxyphenyl, 2-phenylquinolin-4-yl, 2-tolyl, 3-(2-chlorophenyl)-5-methylisoxazol-4-yl, 3,4,5-trimethoxyphenyl, 3,5-dichlorophenyl, 3,5-dimethoxyphenyl, 3-bromophenyl, 3-chlorobenzo[b]thiophen-2-yl, 3-chlorophenyl, 3-fluorophenyl, 3-methoxyphenyl, 3-n-butoxyphenyl, 3-phenoxyphenyl, 3-tolyl, 3-trifluoromethylphenyl, 4-(2,6-dimethylmorpholinosulfonyl)phenyl, 4-(2-ethylpiperidin-1-ylsulfonyl)phenyl, 4-(2-methylpiperidin-1-ylsulfonyl)phenyl, 4-(2-phenylquinoline), 4-(3,4-dihydroisoquinolin-2(1H)-ylsulfonyl)phenyl, 4-(3,4-dihydroquinolin-1(2H)-ylsulfonyl)phenyl, 4-(3,5-dimethylpiperidin-1-ylsulfonyl)phenyl, 4-(4,4-dimethyloxazolidin-3-ylsulfonyl)phenyl, 4-(morpholinosulfonyl)phenyl, 4-(N,N-diallylsulfamoyl)phenyl, 4-(N,N-diethyl sulfamoyl)phenyl, 4-(N,N-diisobutylsulfamoyl)phenyl, 4-(N,N-dimethylsulfamoyl)phenyl, 4-(N-ethyl-N-benzyl sulfamoyl)phenyl, 4-(N-ethyl-N-n-butyl-sulfamoyl)phenyl, 4-(N-ethyl-N-phenyl sulfamoyl)phenyl, 4-(N-isopropyl-N-benzylsulfamoyl)phenyl 4-(N-methyl-N-benzylsulfamoyl)phenyl, 4-(N-methyl-N-cyclohexylsulfamoyl)phenyl, 4-(N-methyl-N-n-butyl sulfamoyl)phenyl, 4-(N-methyl-N-phenylsulfamoyl)phenyl, 4-(piperidin-1-ylsulfonyl)phenyl, 4-(pyrrolidin-1-ylsulfonyl)phenyl, 4-benzoylphenyl, 4-benzylphenyl, 4-biphenyl, 4-chlorophenyl, 4-diphenyl, 4-ethoxyphenyl, 4-fluorophenyl, 4-phenoxyphenyl, 4-tert-butylphenyl, 7-methoxybenzofuran-2-yl, benzo[d]thiazol-2-yl, benzo[d]thiazol-4-yl, benzo[d]thiazol-6-yl, benzofuran-2-yl, diphenylmethyl, methyl-4-benzoate, phenyl, or thiophen-2-yl, and $R^2$ may be 1,2,3,4-tetrahydronaphthalen-6-yl, 2-(methylthio)phenyl, 2,3-dihydro-1,4-dioxin-2-yl, 2,3-dihydrobenzo[b][1,4]-dioxin-2-yl, 2,3-dihydrobenzo[b][1,4]-dioxin-6-yl, 2,4-dichlorophenyl, 2,4-dimethoxyphenyl, 2,4-dimethylphenyl, 2,5-dichlorophenyl, 2,5-dichlorothiophen-3-yl 2,5-dimethylphenyl, 2-bromothiophen-2-yl, 2-chlorophenyl, 2-chlorothiophen-2-yl, 2-chlorothiophen-5-yl, 2-furanyl, 2-methoxyphenyl, 2-pyridinyl, 3-(methylthio)phenyl, 3,4,5-trimethoxyphenyl, 3,4-dimethoxyphenyl, 3,4-dimethylphenyl, 3,5-dimethoxyphenyl, 3-methoxyphenyl, 3-pyridinyl, 4-chlorophenyl, 4-(methylthio)phenyl, 4-bromophenyl, 4-ethoxyphenyl, 4-fluorophenyl, 4-isopropylbenzyl, 4-methoxybenzyl, 4-methoxyphenyl, 4-pyridinyl, 4-trifluoromethoxyphenyl, 7-ethoxybenzofuran-2-yl, 7-methoxybenzofuran-2-yl, benzofuran-2-yl, benzyl, phenyl, or thiophen-2-yl, or an antibiotic potentiator having the structure:

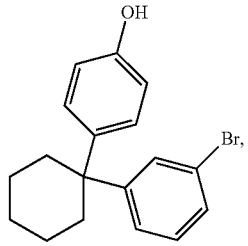 [SMILES: Oc1ccc(C2(c3cccc(Br)c3)CCCCC2)cc1]

or an antibiotic potentiator having the formula:

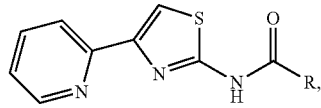

wherein R may be 2-phenoxyphenyl, 2-bromothiophen-5-yl, or 2,5-dichlorophenyl; or an antibiotic potentiator having the formula:

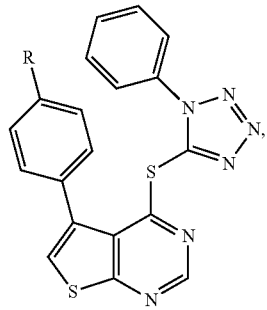

wherein R may be fluoro, or chloro, or an antibiotic potentiator having the structure:

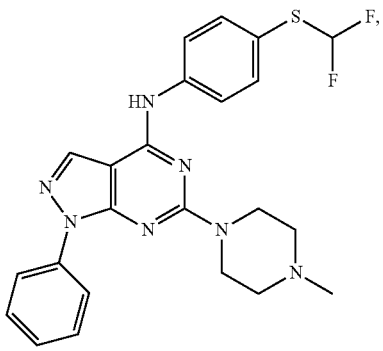 [SMILES: CN1CCN(c2nc(Nc3ccc(SC(F)F)cc3)c3cnn(-c4ccccc4)c3n2)CC1]

or
an antibiotic potentiator having the structure:

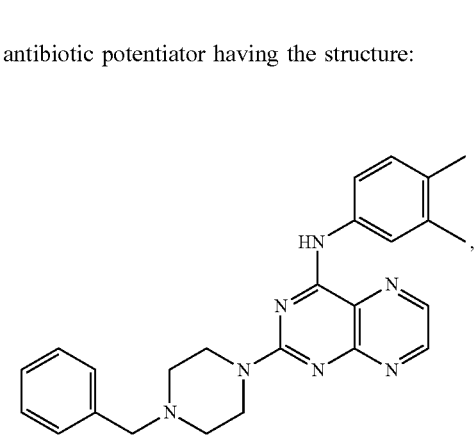

or
an antibiotic potentiator having the structure:

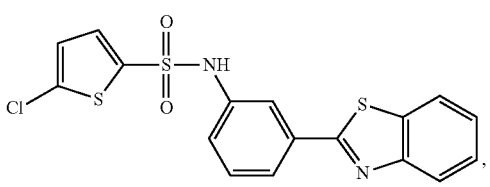 [SMILES: O=S(=O)(Nc1cccc(-c2nc3ccccc3s2)c1)c1ccc(Cl)s1]

or
an antibiotic potentiator having the structure:

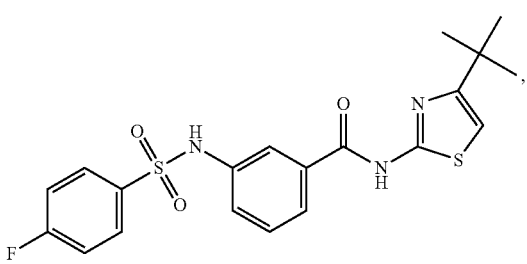 [SMILES: CC(C)(C)c1csc(NC(=O)c2cccc(NS(=O)(=O)c3ccc(F)cc3)c2)n1]

or an antibiotic potentiator having the structure:

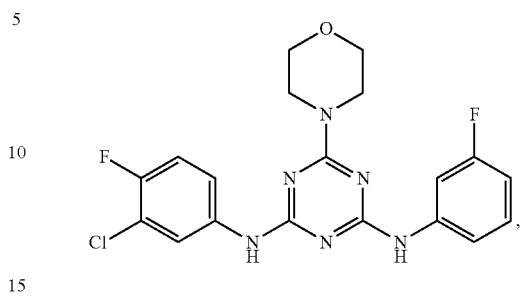

or
an antibiotic potentiator having the structure:

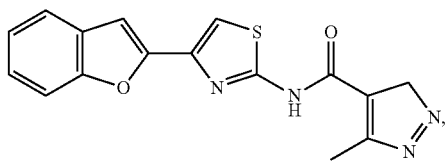 [SMILES: CC1=C(C(=O)Nc2nc(-c3cc4ccccc4o3)cs2)CN=N1]

or
an antibiotic potentiator having the structure:

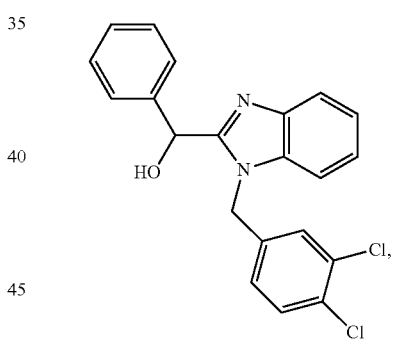

or
an antibiotic potentiator having the formula:

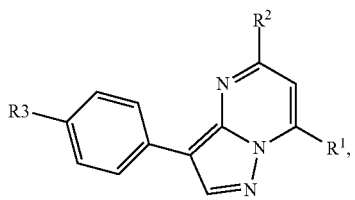

wherein $R^1$ may be N-(4-(phenylamino)-N'-(phenyl)acetamide)amine, N-3-(N',N'-dimethylamine)propylamine, N-(4-N'-phenylacetamide)amine, or hydroxyl, and $R^2$ may be tert-butyl, isopropyl, or phenyl, and $R^3$ may be hydrogen or chloro, or an antibiotic potentiator having the structure:

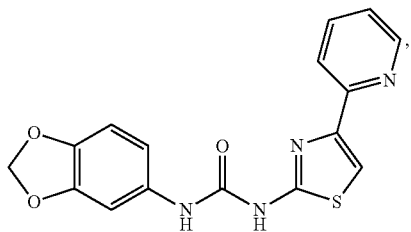 [SMILES: O=C(Nc1ccc2c(c1)OCO2)Nc1nc(-c2ccccn2)cs1]

or
an antibiotic potentiator having the formula:

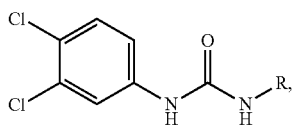

wherein R may be 1H-indazol-6-yl, or 3-(4-methoxyphenoxy)methyloxadiazol-5-yl-methyl, or
an antibiotic potentiator having the formula:

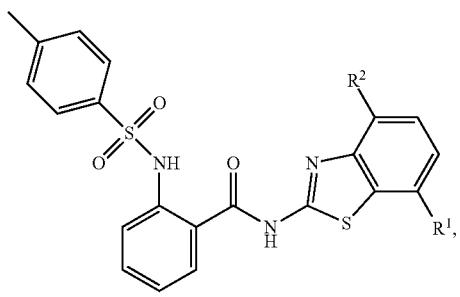

wherein, $R^1$ and $R^2$ may each be separately hydrogen, methyl, chloro or methylthio, or a prodrug or comparable salt thereof.

2. The method of claim 1, wherein the antibiotic is a penicillinase-resistant beta-lactam antibiotic.

3. The method of claim 2, wherein the penicillinase-resistant beta-lactam antibiotic is oxacillin, methicillin, nafcillin, cloxacillin, dicloxacillin or flucloxacillin.

4. The method of claim 1, wherein the subject has been tested for a *staphylococcus* infection, is diagnosed with a *staphylococcus* infection, is at risk of acquiring a *staphylococcus* infection, or has one or more symptoms of a staphylococcal infection.

5. The method of claim 1, wherein the *staphylococcus* infection is *Staphylococcus aureus* or methicillin resistant *Staphylococcus aureus* (MRSA).

6. The method of claim 1, wherein the subject has or is at risk for native valve endocarditis or prosthetic valve endocarditis.

7. The method of claim 6, wherein the subject is administered 2-3 g of oxacillin intravenously every 4 to 6 hours.

8. The method of claim 1, wherein the subject has or is at risk for joint infection, meningitis, osteomyelitis, pneumonia, septicemia, sinusitis, or skin or soft tissue infection.

9. The method of claim 5, wherein the subject is administered 1-2 g of oxacillin intravenously or intramuscularly every 4 to 6 hours or 500 mg to 1 g of oxacillin orally every 4 to 6 hours.

10. The method of claim 1, wherein treating a staphylococcal infection comprises reducing abscess formation or incidence or reducing bacterial load in the subject.

11. The method of claim 1, further comprising administering a second antibiotic or a staphylococcal vaccine; wherein the second antibiotic is gentamicin or rifampin.

12. The method of claim 1, wherein the antibiotic is administered at a dose of 0.1 mg/kg to 50 mg/kg and/or the antibiotic potentiator is administered at a dose of 0.1 mg/kg to 100 mg/kg.

13. The method of claim 12, wherein the subject is a pediatric patient.

14. The method of claim 13, wherein the pediatric patient is administered 25 mg/kg to 50 mg/kg of oxacillin intravenously or intramuscularly every 6 to 12 hours or 12.5 mg/kg of oxacillin orally every 6 hours.

15. The method of claim 1, whereby administration to a subject is oral, sublingual, sublabial, gastrointestinal, rectal, epicutaneous (topical), intradermal, subcutaneous, nasal, intravenous, intraarterial, intramuscular, intracardiac, intraosseous, intrathecal, intraperitoneal, intravesical, intravitreal, intracavernous, intravaginal, intrauterine, epidural, intracerebral and/or intracerebroventricular, enteral, parenteral, onto the skin, inhalation, an enema, eye drops, ear drops, absorption across mucosal membranes, the mouth, a gastric feeding tube, a duodenal feeding tube, a suppository, an injection into a vein, an injection into an artery, an injection into the bone marrow, an injection into muscle tissue, an injection into the brain, an injection into the cerebral ventricular system or an injection under the skin.

16. The method of claim 1, wherein the antibiotic and the antibiotic potentiator are administered in the same composition or wherein the antibiotic and the antibiotic potentiator are administered simultaneously.

17. The method of claim 1, wherein the antibiotic is administered up to 24 hours prior to administration of the antibiotic potentiator; wherein the antibiotic potentiator is administered up to 24 hours prior to administration of the antibiotic; or wherein the antibiotic and antibiotic potentiator are administered within 24 hours of each other.

18. A pharmaceutical composition comprising an antibiotic and a compound selected from the group consisting of

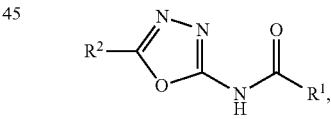

wherein $R^1$ may be -(4-chlorophenoxy)methyl, 1-(thiophen-2-yl)cyclopentyl, 1,2,3,4-tetrahydronaphthalen-6-yl, 1-isopropyl-1H-pyrazol-5-yl, 2-(thiophen-2-yl)quinolin-4-yl, 2,3-dihyrdobenzo[b][1,4]dioxin-6-yl, 2,4-dichlorophenyl, 2,5-dichlorophenyl, 2,5-dichlorothiophen-3-yl, 2,6-difluorophenyl, 2-bromothiophen-5-yl, 2-chlorothiophen-5-yl, 2-naphthyl, 2-phenoxyphenyl, 2-phenylquinolin-4-yl, 2-tolyl, 3-(2-chlorophenyl)-5-methylisoxazol-4-yl, 3,4,5-trimethoxyphenyl, 3,5-dichlorophenyl, 3,5-dimethoxyphenyl, 3-bromophenyl, 3-chlorobenzo[b]thiophen-2-yl, 3-chlorophenyl, 3-fluorophenyl, 3-methoxyphenyl, 3-n-butoxyphenyl, 3-phenoxyphenyl, 3-tolyl, 3-trifluoromethylphenyl, 4-(2,6-dimethylmorpholinosulfonyl)phenyl, 4-(2-ethylpiperidin-1-ylsulfonyl)phenyl, 4-(2-methylpiperidin-1-ylsulfonyl)phenyl, 4-(2-phenylquinoline), 4-(3,4-dihydroisoquinolin-2(1H)-ylsulfonyl)phenyl, 4-(3,4-dihydroquinolin-1(2H)-ylsulfonyl)phenyl, 4-(3,5- dimethylpiperidin-1-ylsulfonyl)phenyl, 4-(4,4-dimethyloxazolidin-3-ylsulfonyl)phenyl, 4-(morpholinosulfonyl)phenyl, 4-(N,N-diallylsulfamoyl)phenyl, 4-(N,N-diethyl sulfamoyl)phenyl, 4-(N,N-diisobutylsulfamoyl)phenyl, 4-(N,N-dimethylsulfamoyl)phenyl, 4-(N-ethyl-N-benzyl sulfamoyl)phenyl, 4-(N-ethyl-N-n-butyl-sulfamoyl)phenyl, 4-(N-ethyl-N-phenyl sulfamoyl)phenyl, 4-(N-isopropyl-N-benzylsulfamoyl)phenyl 4-(N-methyl-N-benzyl sulfamoyl)phenyl, 4-(N-methyl-N-cyclohexylsulfamoyl)phenyl, 4-(N-methyl-N-n-butyl sulfamoyl)phenyl, 4-(N-methyl-N-phenylsulfamoyl)phenyl, 4-(piperidin-1-ylsulfonyl)phenyl, 4-(pyrrolidin-1-ylsulfonyl)phenyl, 4-benzoylphenyl, 4-benzylphenyl, 4-biphenyl, 4-chlorophenyl, 4-diphenyl, 4-ethoxyphenyl, 4-fluorophenyl, 4-phenoxyphenyl, 4-tert-butylphenyl, 7-methoxybenzofuran-2-yl, benzo[d]thiazol-2-yl, benzo[d]thiazol-4-yl, benzo[d]thiazol-6-yl, benzofuran-2-yl, diphenylmethyl, methyl-4-benzoate, phenyl, or thiophen-2-yl, and $R^2$ may be 1,2,3,4-tetrahydronaphthalen-6-yl, 2-(methylthio)phenyl, 2,3-dihydro-1,4-dioxin-2-yl, 2,3-dihydrobenzo[b][1,4]-dioxin-2-yl, 2,3-dihydrobenzo[b][1,4]-dioxin-6-yl, 2,4-dichlorophenyl, 2,4-dimethoxyphenyl, 2,4-dimethylphenyl, 2,5-dichlorophenyl, 2,5-dichlorothiophen-3-yl 2,5-dimethylphenyl, 2-bromothiophen-2-yl, 2-chlorophenyl, 2-chlorothiophen-2-yl, 2-chlorothiophen-5-yl, 2-furanyl, 2-methoxyphenyl, 2-pyridinyl, 3-(methylthio)phenyl, 3,4,5-trimethoxyphenyl, 3,4-dimethoxyphenyl, 3,4-dimethylphenyl, 3,5-dimethoxyphenyl, 3-methoxyphenyl, 3-pyridinyl, 4-chlorophenyl, 4-(methylthio)phenyl, 4-bromophenyl, 4-ethoxyphenyl, 4-fluorophenyl, 4-isopropylbenzyl, 4-methoxybenzyl, 4-methoxyphenyl, 4-pyridinyl, 4-trifluoromethoxyphenyl, 7-ethoxybenzofuran-2-yl, 7-methoxybenzofuran-2-yl, benzofuran-2-yl, benzyl, phenyl, or thiophen-2-yl,

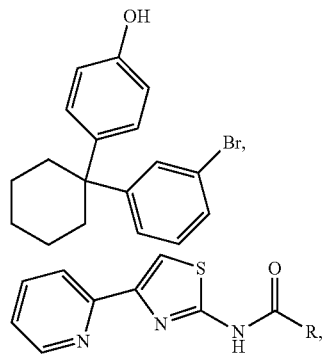

wherein R may be 2-phenoxyphenyl, 2-bromothiophen-5-yl, or 2,5-dichlorophenyl;

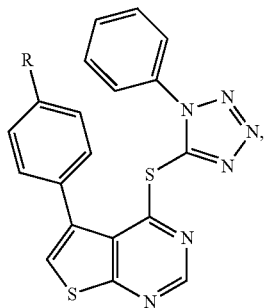

wherein R may be fluoro, or chloro,

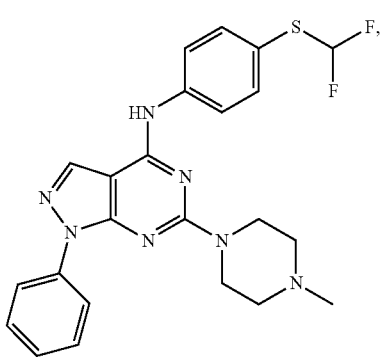

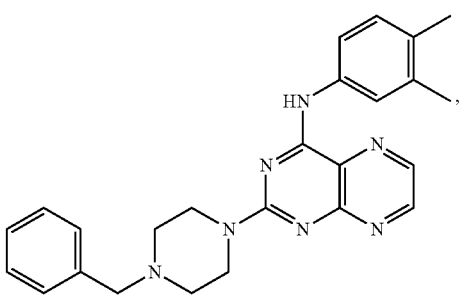

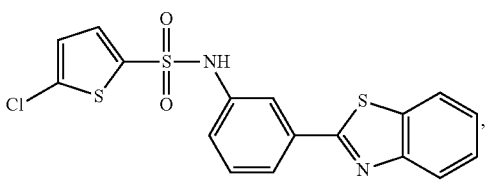

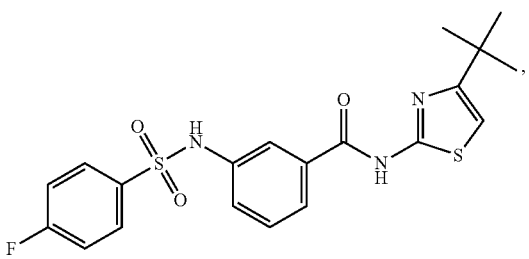

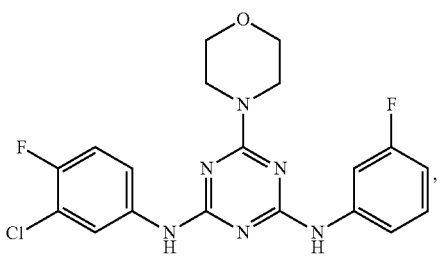

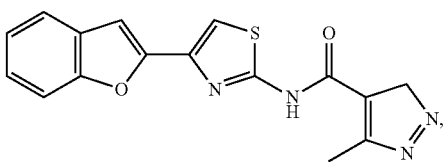

-continued

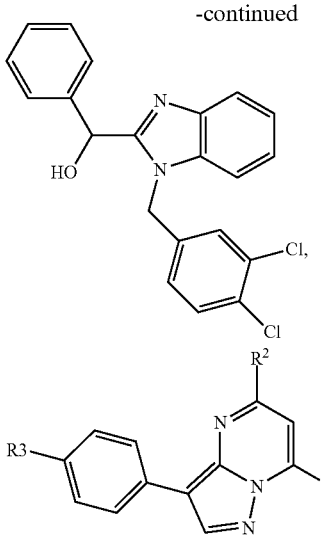

wherein R¹ may be N-(4-(phenylamino)-N'-(phenyl)acetamide)amine, N-3-(N',N'-dimethylamine)propylamine, N-(4-N'-phenylacetamide)amine, or hydroxyl, and R² may be tert-butyl, isopropyl, or phenyl, and R³ may be hydrogen or chloro,

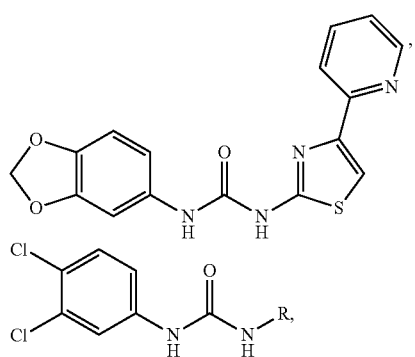

wherein R may be 1H-indazol-6-yl, or 3-(4-methoxyphenoxy)methyloxadiazol-5-yl-methyl, and

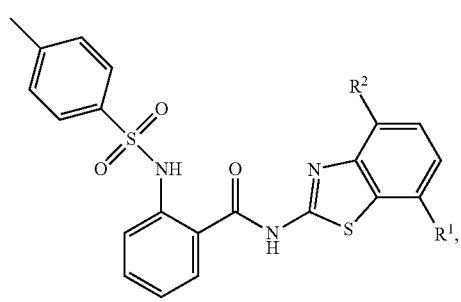

wherein, R¹ and R² may each be separately hydrogen, methyl, chloro or methylthio, or a prodrug or comparable salt thereof.

19. The pharmaceutical composition of claim 18, further comprising a further antibiotic, a staphylococcal vaccine composition and/or a polypeptide that specifically binds to a second Staphylococcal protein.

20. A system for treating a bacterial infection comprising a pharmaceutically acceptable composition comprising an antibiotic and a pharmaceutically acceptable composition comprising an antibiotic potentiator selected from the group consisting of

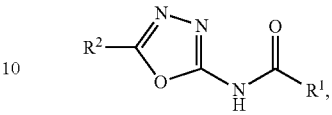

wherein R¹ may be -(4-chlorophenoxy)methyl, 1-(thiophen-2-yl)cyclopentyl, 1,2,3,4-tetrahydronaphthalen-6-yl, 1-isopropyl-1H-pyrazol-5-yl, 2-(thiophen-2-yl)quinolin-4-yl, 2,3-dihyrdobenzo[b][1,4]dioxin-6-yl, 2,4-dichlorophenyl, 2,5-dichlorophenyl, 2,5-dichlorothiophen-3-yl, 2,6-difluorophenyl, 2-bromothiophen-5-yl, 2-chlorothiophen-5-yl, 2-naphthyl, 2-phenoxyphenyl, 2-phenylquinolin-4-yl, 2-tolyl, 3-(2-chlorophenyl)-5-methylisoxazol-4-yl, 3,4,5-trimethoxyphenyl, 3,5-dichlorophenyl, 3,5-dimethoxyphenyl, 3-bromophenyl, 3-chlorobenzo[b]thiophen-2-yl, 3-chlorophenyl, 3-fluorophenyl, 3-methoxyphenyl, 3-n-butoxyphenyl, 3-phenoxyphenyl, 3-tolyl, 3-trifluoromethylphenyl, 4-(2,6-dimethylmorpholinosulfonyl)phenyl, 4-(2-ethylpiperidin-1-ylsulfonyl)phenyl, 4-(2-methylpiperidin-1-ylsulfonyl)phenyl, 4-(2-phenylquinoline), 4-(3,4-dihydroisoquinolin-2(1H)-ylsulfonyl)phenyl, 4-(3,4-dihydroquinolin-1(2H)-ylsulfonyl)phenyl, 4-(3,5-dimethylpiperidin-1-ylsulfonyl)phenyl, 4-(4,4-dimethyloxazolidin-3-ylsulfonyl)phenyl, 4-(morpholinosulfonyl)phenyl, 4-(N,N-diallylsulfamoyl)phenyl, 4-(N,N-diethyl sulfamoyl)phenyl, 4-(N,N-diisobutylsulfamoyl)phenyl, 4-(N,N-dimethylsulfamoyl)phenyl, 4-(N-ethyl-N-benzyl sulfamoyl)phenyl, 4-(N-ethyl-N-n-butyl-sulfamoyl)phenyl, 4-(N-ethyl-N-phenyl sulfamoyl)phenyl, 4-(N-isopropyl-N-benzylsulfamoyl)phenyl 4-(N-methyl-N-benzyl sulfamoyl)phenyl, 4-(N-methyl-N-cyclohexylsulfamoyl)phenyl, 4-(N-methyl-N-n-butyl sulfamoyl)phenyl, 4-(N-methyl-N-phenylsulfamoyl)phenyl, 4-(piperidin-1-ylsulfonyl)phenyl, 4-(pyrrolidin-1-ylsulfonyl)phenyl, 4-benzoylphenyl, 4-benzylphenyl, 4-biphenyl, 4-chlorophenyl, 4-diphenyl, 4-ethoxyphenyl, 4-fluorophenyl, 4-phenoxyphenyl, 4-tert-butylphenyl, 7-methoxybenzofuran-2-yl, benzo[d]thiazol-2-yl, benzo[d]thiazol-4-yl, benzo[d]thiazol-6-yl, benzofuran-2-yl, diphenylmethyl, methyl-4-benzoate, phenyl, or thiophen-2-yl, and R² may be 1,2,3,4-tetrahydronaphthalen-6-yl, 2-(methylthio)phenyl, 2,3-dihydro-1,4-dioxin-2-yl, 2,3-dihydrobenzo[b][1,4]-dioxin-2-yl, 2,3-dihydrobenzo[b][1,4]-dioxin-6-yl, 2,4-dichlorophenyl, 2,4-dimethoxyphenyl, 2,4-dimethylphenyl, 2,5-dichlorophenyl, 2,5-dichlorothiophen-3-yl 2,5-dimethylphenyl, 2-bromothiophen-2-yl, 2-chlorophenyl, 2-chlorothiophen-2-yl, 2-chlorothiophen-5-yl, 2-furanyl, 2-methoxyphenyl, 2-pyridinyl, 3-(methylthio)phenyl, 3,4,5-trimethoxyphenyl, 3,4-dimethoxyphenyl, 3,4-dimethylphenyl, 3,5-dimethoxyphenyl, 3-methoxyphenyl, 3-pyridinyl, 4-chlorophenyl, 4-(methylthio)phenyl, 4-bromophenyl, 4-ethoxyphenyl, 4-fluorophenyl, 4-isopropylbenzyl, 4-methoxybenzyl, 4-methoxyphenyl, 4-pyridinyl, 4-trifluoromethoxyphenyl, 7-ethoxybenzofuran-2-yl, 7-methoxybenzofuran-2-yl, benzofuran-2-yl, benzyl, phenyl, or thiophen-2-yl,

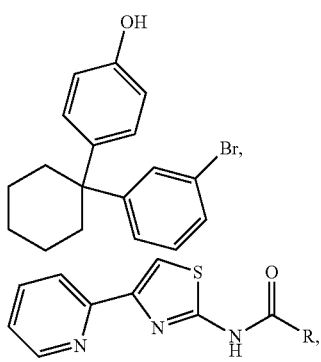
wherein R may be 2-phenoxyphenyl, 2-bromothiophen-5-yl, or 2,5-dichlorophenyl;
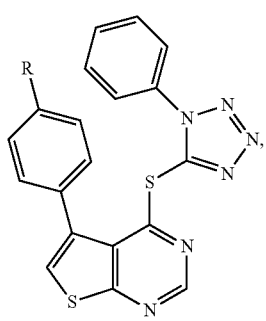
wherein R may be fluoro, or chloro,
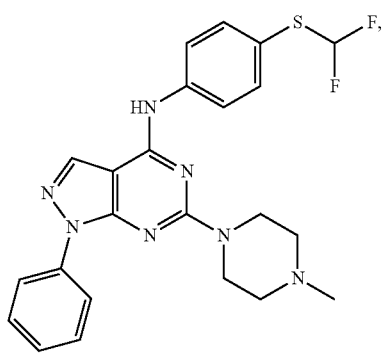
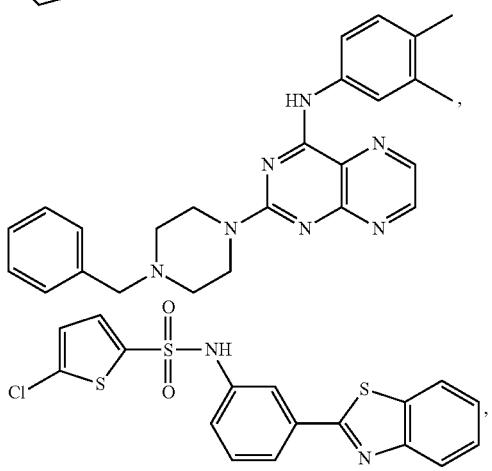
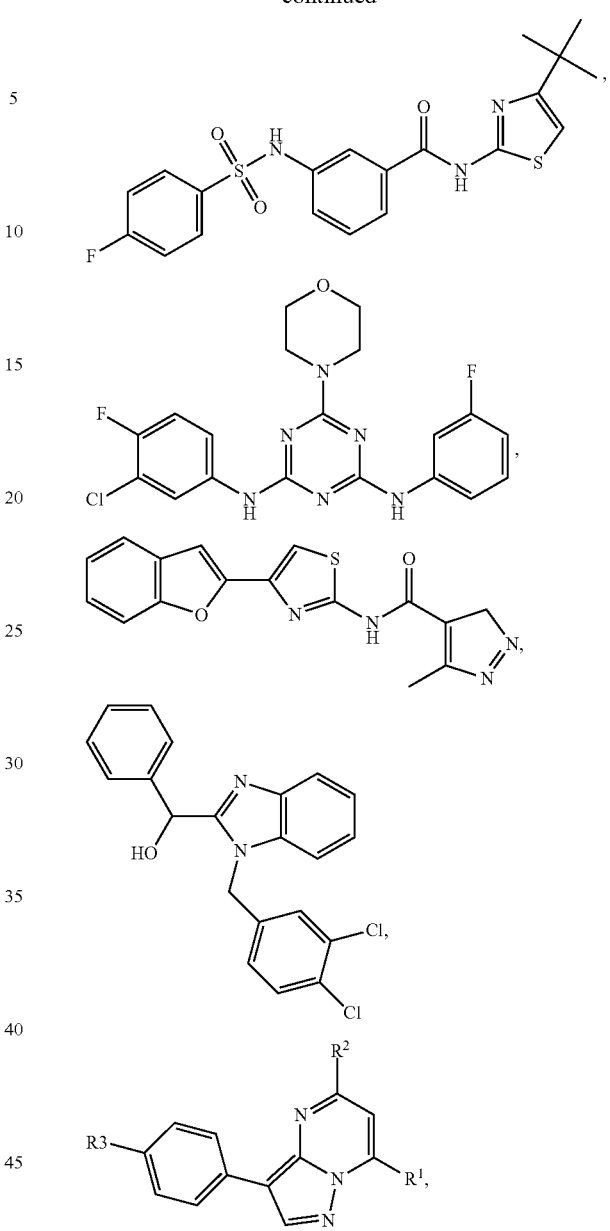
wherein R[1] may be N-(4-(phenylamino)-N'-(phenyl)acetamide)amine, N-3-(N',N'-dimethylamine)propylamine, N-(4-N'-phenylacetamide)amine, or hydroxyl, and R[2] may be tert-butyl, isopropyl, or phenyl, and R[3] may be hydrogen or chloro,
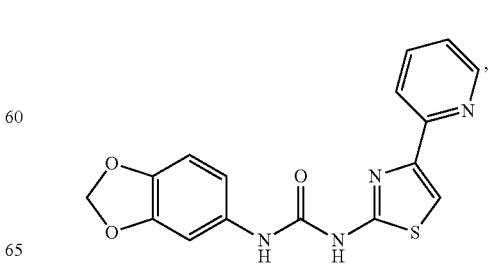

-continued
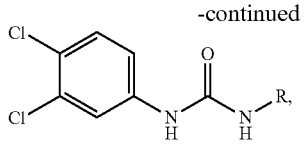
wherein R may be 1H-indazol-6-yl, or 3-(4-methoxyphenoxy)methyloxadiazol-5-yl-methyl, and
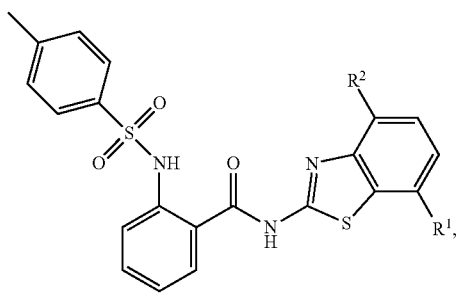
wherein, $R^1$ and $R^2$ may each be separately hydrogen, methyl, chloro or methylthio, or a prodrug or comparable salt thereof.
* * * * *

UNITED STATES PATENT AND TRADEMARK OFFICE
CERTIFICATE OF CORRECTION

PATENT NO. : 9,675,592 B2
APPLICATION NO. : 14/776965
DATED : June 13, 2017
INVENTOR(S) : Robert S. Daum, Susan Boyle-Vavra and Michael E. Johnson It is certified that error appears in the above-identified patent and that said Letters Patent is hereby corrected as shown below:

In the Specification

In Column 1 at Line 14, the following subtitle and paragraph should be added:
STATEMENT OF GOVERNMENT SUPPORT
This invention was made with government support under grant number R21 AI111760 awarded by the National Institutes of Health. The government has certain rights in the invention.

Signed and Sealed this
Ninth Day of October, 2018

Andrei Iancu
*Director of the United States Patent and Trademark Office*